US011596685B2

(12) United States Patent
Micol et al.

(10) Patent No.: US 11,596,685 B2
(45) Date of Patent: *Mar. 7, 2023

(54) COMPOSITIONS AND METHODS FOR ORGAN-PROTECTIVE EXPRESSION AND MODULATION OF CODING RIBONUCLEIC ACIDS

(71) Applicant: Combined Therapeutics, Inc., Cambridge, MA (US)

(72) Inventors: Romain Micol, Cambridge, MA (US); Valerie Duval, Cambridge, MA (US)

(73) Assignee: Combined Therapeutics, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/689,908

(22) Filed: Mar. 8, 2022

(65) Prior Publication Data

US 2022/0202932 A1 Jun. 30, 2022

Related U.S. Application Data

(63) Continuation of application No. PCT/US2021/019028, filed on Feb. 22, 2021.

(60) Provisional application No. 63/059,458, filed on Jul. 31, 2020, provisional application No. 62/979,619, filed on Feb. 21, 2020.

(51) Int. Cl.
*A61K 39/215* (2006.01)
*C12N 15/113* (2010.01)
*A61K 39/00* (2006.01)

(52) U.S. Cl.
CPC .......... *A61K 39/215* (2013.01); *C12N 15/113* (2013.01); *A61K 2039/53* (2013.01)

(58) Field of Classification Search
None
See application file for complete search history.

(56) References Cited

U.S. PATENT DOCUMENTS

| 7,993,831 B2 | 8/2011 | Latham et al. |
| 8,556,882 B2 | 10/2013 | Morgan et al. |
| 2009/0075258 A1 | 3/2009 | Latham et al. |
| 2012/0071859 A1 | 3/2012 | Morgan et al. |
| 2018/0311343 A1* | 11/2018 | Huang .................. A61K 39/02 |
| 2019/0125839 A1* | 5/2019 | Frederick ............. A61K 9/5123 |
| 2022/0273790 A1* | 9/2022 | Prasad .................. A61K 39/12 |

FOREIGN PATENT DOCUMENTS

| WO | WO 2019/158955 A9 | 8/2019 | |
| WO | WO-2021165667 A1 * | 8/2021 | ........... A61K 39/215 |

OTHER PUBLICATIONS

Jordan, B. Vaccination against infectious bronchitis virus: A continuous challenge. Veterinary Microbiology 206 (2017) 137-143.*
Li et al. Coronavirus vaccine development: from SARS and MERS to COVID-19. J Biomed Sci (2020) 27:104.*
Cui et al. Recombinant chicken interleukin-7 as a potent adjuvant increases the immunogenicity and protection of inactivated infectious bursal disease vaccine. Vet Res (2018), 49:10.*
Jiang et al. SARS Vaccine Development. Emerging Infectious Diseases, vol. 11, No. 7, Jul. 2005, pp. 1016-1020.*

* cited by examiner

*Primary Examiner* — Nianxiang Zou
(74) *Attorney, Agent, or Firm* — DLA Piper LLP (US)

(57) ABSTRACT

Compositions are provided comprising messenger RNA constructs having at least one open reading frame (ORF), wherein the ORF is operatively linked to at least one untranslated region (UTR), wherein the UTR comprises at least one organ protection sequence (OPS), wherein the OPS sequence comprises at least a first, a second and a third micro-RNA (miRNA) target sequence, and wherein each of the at least a first, second and third the miRNA target sequences are optimised to hybridise with a corresponding miRNA sequence. The compositions and molecules provided are useful in therapies such as for the treatment of cancer, in immunotherapies, and in vaccines.

18 Claims, 16 Drawing Sheets

Specification includes a Sequence Listing.

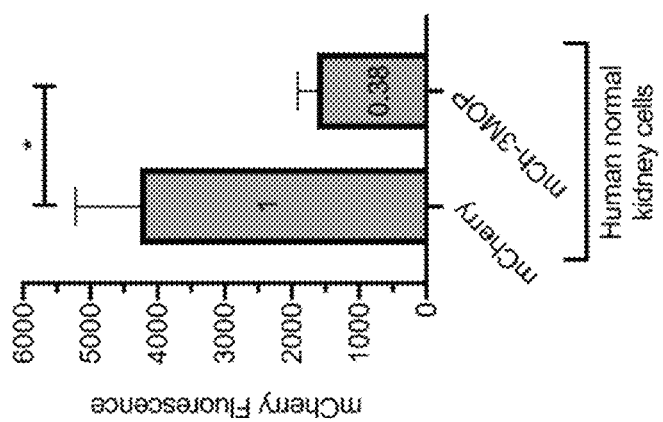
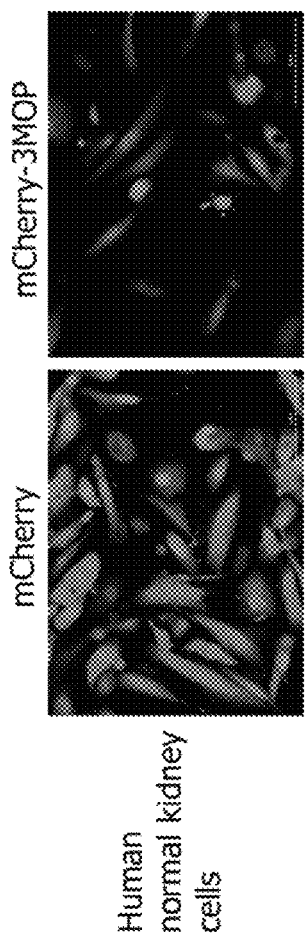
FIG. 5A
FIG. 5B

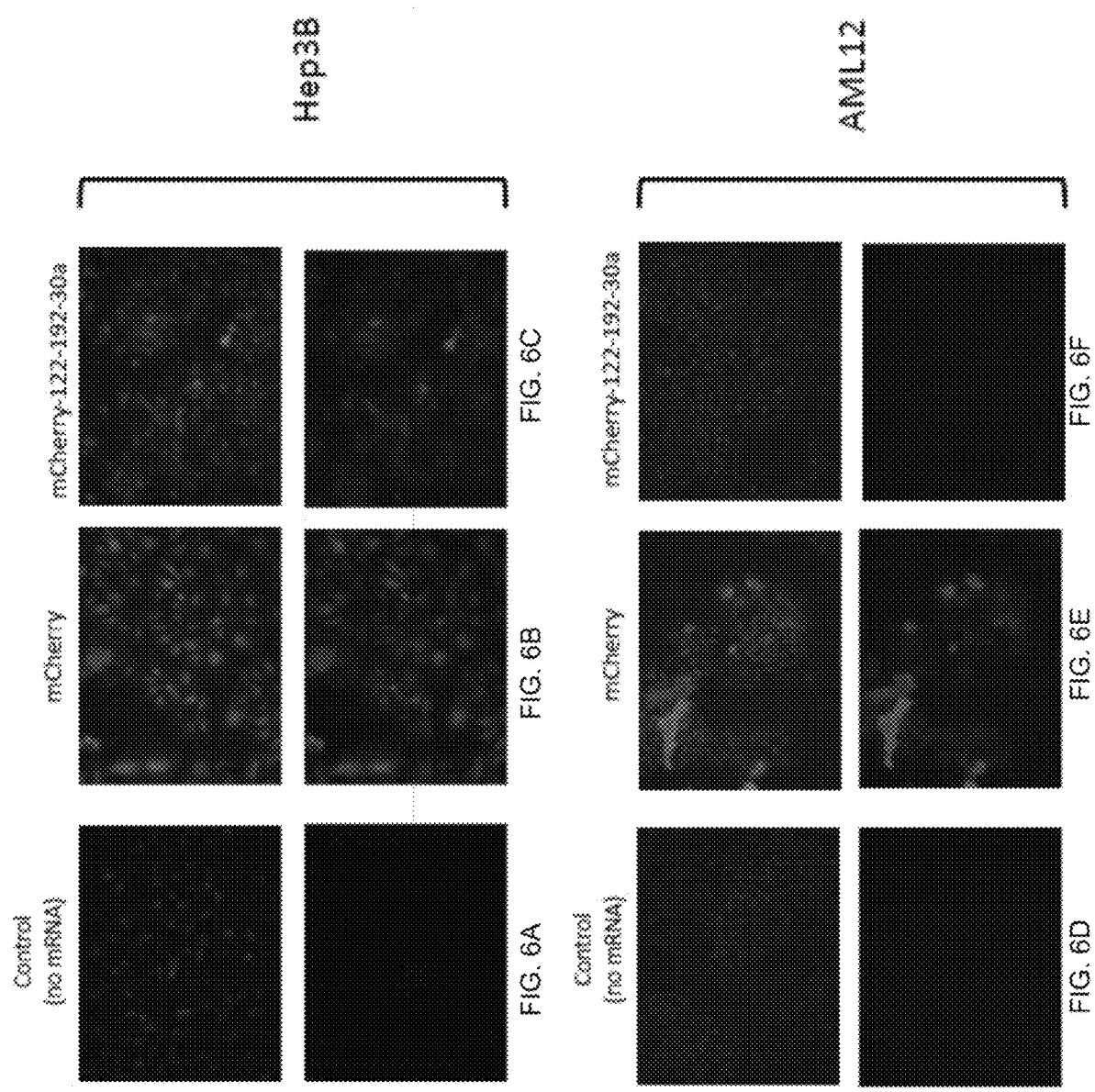

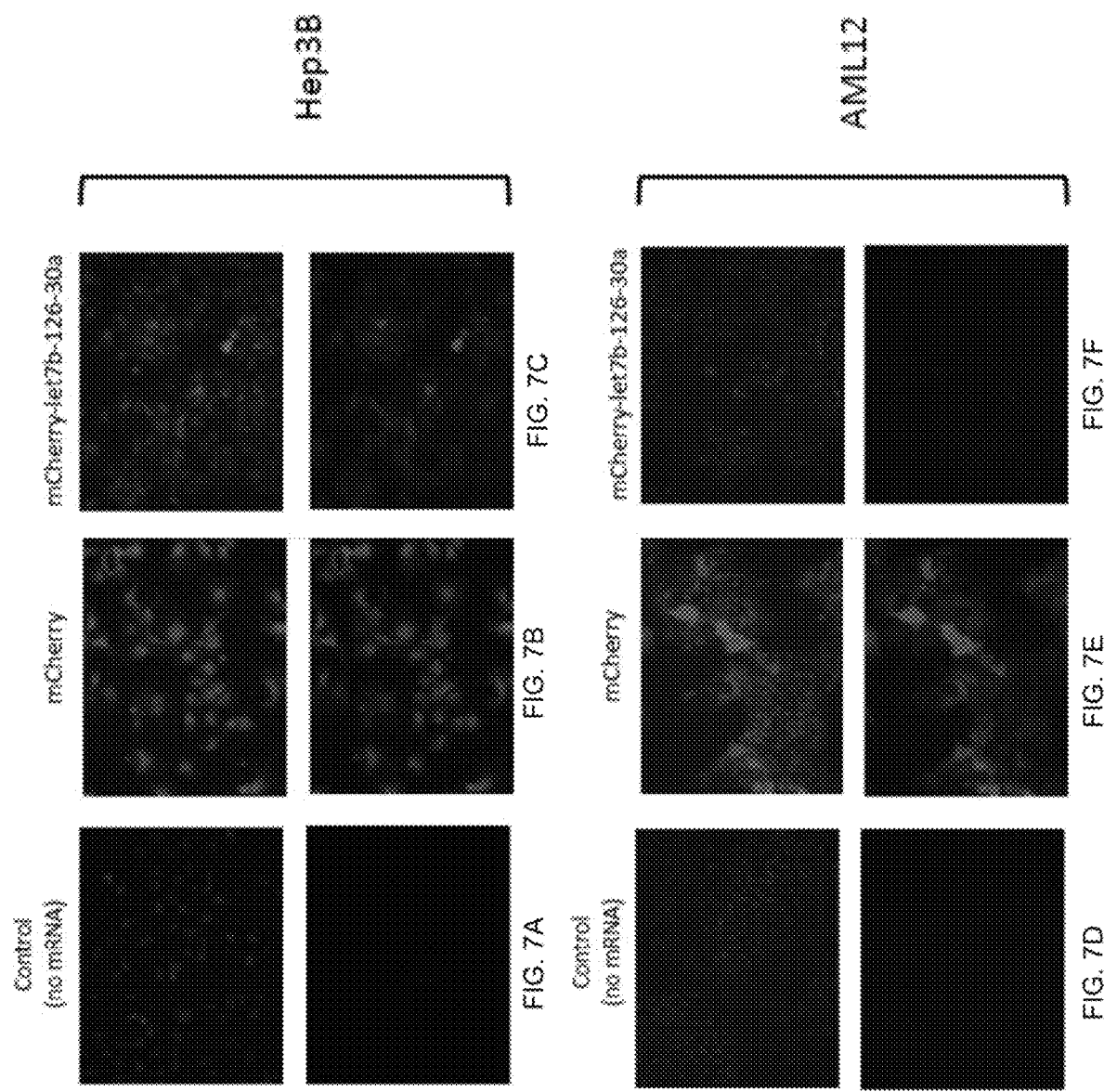

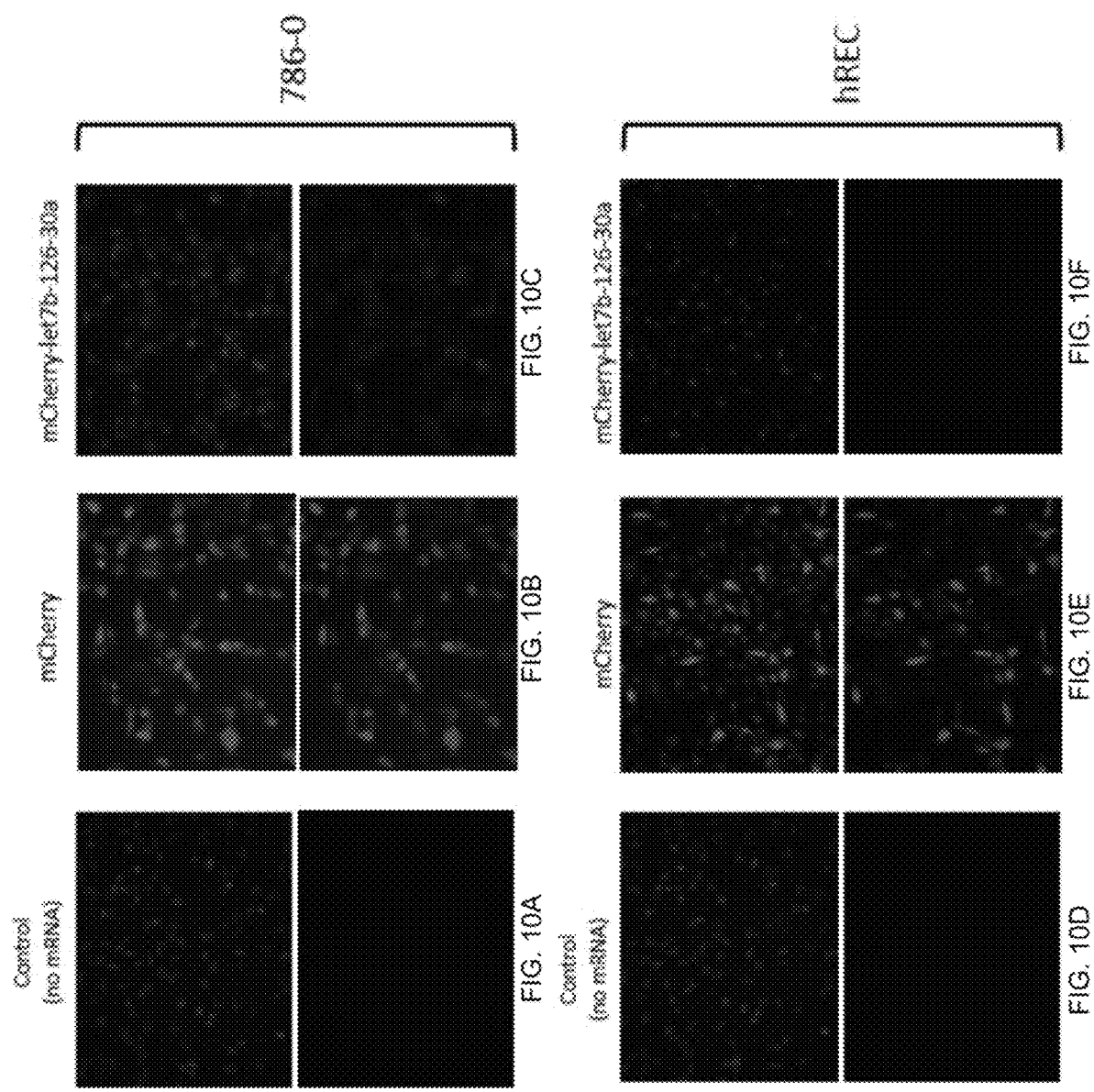

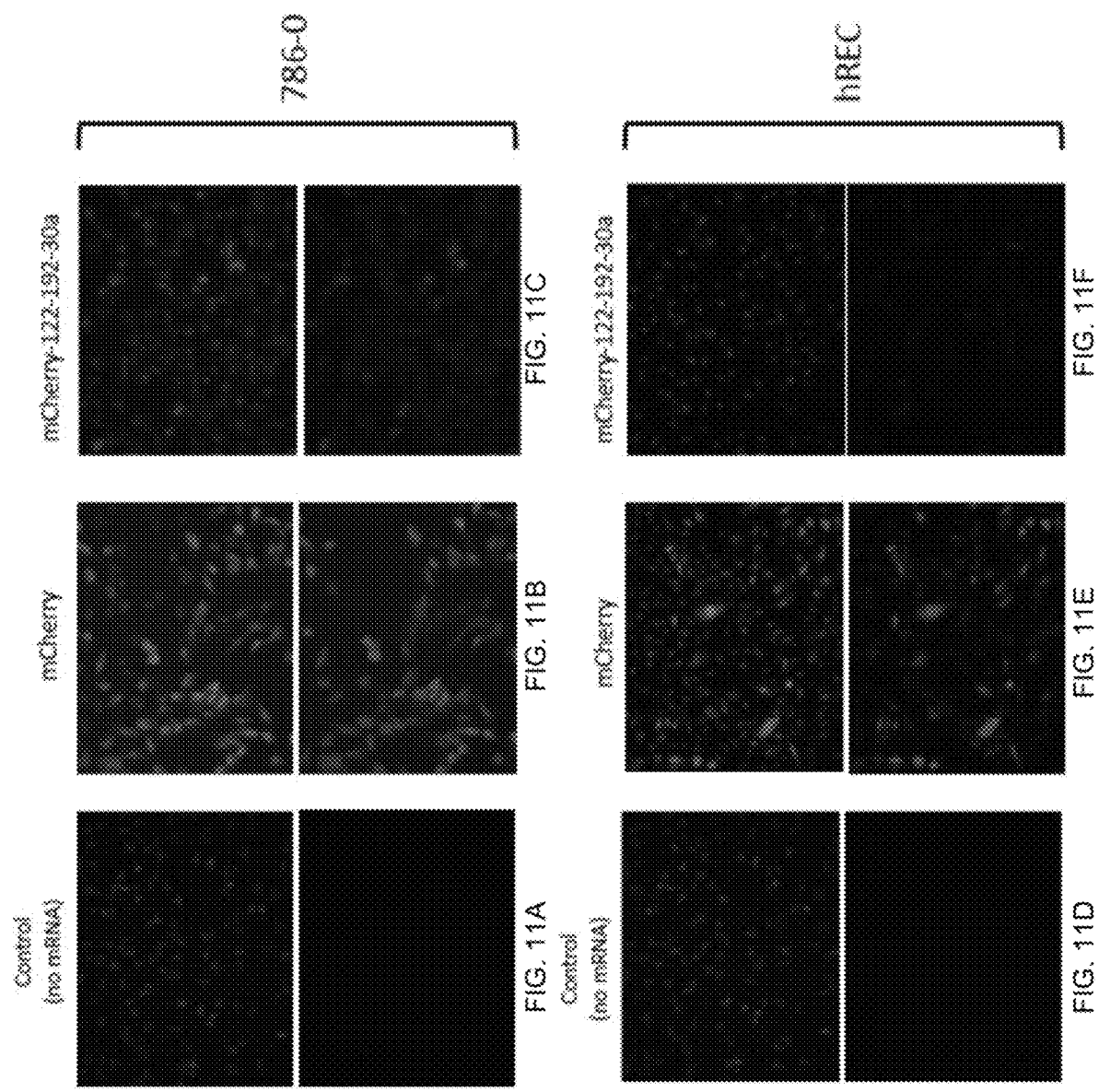

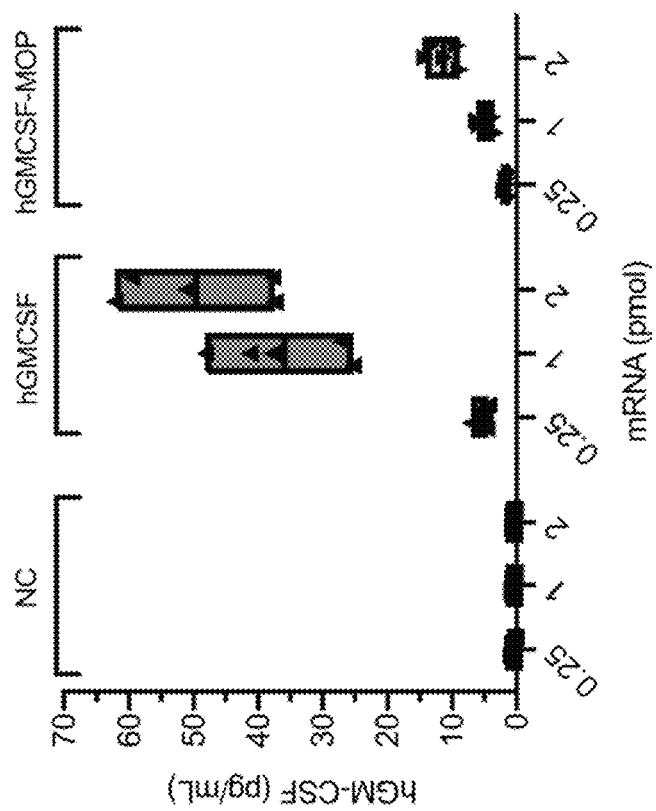
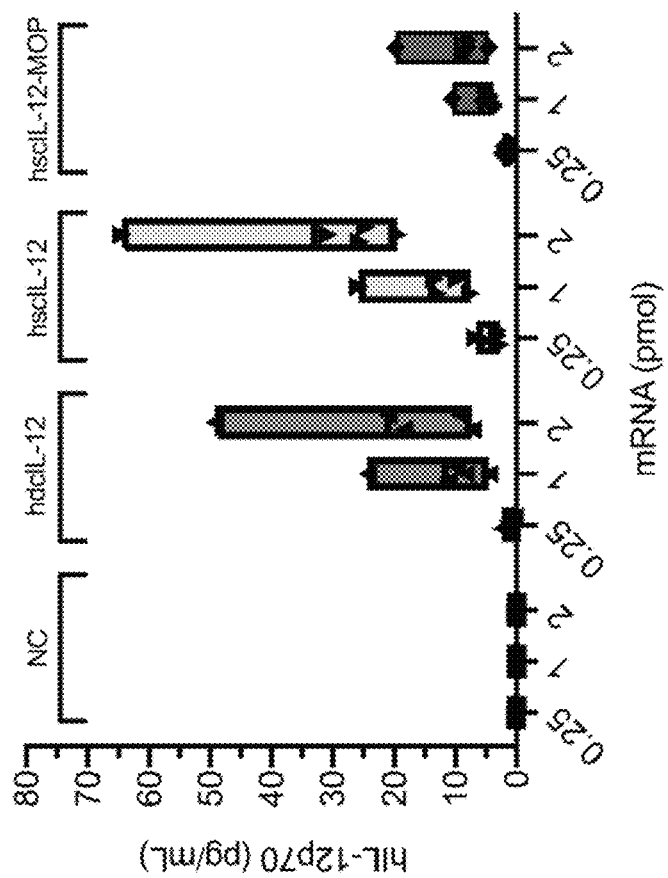
FIG. 12A
FIG. 12B

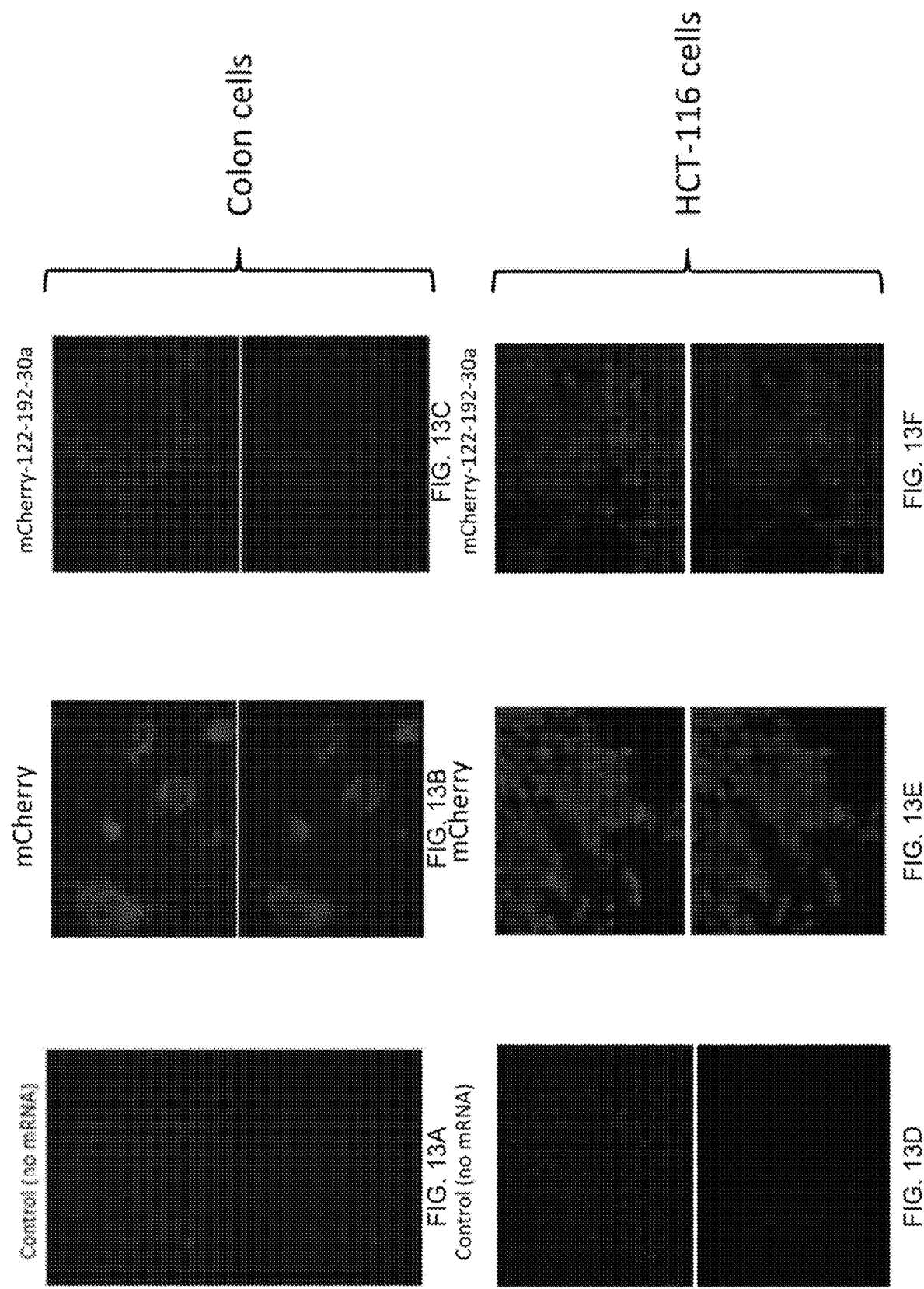

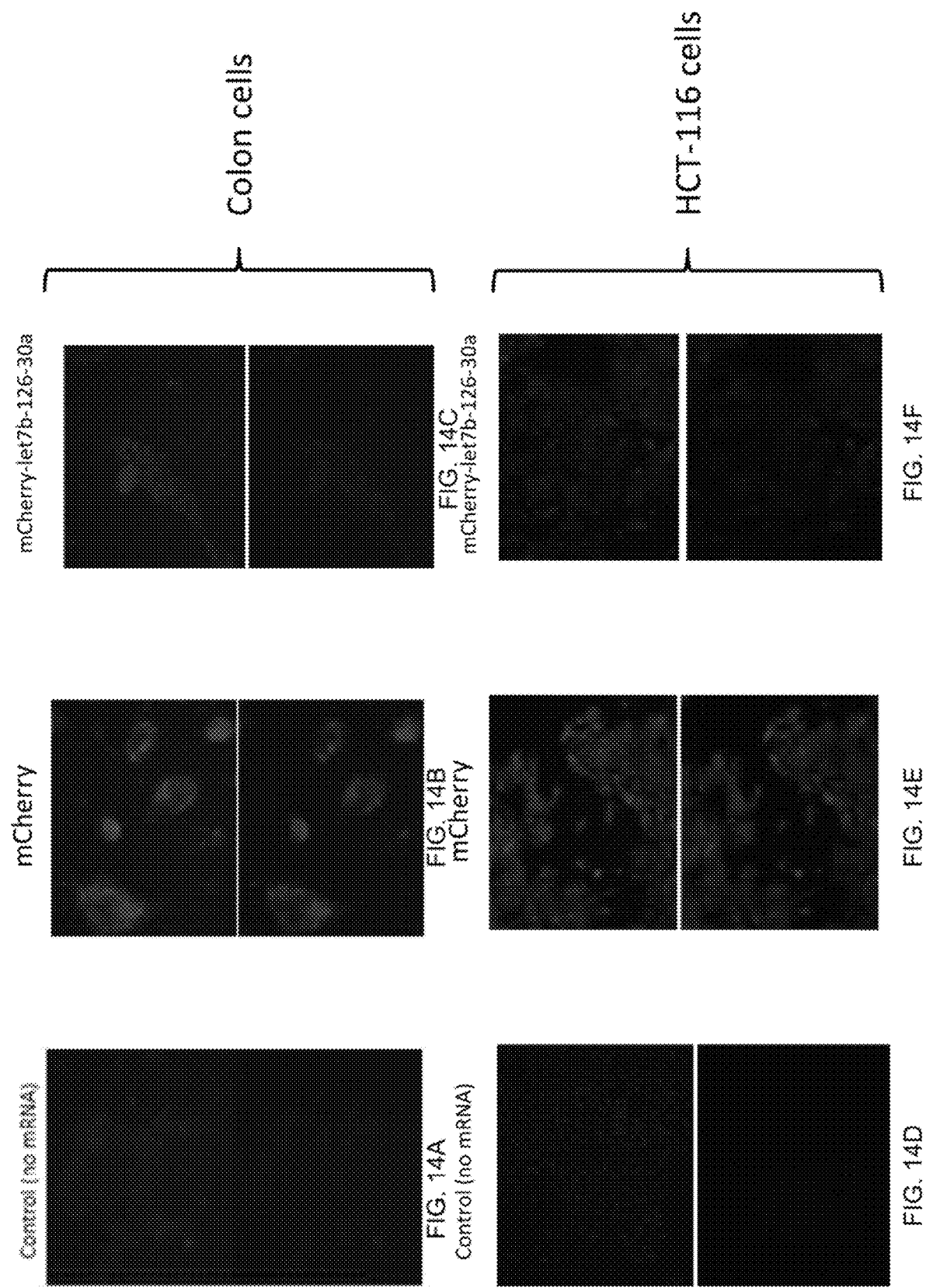

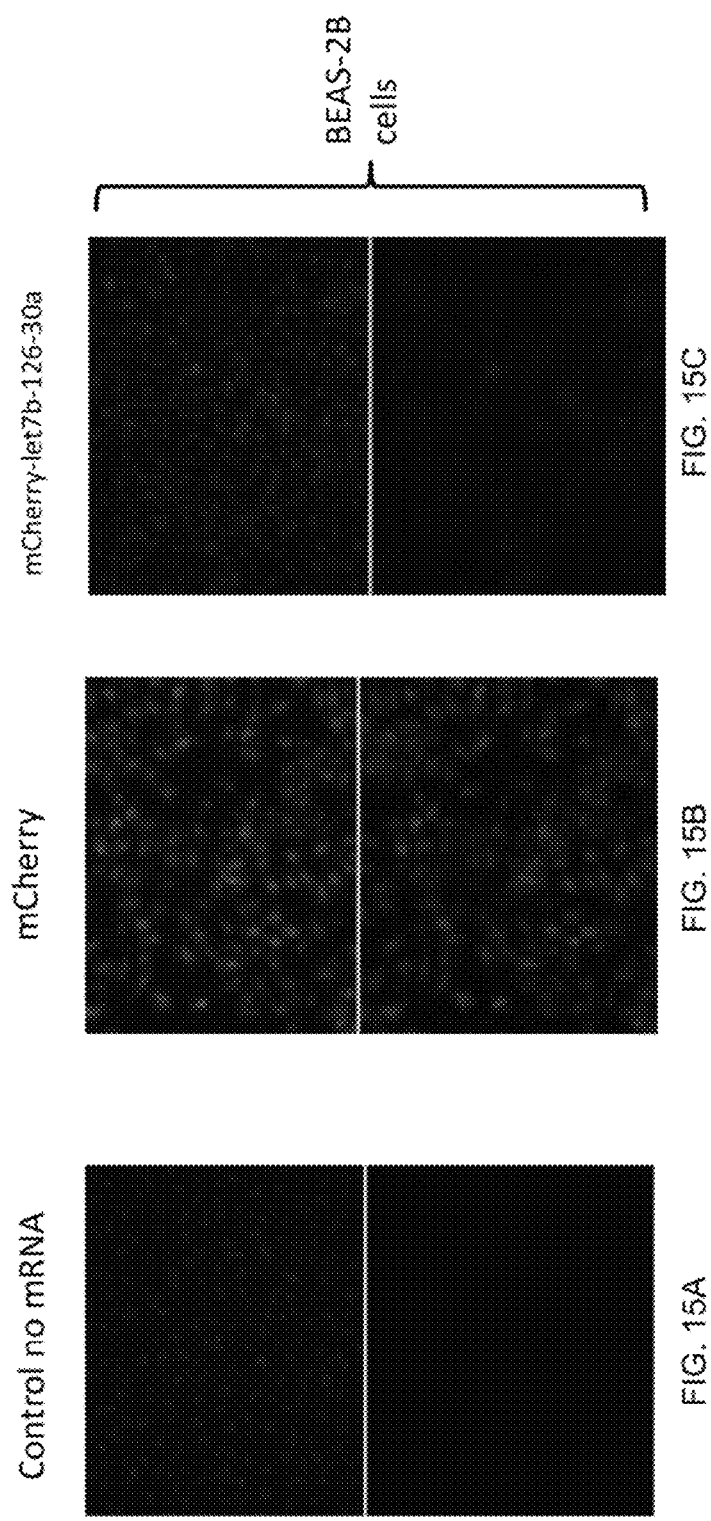

SEQUENCE LISTING

<160> NUMBER OF SEQ ID NOS: 65

<210> SEQ ID NO 1
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uuuaaauuua aa                                                              12

<210> SEQ ID NO 2
<211> LENGTH: 85
<212> TYPE: RNA
<213> ORGANISM: Homo sapiens

<400> SEQUENCE: 2
ccuuagcaga gcuguggagu gugacaaugg uguuuguguc uaaacuauca aacgccauua          60
ucacacuaaa uagcuacugc uaggc                                                85

<210> SEQ ID NO 3
<211> LENGTH: 22
<212> TYPE: RNA
<213> ORGANISM: Homo sapiens

<400> SEQUENCE: 3
uggaguguga caauggucuu ug                                                   22

<210> SEQ ID NO 4
<211> LENGTH: 22
<212> TYPE: RNA
<213> ORGANISM: Homo sapiens

<400> SEQUENCE: 4
aacgccauua ucacacuaaa ua                                                   22

<210> SEQ ID NO 5
<211> LENGTH: 71
<212> TYPE: RNA
<213> ORGANISM: Homo sapiens

<400> SEQUENCE: 5
gccaacccag uguucagacu accuguucag gaggcucuca auguguacag uagucugcac          60
auugguuagg c                                                               71

<210> SEQ ID NO 6
<211> LENGTH: 23
<212> TYPE: RNA
<213> ORGANISM: Homo sapiens

<400> SEQUENCE: 6
cccaguguuc agacuaccug uuc                                                  23

<210> SEQ ID NO 7
<211> LENGTH: 22
<212> TYPE: RNA
<213> ORGANISM: Homo sapiens

<400> SEQUENCE: 7
acaguagucu gcacauuggu ua                                                   22

```
<210> SEQ ID NO 8
<211> LENGTH: 86
<212> TYPE: RNA
<213> ORGANISM: Homo sapiens

<400> SEQUENCE: 8
ugccagucuc uaggucccug agacccuuua accugugagg acauccaggg ucacagguga      60
gguucuuggg agccuggcgu cuggcc                                          86

<210> SEQ ID NO 9
<211> LENGTH: 24
<212> TYPE: RNA
<213> ORGANISM: Homo sapiens

<400> SEQUENCE: 9
ucccugagac ccuuuaaccu guga                                            24

<210> SEQ ID NO 10
<211> LENGTH: 22
<212> TYPE: RNA
<213> ORGANISM: Homo sapiens

<400> SEQUENCE: 10
acaggugagg uucuugggag cc                                              22

<210> SEQ ID NO 11
<211> LENGTH: 110
<212> TYPE: RNA
<213> ORGANISM: Homo sapiens

<400> SEQUENCE: 11
gccgagaccg agugcacagg gcucugaccu augaauugac agccagugcu cucgucuccc     60
cucuggcugc caauuccaua ggucacaggu auguucgccu caaugccagc                110

<210> SEQ ID NO 12
<211> LENGTH: 22
<212> TYPE: RNA
<213> ORGANISM: Homo sapiens

<400> SEQUENCE: 12
ucugaccuau gaauugacag cc                                              22

<210> SEQ ID NO 13
<211> LENGTH: 22
<212> TYPE: RNA
<213> ORGANISM: Homo sapiens

<400> SEQUENCE: 13
cugccaauuc cauaggucac ag                                              22

<210> SEQ ID NO 14
<211> LENGTH: 83
<212> TYPE: RNA
<213> ORGANISM: Homo sapiens

<400> SEQUENCE: 14
cggggugagg uaguagguug uggguuuca gggcagugau guugcccc uc ggaagauaac     60 uauacaaccu acugccuucc cug                                             83

<210> SEQ ID NO 15
<211> LENGTH: 22
```

```
<212> TYPE: RNA
<213> ORGANISM: Homo sapiens

<400> SEQUENCE: 15
ugagguagua gguugugugg uu                                              22

<210> SEQ ID NO 16
<211> LENGTH: 22
<212> TYPE: RNA
<213> ORGANISM: Homo sapiens

<400> SEQUENCE: 16
cuauacaacc uacugccuuc cc                                              22

<210> SEQ ID NO 17
<211> LENGTH: 64
<212> TYPE: RNA
<213> ORGANISM: Homo sapiens

<400> SEQUENCE: 17
ccccgcgacg agccccucgc acaaaccgga ccugagcguu uuguucguuc ggcucgcgug      60
aggc                                                                  64

<210> SEQ ID NO 18
<211> LENGTH: 23
<212> TYPE: RNA
<213> ORGANISM: Homo sapiens

<400> SEQUENCE: 18
gcgacgagcc ccucgcacaa acc                                             23

<210> SEQ ID NO 19
<211> LENGTH: 22
<212> TYPE: RNA
<213> ORGANISM: Homo sapiens

<400> SEQUENCE: 19
uuuguucguu cggcucgcgu ga                                              22

<210> SEQ ID NO 20
<211> LENGTH: 85
<212> TYPE: RNA
<213> ORGANISM: Homo sapiens

<400> SEQUENCE: 20
aggccucucu cuccguguuc acagcggacc uugauuuaaa uguccauaca auuaaggcac      60
gcggugaaug ccaagaaugg ggcug                                           85

<210> SEQ ID NO 21
<211> LENGTH: 22
<212> TYPE: RNA
<213> ORGANISM: Homo sapiens

<400> SEQUENCE: 21
cguguucaca gcggaccuug au                                              22

<210> SEQ ID NO 22
<211> LENGTH: 22
<212> TYPE: RNA
<213> ORGANISM: Homo sapiens

<400> SEQUENCE: 22
```

| | |
|---|---|
| uaaggcacgc ggugaaugcc aa | 22 |

<210> SEQ ID NO 23
<211> LENGTH: 106
<212> TYPE: RNA
<213> ORGANISM: Homo sapiens

<400> SEQUENCE: 23

| | |
|---|---|
| gcgcagcgcc cugucuccca gccugaggug cagugcugca ucucugguca guugggaguc | 60 |
| ugagaugaag cacuguagcu caggaagaga gaaguuguuc ugcagc | 106 |

<210> SEQ ID NO 24
<211> LENGTH: 22
<212> TYPE: RNA
<213> ORGANISM: Homo sapiens

<400> SEQUENCE: 24

| | |
|---|---|
| ggugcagugc ugcaucucug gu | 22 |

<210> SEQ ID NO 25
<211> LENGTH: 21
<212> TYPE: RNA
<213> ORGANISM: Homo sapiens

<400> SEQUENCE: 25

| | |
|---|---|
| ugagaugaag cacuguagcu c | 21 |

<210> SEQ ID NO 26
<211> LENGTH: 87
<212> TYPE: RNA
<213> ORGANISM: Homo sapiens

<400> SEQUENCE: 26

| | |
|---|---|
| gacagugcag ucacccauaa aguagaaagc acuacuaaca gcacuggagg guguaguguu | 60 |
| uccuacuuua uggaugagug uacugug | 87 |

<210> SEQ ID NO 27
<211> LENGTH: 21
<212> TYPE: RNA
<213> ORGANISM: Homo sapiens

<400> SEQUENCE: 27

| | |
|---|---|
| cauaaaguag aaagcacuac u | 21 |

<210> SEQ ID NO 28
<211> LENGTH: 23
<212> TYPE: RNA
<213> ORGANISM: Homo sapiens

<400> SEQUENCE: 28

| | |
|---|---|
| uguaguguuu ccuacuuuau gga | 23 |

<210> SEQ ID NO 29
<211> LENGTH: 110
<212> TYPE: RNA
<213> ORGANISM: Homo sapiens

<400> SEQUENCE: 29

| | |
|---|---|
| guguugggga cucgcgcgcu gguccagug guucuuaaca guucaacagu ucuguagcgc | 60 |
| aauugugaaa uguuuaggac cacuagaccc ggcgggcgcg gcgacagcga | 110 |

```
<210> SEQ ID NO 30
<211> LENGTH: 25
<212> TYPE: RNA
<213> ORGANISM: Homo sapiens

<400> SEQUENCE: 30
agugguucuu aacaguucaa caguu                                              25

<210> SEQ ID NO 31
<211> LENGTH: 22
<212> TYPE: RNA
<213> ORGANISM: Homo sapiens

<400> SEQUENCE: 31
gugaaauguu uaggaccacu ag                                                 22

<210> SEQ ID NO 32
<211> LENGTH: 80
<212> TYPE: RNA
<213> ORGANISM: Homo sapiens

<400> SEQUENCE: 32
ugggaugagg uaguagguug uauaguuuua gggucacacc caccacuggg agauaacuau        60
acaaucuacu gucuuccua                                                     80

<210> SEQ ID NO 33
<211> LENGTH: 22
<212> TYPE: RNA
<213> ORGANISM: Homo sapiens

<400> SEQUENCE: 33
ugagguagua gguuguauag uu                                                 22

<210> SEQ ID NO 34
<211> LENGTH: 21
<212> TYPE: RNA
<213> ORGANISM: Homo sapiens

<400> SEQUENCE: 34
cuauacaauc uacugucuuu c                                                  21

<210> SEQ ID NO 35
<211> LENGTH: 71
<212> TYPE: RNA
<213> ORGANISM: Homo sapiens

<400> SEQUENCE: 35
gcgacuguaa acauccucga cuggaagcug ugaagccaca gaugggcuuu cagucggaug        60
uuugcagcug c                                                             71

<210> SEQ ID NO 36
<211> LENGTH: 22
<212> TYPE: RNA
<213> ORGANISM: Homo sapiens

<400> SEQUENCE: 36
uguaaacauc cucgacugga ag                                                 22

<210> SEQ ID NO 37
<211> LENGTH: 22
<212> TYPE: RNA
<213> ORGANISM: Homo sapiens
```

```
<400> SEQUENCE: 37
cuuucagucg gauguuugca gc                                              22

<210> SEQ ID NO 38
<211> LENGTH: 71
<212> TYPE: RNA
<213> ORGANISM: Homo sapiens

<400> SEQUENCE: 38
ugggaaacau acuucuuuau augcccauau ggaccugcua agcuauggaa uguaagaag       60 uauguaucuc a                                                          71

<210> SEQ ID NO 39
<211> LENGTH: 22
<212> TYPE: RNA
<213> ORGANISM: Homo sapiens

<400> SEQUENCE: 39
acauacuucu uuauaugccc au                                              22

<210> SEQ ID NO 40
<211> LENGTH: 22
<212> TYPE: RNA
<213> ORGANISM: Homo sapiens

<400> SEQUENCE: 40
uggaauguaa agaaguaugu au                                              22

<210> SEQ ID NO 41
<211> LENGTH: 85
<212> TYPE: RNA
<213> ORGANISM: Homo sapiens

<400> SEQUENCE: 41
cgcuggcgac gggacauuau uacuuuuggu acgcgcugug acacuucaaa cucguaccgu      60
gaguaauaau gcgccgucca cggca                                           85

<210> SEQ ID NO 42
<211> LENGTH: 21
<212> TYPE: RNA
<213> ORGANISM: Homo sapiens

<400> SEQUENCE: 42
cauuauuacu uuugguacgc g                                               21

<210> SEQ ID NO 43
<211> LENGTH: 22
<212> TYPE: RNA
<213> ORGANISM: Homo sapiens

<400> SEQUENCE: 43
ucguaccgug aguaauaaug cg                                              22

<210> SEQ ID NO 44
<211> LENGTH: 22
<212> TYPE: RNA
<213> ORGANISM: Homo sapiens

<400> SEQUENCE: 44
caaacaccau ugucacacuc ca                                              22
```

```
<210> SEQ ID NO 45
<211> LENGTH: 22
<212> TYPE: RNA
<213> ORGANISM: Homo sapiens

<400> SEQUENCE: 45
uaaccaaugu gcagacuacu gu                                              22

<210> SEQ ID NO 46
<211> LENGTH: 24
<212> TYPE: RNA
<213> ORGANISM: Homo sapiens

<400> SEQUENCE: 46
ucacagguua aagggucuca ggga                                            24

<210> SEQ ID NO 47
<211> LENGTH: 22
<212> TYPE: RNA
<213> ORGANISM: Homo sapiens

<400> SEQUENCE: 47
ggcugucaau ucauagguca ga                                              22

<210> SEQ ID NO 48
<211> LENGTH: 22
<212> TYPE: RNA
<213> ORGANISM: Homo sapiens

<400> SEQUENCE: 48
aaccacacaa ccuacuaccu ca                                              22

<210> SEQ ID NO 49
<211> LENGTH: 22
<212> TYPE: RNA
<213> ORGANISM: Homo sapiens

<400> SEQUENCE: 49
ucacgcgagc cgaacgaaca aa                                              22

<210> SEQ ID NO 50
<211> LENGTH: 22
<212> TYPE: RNA
<213> ORGANISM: Homo sapiens

<400> SEQUENCE: 50
uuggcauuca ccgcgugccu ua                                              22

<210> SEQ ID NO 51
<211> LENGTH: 21
<212> TYPE: RNA
<213> ORGANISM: Homo sapiens

<400> SEQUENCE: 51
gagcuacagu gcuucaucuc a                                               21

<210> SEQ ID NO 52
<211> LENGTH: 23
<212> TYPE: RNA
<213> ORGANISM: Homo sapiens

<400> SEQUENCE: 52
uccauaaagu aggaaacacu aca                                             23
```

<210> SEQ ID NO 53
<211> LENGTH: 22
<212> TYPE: RNA
<213> ORGANISM: Homo sapiens

<400> SEQUENCE: 53
cuaguggucc uaaacauuuc ac                                              22

<210> SEQ ID NO 54
<211> LENGTH: 22
<212> TYPE: RNA
<213> ORGANISM: Homo sapiens

<400> SEQUENCE: 54
aacuauacaa ccuacuaccu ca                                              22

<210> SEQ ID NO 55
<211> LENGTH: 22
<212> TYPE: RNA
<213> ORGANISM: Homo sapiens

<400> SEQUENCE: 55
cuuccagucg aggauguuua ca                                              22

<210> SEQ ID NO 56
<211> LENGTH: 22
<212> TYPE: RNA
<213> ORGANISM: Homo sapiens

<400> SEQUENCE: 56
auacauacuu cuuuacauuc ca                                              22

<210> SEQ ID NO 57
<211> LENGTH: 22
<212> TYPE: RNA
<213> ORGANISM: Homo sapiens

<400> SEQUENCE: 57
cgcauuauua cucacgguac ga                                              22

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccccgctgga actactatga                                                 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tcggtgctcc aggataaact                                                 20

<210> SEQ ID NO 60
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cccacacaca tgcacttacc                                                  20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61 cccaccccectt ctctaagtcc                                                20

<210> SEQ ID NO 62
<211> LENGTH: 1705
<212> TYPE: RNA
<213> ORGANISM: Homo sapiens

<400> SEQUENCE: 62
```

| | | | | | |
|---|---|---|---|---|---|
| augugucacc | agcaguuggu | caucucuugg | uuuucccugg | uuuuucuggc | aucucccuc    60 |
| guggccauau | gggaacugaa | gaaagaugu  | uaugucguag | aauggauug  | guauccggau  120 |
| gccccuggag | aaauggugu  | ccucaccugu | gacaccccug | aagaagaugg | uauccaccugg 180 |
| accuuggacc | agagcaguga | ggucuuaggc | ucuggcaaaa | cccugaccau | ccaagucaaa  240 |
| gaguuuggag | augcuggcca | guacaccugu | cacaaaggag | gcgagguucu | aagccauucg  300 |
| cuccugcugc | uucacaaaaa | ggaagaugga | auuuggucca | cugauauuuu | aaaggaccag  360 |
| aaagaaccca | aaauaagac  | cuuucuaaga | ugcgaggcca | agaauuauuc | uggacguuuc  420 |
| accugcuggu | ggcugacgac | aaucaguacu | gauuugacau | ucagugucaa | aagcagcaga  480 |
| ggcucuucug | accccccaagg | ggugacgugc | ggagcugcua | cacucucugc | agagagaguc  540 |
| agagggggaca | acaaggagua | ugaguacuca | gugggagugcc | aggaggacag | ugccugccca  600 |
| gcugcugagg | agagucugcc | cauugagguc | augguggaug | ccguucacaa | gcucaaguau  660 |
| gaaaacuaca | ccagcagcuu | cuucaucagg | gacaucauca | aaccgaccc  | acccaagaac  720 |
| uugcagcuga | agccauuaaa | gaauucucgg | caggugggagg | ucagcuggga | guacccugac  780 |
| accuggagua | cuccacauuc | cuacuucucc | cugacauucu | gcguucaggu | ccagggcaag  840 |
| agcaagagag | aaaagaaaga | uagagucuuc | acggacaaga | ccucagccac | ggucaucugc  900 |
| cgcaaaaaug | ccagcauuag | cgugcgggcc | caggaccgcu | acauauagcuc | aucuuggagc  960 |
| gaaugggcau | cugugcccug | cagguggugc | ggugcggcg  | gaucuagaaa | ccucccccgug 1020 |
| gccacuccag | acccaggaau | guucccaugc | cuucaccacu | cccaaaaccu | gcuggggggcc 1080 |
| gucagcaaca | ugcuccagaa | ggccagacaa | acucuagaau | uuuacccuug | cacuucugaa  1140 |
| gagauugauc | augaagauau | cacaaaagau | aaaaccagca | caguggaggc | cuguuuacca  1200 |
| uuggaauuaa | ccaagaauga | gaguugccua | aauuccagag | accucuuu   | cauaacuaau  1260 |
| gggaguugcc | uggccuccag | aaagaccucu | uuuaugaugg | cccugugccu | uagauaguu   1320 |
| uaugaagacu | ugaagaugua | ccagguggag | uucaagacca | ugaaugcaaa | gcuucugaug  1380 |
| gauccuaaga | ggcagaucuu | ucuagaucaa | aacaugcugg | caguuauuga | ugagcugaug  1440 |

| caggcccuga auuucaacag ugagacugug ccacaaaaau ccucccuuga agaaccggau | 1500 |
| uuuuauaaaa cuaaaaucaa gcucugcaua cuucuucaug cuuucagaau ucgggcagug | 1560 |
| acuauugaua gagugaugag cuaucugaau gcuuccuaac aaacaccauu gucacacucc | 1620 |
| auuuaaaaua cauacuucuu uacauuccau uuaaacuagu gguccuaaac auuucacuuu | 1680 |
| aaacuuccag ucgaggaugu uuaca | 1705 |

<210> SEQ ID NO 63
<211> LENGTH: 1599
<212> TYPE: RNA
<213> ORGANISM: Homo sapiens

<400> SEQUENCE: 63

| augugucacc agcaguuggu caucucuugg uuucccugg uuuucuggc aucucccuc | 60 |
| guggccauau gggaacugaa gaaagauguu uaugucguag aauuggauug guauccggau | 120 |
| gccccuggag aaaugguggu ccucaccugu gacaccccug aagaauggu uaucaccugg | 180 |
| accuggacc agagcaguga ggucuuaggc ucuggcaaaa cccugaccau ccaagucaaa | 240 |
| gaguuuggag augcuggcca guacaccugu cacaaaggag gcgagguucu aagccauucg | 300 |
| cuccugcugc uucacaaaaa ggaagaugga auuuggucca cugauauuuu aaaggaccag | 360 |
| aaagaaccca aaauaagac cuuucuaaga ugcgaggcca agaauuauuc uggacguuuc | 420 |
| accgcuggu ggcugacgac aaucaguacu gauuugacau ucagugucaa aagcagcaga | 480 |
| ggcucuucug accccaagg ggugacgugc ggagcugcua cacucucugc agagagaguc | 540 |
| agagggggaca caaggagua ugaguacuca guggagugcc aggaggacag ugccugccca | 600 |
| gcugcugagg agagucugcc cauugagguc augguggaug ccguucacaa gcucaaguau | 660 |
| gaaaacuaca ccagcagcuu cuucaucagg gacaucauca aaccugaccc acccaagaac | 720 |
| uugcagcuga agccauuaaa gaauucucgg caggugagg ucagcuggga uacccugac | 780 |
| accuggagua cuccacauuc cuacuucucc cugacauucu gcguucaggu ccagggcaag | 840 |
| agcaagagag aaaagaaaga uagagucuuc acggacaaga ccucagccac ggucaucugc | 900 |
| cgcaaaaaug ccagcauuag cgugcgggcc caggaccgcu acauagcuc aucuuggagc | 960 |
| gaaugggcau cugugcccug cagugguggc ggugcggcg gaucuagaaa ccuccccgug | 1020 |
| gccacuccag acccaggaau guucccaugc cuucaccacu cccaaaaccu gcugagggcc | 1080 |
| gucagcaaca ugcuccagaa ggccagacaa acucuagaau uuacccuug cacuucugaa | 1140 |
| gagauugauc augaagauau cacaaaagau aaaaccagca cagugaggc cuguuuacca | 1200 |
| uuggaauuaa ccaagaauga gaguugccua aauuccagag agaccucuuu cauaacuaau | 1260 |
| gggaguugcc uggccuccag aaagaccucu uuuaugaugg cccugugccu uaguaguauu | 1320 |
| uaugaagacu ugaagaugua ccagguggag uucaagacca ugaaugcaaa gcuucugaug | 1380 |
| gauccuaaga ggcagaucuu ucuagaucaa aacaugcugg caguuauuga ugagcugaug | 1440 |
| caggcccuga auucaacag ugagacugug ccacaaaaau ccucccuuga agaaccggau | 1500 |
| uuuuauaaaa cuaaaaucaa gcucugcaua cuucuucaug cuuucagaau ucgggcagug | 1560 |
| acuauugaua gagugaugag cuaucugaau gcuuccuaa | 1599 |

<210> SEQ ID NO 64
<211> LENGTH: 541
<212> TYPE: RNA
<213> ORGANISM: Homo sapiens

<400> SEQUENCE: 64

```
auguggcugc agagccugcu gcucuuggc acuguggccu gcagcaucuc ugcacccgcc        60
cgcucgccca gccccagcac gcagcccugg gagcauguga augccaucca ggaggcccgg       120
cgucuccuga accugaguag agacacugcu gcugagauga augaaacagu agaagucauc       180
ucagaaaugu uugaccucca ggagccgacc ugccuacaga cccgccugga gcuguacaag       240
cagggccugc ggggcagccu caccaagcuc aagggcsccu ugaccaugau ggccagccac       300
uacaagcagc acugcccucc aacccggaa acuuccugug caacccagau uaucaccuuu       360
gaaaguuuca aagagaaccu gaaggacuuu cugcuuguca uccccuuuga cugcugggag       420
ccaguccagg agugacaaac accauugnca cacuccauuu aaaauacaua cuucuuuaca       480
uuccauuuaa acuaguggc cuaaacauuu cacuuuaaac uuccagucga ggauguuuac       540
a                                                                       541

<210> SEQ ID NO 65
<211> LENGTH: 435
<212> TYPE: RNA
<213> ORGANISM: Homo sapiens

<400> SEQUENCE: 65
auguggcugc agagccugcu gcucuuggc acuguggccu gcagcaucuc ugcacccgcc        60
cgcucgccca gccccagcac gcagcccugg gagcauguga augccaucca ggaggcccgg       120
cgucuccuga accugaguag agacacugcu gcugagauga augaaacagu agaagucauc       180
ucagaaaugu uugaccucca ggagccgacc ugccuacaga cccgccugga gcuguacaag       240
cagggccugc ggggcagccu caccaagcuc aagggcsccu ugaccaugau ggccagccac       300
uacaagcagc acugcccucc aacccggaa acuuccugug caacccagau uaucaccuuu       360
gaaaguuuca aagagaaccu gaaggacuuu cugcuuguca uccccuuuga cugcugggag       420
ccaguccagg aguga                                                        435
```

COMPOSITIONS AND METHODS FOR ORGAN-PROTECTIVE EXPRESSION AND MODULATION OF CODING RIBONUCLEIC ACIDS

CROSS-REFERENCE TO RELATED APPLICATIONS

This application is a continuation application of International Application No. PCT/US2021/019028 filed Feb. 22, 2021, now pending; which claims the benefit under 35 USC § 119(e) to U.S. Application Ser. No. 63/059,458 filed Jul. 31, 2020 and to U.S. Application Ser. No. 62/979,619 filed Feb. 21, 2020. The disclosure of each of the prior applications is considered part of and is incorporated by reference in the disclosure of this application.

INCORPORATION BY REFERENCE OF SEQUENCE LISTING

The material in the accompanying sequence listing is hereby incorporated by reference into this application. The accompanying sequence listing text file, named CTX1100-2_ST25.txt, was created on Mar. 3, 2022 and is 17 kB in size. The file can be accessed using Microsoft Word on a computer that uses Windows OS.

BACKGROUND OF THE INVENTION

Field of the Invention

The present invention relates to messenger ribonucleic acid (mRNA) delivery technologies, and methods of using these mRNA delivery technologies in a variety of therapeutic, diagnostic and prophylactic indications. Such delivery systems may be used as stand-alone interventions, or in combination with other therapeutic components.

Background Information

The ability to induce expression of a specified gene product such as a polypeptide in a particular target tissue or organ is frequently desired. In many situations, a target tissue or organ, will comprise more than one type of cell, and in such cases it is also frequently desired to express the gene product to different degrees in the different cell types—that is, to provide differential expression of the gene product between the different cell types in the target tissue. For example, in gene therapy a mutated and/or functionless gene can be replaced in target cells by an intact copy, but it is also useful to minimise off target protein production in neighbouring cells, tissues and organs. Likewise, a gene product for vaccine antigens such as the spike protein for COVID-19 is preferably expressed in or around dendritic cells of the immune system in order to ensure a maximal response.

Gene therapy often relies on viral vectors to introduce coding polynucleotides into target cells, but other techniques exist to deliver polynucleotides to cells without the use of viruses. The advantages of viruses include relatively high possible transfection rates, as well as the ability to target the virus to particular cell types by control of the binding proteins by which viruses enter a target cell. In contrast, non-viral methods of introducing coding polynucleotides into cells can have problems with low transfection rates, as well as having limited options for targeting expression to particular organs and cell types. However, the nature of viral intervention carries risks of toxicity and inflammation, but also has limited control over the duration and degree of the expression of the introduced factor.

Tumor therapies based upon biological approaches have advantages over traditional chemotherapeutics because they can employ numerous diverse mechanisms to target and destroy cancers more precisely—e.g., via direct cell lysis, cytotoxic immune effector mechanisms and vascular collapse amongst others. As a result, there has been a significant increase in the number of clinical studies into the potential of such approaches. However due to the diverse range of therapeutic activities, pre-clinical and clinical study is complex, as multiple parameters may affect their therapeutic potential and, hence, defining reasons for treatment failure or methodologies that might enhance the therapeutic activity can be difficult. Maintaining on-target activities, tumor specificity and reducing side effects is also a major challenge for such experimental and powerful therapies.

Viral based therapies have emerged as a promising approach to address many aspects of disease treatment. Oncolytic viruses and cancer vaccines that are based upon inactivated or attenuated viruses offer considerable potential for hard-to-treat cancers. However, the effectiveness of therapeutic viruses is often thwarted by the body's own immune response thereby limiting applications to avoid systemic administration. Hence, it would be advantageous to provide novel compositions and methods that are able to improve and enhance the range of therapeutic viral approaches currently available.

WO-2017/132552-A1 describes recombinant oncolytic virus with an engineered genome that includes micro-RNA binding sites.

US-2013/156849-A1 relates to methods for expressing a polypeptide of interest in a mammalian cell or tissue, the method comprising, contacting said mammalian cell or tissue with a formulation comprising a modified mRNA encoding the polypeptide of interest. WO-2016/011306-A2 describes design, preparation, manufacture and/or formulation of nucleic acids comprising at least one terminal modification that may comprise a micro-RNA binding site. The aforementioned prior art do not address the problems of ensuring effective protection of single or multiple organ types in the body of a subject who is treated with a co-administered therapeutic agent or factor.

WO 2019/051100 A1 and WO 2019/158955 A1 describe compositions and methods for delivery of mRNA sequences for expression of one or more polypeptides within one or more target organs, comprising miRNA binding site sequences which allow for differential expression of the coding sequence in at least a first and a second cell type within the target organ or organs.

There is a need to further develop further improved and optimized methods and compositions for modulating expression of polynucleotide sequences, such as mRNA, in specific organs and/or tissues.

SUMMARY OF THE INVENTION

In a first aspect the invention provides an mRNA construct comprising at least one open reading frame (ORF), wherein the ORF is operatively linked to at least one untranslated region (UTR), wherein the UTR comprises at least one organ protection sequence (OPS), wherein the OPS sequence comprises at least a first, a second and a third micro-RNA (miRNA) target sequence, and wherein each of at least a first, second and third the miRNA target sequences are optimised to hybridise with a corresponding miRNA sequence.

A second aspect of the invention provides a pharmaceutical composition comprising:
  i. an mRNA construct comprising at least one open reading frame (ORF), wherein the ORF is operatively linked to at least one untranslated region (UTR), wherein the UTR comprises at least one organ protection sequence (OPS), wherein the OPS sequence comprises at least a first, a second and a third micro-RNA (miRNA) target sequence, and wherein each of the at least a first, second and third miRNA target sequences are optimised to hybridise with a corresponding miRNA sequence; and
  ii. an in vivo delivery composition;
  wherein the mRNA construct is comprised within or adsorbed to the delivery composition.

A third aspect of the invention provides an mRNA construct comprising at least one open reading frame (ORF), wherein the ORF is operatively linked to at least one untranslated region (UTR), wherein the UTR comprises at least one organ protection sequence (OPS), wherein the OPS sequence protects multiple organs, and wherein the OPS comprises at least a first, and at least a second micro-RNA (miRNA) target sequence, and wherein each of the at least a first and second miRNA target sequences are optimised to hybridise with a corresponding miRNA sequence.

A fourth aspect of the invention provides a pharmaceutical composition comprising:
  a. at least one mRNA construct comprising at least one open reading frame (ORF), wherein the ORF is operatively linked to at least one untranslated region (UTR), wherein the UTR comprises at least one organ protection sequence (OPS), wherein the OPS sequence protects multiple organs, and wherein the OPS sequence comprises at least a first and a second micro-RNA (miRNA) target sequence, and wherein each of the at least a first and second miRNA target sequences are optimised to hybridise with a corresponding miRNA sequence; and
  b. an in vivo delivery composition;
  wherein the mRNA construct is comprised within or adsorbed to the delivery composition.

A fifth aspect of the invention provides pharmaceutical composition comprising:
  a. at least one mRNA construct comprising at least one open reading frame (ORF), wherein the ORF is operatively linked to at least one untranslated region (UTR), wherein the UTR comprises at least one organ protection sequence (OPS), wherein the OPS sequence protects multiple organs, and wherein the OPS sequence comprises at least a first and a second micro-RNA (miRNA) target sequence, and wherein each of the at least a first and second miRNA target sequences are optimised to hybridise with a corresponding miRNA sequence; and
  b. an in vivo delivery composition;
  wherein the mRNA construct is comprised within or adsorbed to the delivery composition.

A sixth aspect provides for an mRNA comprising at least one open reading frame (ORF), wherein the ORF is operatively linked to at least one untranslated region (UTR), wherein the UTR comprises at least one organ protection (OPS) sequence, and wherein the OPS sequence comprises:
  a. at least a first OPS, wherein the first OPS comprises a sequence that is a target for a first miRNA, and wherein the first OPS is optimised to hybridise to the first miRNA with a substantially perfect match within cells of a first organ;
  b. at least a second OPS, wherein the second OPS comprises a sequence that is a target for a second miRNA, and wherein the second OPS is optimised to hybridise to the second miRNA with a substantially perfect match within cells of a second organ; and
  c. at least a third OPS, wherein the third OPS comprises a sequence that is a target for a third miRNA, and wherein the third OPS is optimised to hybridise to the third miRNA with a substantially perfect match within cells of a third organ;
  wherein the first, second and third organ protection sequences are arranged consecutively within the OPS and wherein the cells of the first, second and third organs are non-diseased cells.

A seventh aspect of the invention provides for a pharmaceutical composition comprising:
  i. at least one mRNA as described herein; and
  ii. an in vivo delivery composition;
  wherein the mRNA construct is comprised within or adsorbed to the delivery composition.

An eighth aspect of the invention provides a vaccine composition comprising:
  at least a first mRNA construct comprising at least one open reading frame (ORF), wherein the ORF is operatively linked to at least one untranslated region (UTR), wherein the UTR comprises at least one organ protection sequence (OPS), wherein the OPS sequence protects multiple organs, and wherein the OPS sequence comprises at least a first and a second micro-RNA (miRNA) target sequence, and wherein each of the at least a first and second miRNA target sequences are optimised to hybridise with a corresponding miRNA sequence; and an in vivo delivery composition;

wherein the mRNA construct is comprised within or adsorbed to the delivery composition.

A ninth aspect of the invention provides a vaccine composition comprising:

a vaccine construct comprising at least a first mRNA having at least a first open reading frame (ORF), wherein the first ORF encodes an antigen selected from: a bacterial protein; and/or a viral protein, and wherein the first ORF is operatively linked to at least one untranslated region (UTR), wherein the UTR comprises at least one organ protection sequence (OPS), wherein the OPS sequence protects multiple organs, and wherein the OPS sequence comprises at least a first and a second micro-RNA (miRNA) target sequence, and wherein each of the at least a first and second miRNA target sequences are optimised to hybridise with a corresponding miRNA sequence;

an adjuvant construct comprising at least a second mRNA comprising at least a second open reading frame (ORF), wherein the second ORF encodes a proinflammatory cytokine selected from: IFNγ; IFNα; IFNβ; TNFα; IL-12; IL-2; IL-6; IL-8; and GM-CSF, and wherein the second ORF is operatively linked to at least one untranslated region (UTR), wherein the UTR comprises at least one OPS sequence that protects multiple organs, and wherein the OPS sequence comprises at least a third and a fourth miRNA target sequence, and wherein each of the at least a third and fourth miRNA target sequences are optimised to hybridise with a corresponding miRNA sequence;
and
an in vivo delivery composition;
wherein the vaccine and adjuvant constructs are comprised within or adsorbed to the delivery composition. Alternatively, the vaccine and adjuvant constructs may be comprised within or adsorbed to different delivery compositions that are co-administered, or administered sequentially.

The invention is further exemplified in a variety of embodiments and examples described herein, the features of which may be further combined to form additional embodiments as would be understood by the skilled addressee.

BRIEF DESCRIPTION OF THE DRAWINGS

FIG. 5A shows mCherry signal in normal human kidney cells transfected with compositions as described herein, showing a reduction in signal in the mCherry-3MOP treated cells, indicating a reduction in mCherry translation. The images are superimposition of images acquired with Texas Red and DAPI filter cubes, showing mCherry fluorescence signal and cell nuclei staining.

FIG. 5B shows quantification of mCherry fluorescence in the transfected normal human kidney cells using a Cytation instrument (Biotek).

FIGS. 6A-6F show comparison of mCherry signal in liver cells transfected with composition as described herein that comprise a perfect matched MOP sequence that binds miRNA-122, miRNA-192, and miRNA-30a, and demonstrates that the MOP sequence suppresses expression in AML12 murine hepatocytes but not in liver cancer cells (Hep3B). For each set of pictures, the top panel is a superimposition of images acquired with the Texas Red and DAPI filter cubes, showing cell nuclei staining and mCherry fluorescence. The bottom panel represents an image acquired with the Texas Red filter cube and shows the mCherry fluorescence only. (FIG. 6A) The top panel shows control Hep3B cells (liver cancer) that are not transfected with mRNA, the bottom panel shows no mCherry signal, (FIG. 6B) Cell nuclei staining and mCherry signal in Hep3B cells transfected with mRNA without a MOP sequence, (FIG. 6C) Cell nuclei staining and mCherry signal in Hep3B cells transfected with mRNA with the MOP sequence, (FIG. 6D) Cell nuclei staining in control AML12 cells (normal liver) that are not transfected with mRNA, the bottom panel shows no mCherry signal, (FIG. 6E) Cell nuclei staining and mCherry signal in AML12 cells transfected with mRNA without a MOP sequence, (FIG. 6F) Cell nuclei staining and mCherry signal in AML12 cells transfected with mRNA with the MOP sequence.

FIGS. 7A-7F show comparison of mCherry signal in liver cells transfected with composition as described herein that comprise a perfect matched MOP sequence that binds Let7b, miRNA-126, and miRNA-30a, and demonstrates that the MOP sequence suppresses expression in AML12 murine hepatocytes but not in liver cancer cells (Hep3B). For each set of pictures, the top panel is a superimposition of images acquired with the Texas Red and DAPI filter cubes, showing cell nuclei staining and mCherry fluorescence. The bottom panel represents an image acquired with the Texas Red filter cube and shows the mCherry fluorescence only. (FIG. 7A) The top panel shows control Hep3B cells (liver cancer) that are not transfected with mRNA, the bottom panel shows no mCherry signal, (FIG. 7B) Cell nuclei staining and mCherry signal in Hep3B cells transfected with mRNA without a MOP sequence, (FIG. 7C) Cell nuclei staining and mCherry signal in Hep3B cells transfected with mRNA with the MOP sequence (FIG. 7D) Cell nuclei staining in control AML12 cells (normal liver) that are not transfected with mRNA, the bottom panel shows no mCherry signal, (FIG. 7E) Cell nuclei staining and mCherry signal in AML12 cells transfected with mRNA without a MOP sequence, (FIG. 7F) Cell nuclei staining and mCherry signal in AML12 cells transfected with mRNA with the MOP sequence.

(FIG. 9A) the top panel shows cell nuclei staining in control AML12 cells (normal liver) that are not transfected with mRNA, and the bottom panel shows no mCherry signal, (FIG. 9B) Cell nuclei staining and mCherry signal in AML12 cells transfected with mRNA without a MOP sequence, (FIG. 9C) Cell nuclei staining and mCherry signal in AML12 cells transfected with mRNA with the 2* unperfect matched miRNA122 MOP sequence (nonoptimized), the bottom panel showing that there is detectable expression of mCherry in the AML12 cells, (FIG. 9D) Cell nuclei staining and mCherry signal in AML12 cells transfected with mRNA with the 2* perfect matched miRNA-122 MOP binding sequence (optimized), the bottom panel showing that there is almost no detectable expression of mCherry in the AML12 cells.

FIGS. 10A-10F show comparison of mCherry signal in kidney cells transfected with compositions as described herein that comprise a perfect matched MOP sequence that binds to Let7b, miRNA-126, and miRNA-30a, and demonstrates that the MOP sequence suppresses mCherry expression in human kidney cells (hREC) but not in cancer cells (786-0). For each of (FIG. 10A), (FIG. 10B), (FIG. 10C), (FIG. 10D), (FIG. 10E) and (FIG. 10F), the top panel is a superimposition of images acquired with the Texas Red and DAPI filter cubes, showing cell nuclei staining and mCherry fluorescence. The bottom panel represents an image acquired with the Texas Red filter cube and shows the mCherry fluorescence only. (FIG. 10A) the top panel shows cell nuclei staining in control 786-0 human renal cell adenocarcinoma cells that are not transfected with mRNA, the bottom panel shows no mCherry signal, (FIG. 10B) cell nuclei staining and mCherry signal in 786-0 cells transfected with mRNA without a MOP sequence, (FIG. 10C) cell nuclei and mCherry signal in 786-0 cells transfected with mRNA with the MOP sequence, which shows evidence of expression, (FIG. 10D) cell nuclei staining in control hREC cells (normal mixed kidney epithelial cells) that are not transfected with mRNA, the bottom panel shows no mCherry signal, (FIG. 10E) cell nuclei staining and mCherry signal in hREC cells transfected with mRNA without a MOP sequence, (FIG. 10F) cell nuclei staining and mCherry signal in hREC cells transfected with mRNA with the MOP sequence, the mCherry signal alone showing virtually no expression.

FIGS. 11A-11F show comparison of mCherry signal in kidney cells transfected with compositions as described herein that comprise a perfect matched MOP sequence that binds to miRNA-122, miRNA-192, and miRNA-30a, and demonstrates that the MOP sequence suppresses mCherry expression in human kidney cells (hREC) but not in cancer cells (786-0). For each of (FIG. 11A), (FIG. 11B), (FIG. 11C), (FIG. 11D), (FIG. 11E) and (FIG. 11F), the top panel is a superimposition of images acquired with the Texas Red and DAPI filter cubes, showing cell nuclei staining and mCherry fluorescence. The bottom panel represents an image acquired with the Texas Red filter cube and shows the mCherry fluorescence only. (FIG. 11A) the top panel shows cell nuclei staining in control 786-0 human renal cell adenocarcinoma cells that are not transfected with mRNA, the bottom panel shows no mCherry signal, (FIG. 11B) cell nuclei staining and mCherry signal in 786-0 cells transfected with mRNA without a MOP sequence, (FIG. 11C) cell nuclei and mCherry signal in 786-0 cells transfected with mRNA with the MOP sequence, which shows evidence of expression, (FIG. 11D) cell nuclei staining in control hREC cells (normal mixed kidney epithelial cells) that are not transfected with mRNA, the bottom panel shows no mCherry signal, (FIG. 11E) cell nuclei staining and mCherry signal in hREC cells transfected with mRNA without a MOP sequence, (FIG. 11F) cell nuclei staining and mCherry signal in hREC cells transfected with mRNA with the MOP sequence, the mCherry signal alone showing virtually no expression.

FIGS. 12A-12B show results of an experiment according to one embodiment in which human PBMC cells have been transfected with compositions as described herein that comprise (a) mRNA that expresses human IL-12 at three levels of dosage, expression of IL-12 is recorded six hours after transfection with the following mRNAs: NC (noncoding human recombinant IL-12 from a single chain—no ATG codon), hdcIL-12 (human recombinant IL-12 from a 1:1 mixture of separate IL12A and IL12B mRNAs), hscIL-12 (human recombinant IL-12 from a single chain), and hscIL-12-MOP (human recombinant IL-12 from a single chain), which is an single chain recombinant IL-12 expressing mRNA comprising a perfect matched MOP sequence that binds to miRNA-122-miRNA-203a-miRNA-1-miRNA-30a; (b) mRNA that expresses human GM-CSF at three levels of dosage, expression of GM-CSF is recorded six hours after transfection with the following mRNAs: NC (noncoding GM-CSF mRNA—no ATG codon), hGM-CSF, and hGM-CSF-MOP, which is an hGM-CSF expressing mRNA comprising a perfect matched MOP sequence that binds to miRNA-122-miRNA-203a-miRNA-1-miRNA-30a.

FIGS. 13A-13F show comparison of mCherry signal in colon epithelial cells transfected with composition as described herein that comprise a perfect matched MOP sequence that binds miRNA-122, miRNA-192, and miRNA-30a, and demonstrates that the MOP sequence suppresses expression in colon epithelial cells but not in colon cancer cells (HCT-116). For each set of pictures, the top panel is a superimposition of images acquired with the Texas Red and DAPI filter cubes, showing cell nuclei staining and mCherry fluorescence. The bottom panel represents an image acquired with the Texas Red filter cube and shows the mCherry fluorescence only. (FIG. 13A) The top panel shows control colon epithelial cells that are not transfected with mRNA, the bottom panel shows no mCherry signal, (FIG. 13B) Cell nuclei staining and mCherry signal in colon cells transfected with mRNA without a MOP sequence, (FIG. 13C) Cell nuclei staining and mCherry signal in colon cells transfected with mRNA with the MOP sequence (FIG. 13D) Cell nuclei staining in control HCT-116 cells (colon cancer) that are not transfected with mRNA, the bottom panel shows no mCherry signal, (FIG. 13E) Cell nuclei staining and mCherry signal in HCT-116 cells transfected with mRNA without a MOP sequence, (f) Cell nuclei staining and mCherry signal in HCT-116 cells transfected with mRNA with the MOP sequence.

FIGS. 14A-14F show comparison of mCherry signal in colon epithelial cells transfected with composition as described herein that comprise a perfect matched MOP sequence that binds miRNA-Let7b, miRNA-126, and miRNA-30a, and demonstrates that the MOP sequence provides organ protection by suppressing expression in both normal colon cells and colon cancer cells, attributed to presence of miRNA-Let7b binding site. For each set of pictures, the top panel is a superimposition of images acquired with the Texas Red and DAPI filter cubes, showing cell nuclei staining and mCherry fluorescence. The bottom panel represents an image acquired with the Texas Red filter cube and shows the mCherry fluorescence only. (FIG. 14A) The top panel shows control colon epithelial cells that are not transfected with mRNA, the bottom panel shows no mCherry signal, (FIG. 14B) Cell nuclei staining and mCherry signal in colon cells transfected with mRNA without a MOP sequence, (FIG. 14C) Cell nuclei staining and mCherry signal in colon cells transfected with mRNA with the MOP sequence (FIG. 14D) Cell nuclei staining in control HCT-116 cells (colon cancer) that are not transfected with mRNA, the bottom panel shows no mCherry signal, (FIG. 14E) Cell nuclei staining and mCherry signal in HCT-116 cells transfected with mRNA without a MOP sequence, (0 Cell nuclei staining and mCherry signal in HCT-116 cells transfected with mRNA with the MOP sequence.

FIGS. 15A-15C show mCherry signal in normal healthy lung cells (BEAS-2B) transfected with composition as described herein that comprise a perfect matched MOP sequence that binds miRNA-Let7b, miRNA-126, and miRNA-30a, and demonstrates that the MOP sequence provides organ protection for the lung by suppressing expression in healthy lung cells, attributed to presence of miRNA-Let7b binding site. For each set of pictures, the top panel is a superimposition of images acquired with the Texas Red and DAPI filter cubes, showing cell nuclei staining and mCherry fluorescence. The bottom panel represents an image acquired with the Texas Red filter cube and shows the mCherry fluorescence only. (FIG. 15A) The top panel shows control cells that are not transfected with mRNA, the bottom panel shows no mCherry signal, (FIG. 15B) Cell nuclei staining and mCherry signal in cells transfected with mRNA without a MOP sequence, (FIG. 15C) Cell nuclei staining and mCherry signal in lung cells transfected with mRNA with the MOP sequence.

DETAILED DESCRIPTION OF THE INVENTION

Figure 1:
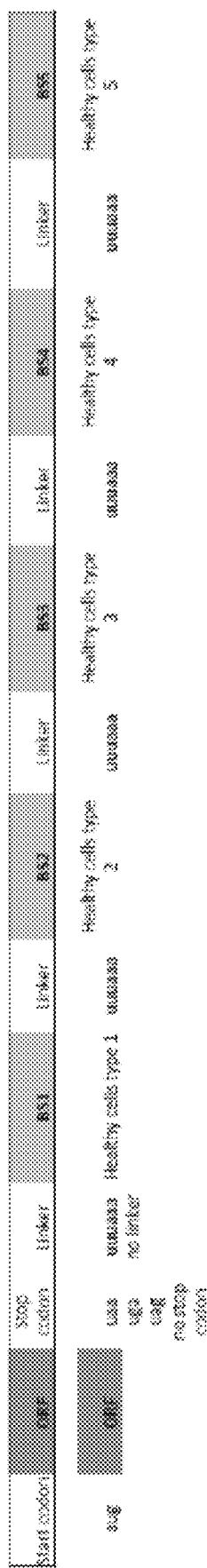
FIG. 1 shows schematic view (i.e., not to scale) of an mRNA construct incorporating an OPS according to an embodiment of the invention.

Unless otherwise indicated, the practice of the present invention employs conventional techniques of chemistry, molecular biology, microbiology, recombinant DNA technology, and chemical methods, which are within the capabilities of a person of ordinary skill in the art. Such techniques are also explained in the literature, for example, M. R. Green, J. Sambrook, 2012, Molecular Cloning: A Laboratory Manual, Fourth Edition, Books 1-3, Cold Spring Harbor Laboratory Press, Cold Spring Harbor, N.Y.; Ausubel, F. M. et al. (Current Protocols in Molecular Biology, John Wiley & Sons, Online ISSN: 1934-3647); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press; Synthetic Biology, Part A, Methods in Enzymology, Edited by Chris Voigt, Volume 497, Pages 2-662 (2011); Synthetic Biology, Part B, Computer Aided Design and DNA Assembly, Methods in Enzymology, Edited by Christopher Voigt, Volume 498, Pages 2-500 (2011); RNA Interference, Methods in Enzymology, David R. Engelke, and John J. Rossi, Volume 392, Pages 1-454 (2005). Each of these general texts is herein incorporated by reference.

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

As used herein, the term 'comprising' means any of the recited elements are necessarily included and other elements may optionally be included as well. 'Consisting essentially of' means any recited elements are necessarily included, elements that would materially affect the basic and novel characteristics of the listed elements are excluded, and other elements may optionally be included. 'Consisting of' means that all elements other than those listed are excluded. Embodiments defined by each of these terms are within the scope of this invention.

The term 'isolated', when applied to a polynucleotide sequence, denotes that the sequence has been removed from its natural organism of origin and is, thus, free of extraneous or unwanted coding or regulatory sequences. The isolated sequence is suitable for use in recombinant DNA processes and within genetically engineered protein synthesis systems. Such isolated sequences include cDNAs, mRNAs and genomic clones. The isolated sequences may be limited to a protein encoding sequence only or can also include 5' and 3' regulatory sequences such as promoters and transcriptional terminators, or untranslated sequences (UTRs). Prior to further setting forth the invention, a number of definitions are provided that will assist in the understanding of the invention.

A 'polynucleotide' is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Polynucleotides include DNA and RNA, and may be manufactured synthetically in vitro or isolated from natural sources. Sizes of polynucleotides are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 40 nucleotides in length are typically called 'oligonucleotides'. The term 'nucleic acid sequence' as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acid sequences may include DNA and RNA, and may be manufactured synthetically in vitro or isolated from natural sources. In specific embodiments of the present invention the nucleic acid sequence comprises messenger RNA (mRNA).

Nucleic acids may further include modified DNA or RNA, for example DNA or RNA that has been methylated, or RNA that has been subject to post-translational modification, for example 5'-capping with 7-methylguanosine, 3'-processing such as cleavage and polyadenylation, and splicing. Nucleic acids may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA).

According to the present invention, homology to the nucleic acid sequences described herein is not limited simply to 100% sequence identity. In this regard, the term "substantially similar", relating to two sequences, means that the sequences have at least 70%, 80%, 90%, 95% or 100% similarity. Likewise, the term "substantially complementary", relating to two sequences, means that the sequences are completely complementary, or that at least 70%, 80%, 90%, 95% or 99% of the bases are complementary. That is, mismatches can occur between the bases of the sequences which are intended to hybridise, which can occur between at least 1%, 5%, 10%, 20% or up to 30% of the bases. However, it may be desired in some cases to distinguish between two sequences which can hybridise to each other but contain some mismatches—an "inexact match", "imperfect match", or "inexact complementarity"—and two sequences which can hybridise to each other with no mismatches—an "exact match", "perfect match", or "exact complementarity". Further, possible degrees of mismatch are considered.

As used herein, the term 'organ protection sequence' ('OPS') refers to a sequence comprised of a plurality of microRNA (miRNA) target sequences of natural or synthetic origin and, optionally, one or more auxiliary sequences. Where an OPS confers protection to multiple organs it may be referred to as a multi-organ protection (MOP) sequence. The term 'target sequence' refers to a sequence comprised within a mRNA sequence, such as within an untranslated region (UTR), that is targeted for binding by a specified miRNA. Binding occurs by way of nucleic acid hybridisation between complementary base pairs comprised within the miRNA and the corresponding target sequence. The binding interaction may be optimised such that no mismatches between the specified miRNA and the target sequence occur, or mismatches are limited to no more than a single base pair mismatch across the length of the target sequence. In an embodiment of the invention a single base mismatch is limited to the 5' or 3' end of the target sequence. Optimised sequences can also be described as being perfectly matched to the target miRNA and may differ from the wild type binding sequence by two or more base pairs. Wild type sequences that comprise more than two naturally occurring mismatches are deemed to be un-perfectly or imperfectly matched to the corresponding miRNA sequence.

The term 'operatively linked', when applied to nucleic acid sequences, for example in an expression construct, indicates that the sequences are arranged so that they function cooperatively in order to achieve their intended purposes. By way of example, in a DNA vector a promoter sequence allows for initiation of transcription that proceeds through a linked coding sequence as far as a termination sequence. In the case of RNA sequences, one or more untranslated regions (UTRs) may be arranged in relation to a linked polypeptide coding sequence referred to as an open reading frame (ORF). A given mRNA as disclosed herein may comprise more than one ORFs, a so-called polycistronic RNA. A UTR may be located 5' or 3' in relation to an operatively linked coding sequence ORF. UTRs may comprise sequences typically found in mRNA sequences found in nature, such as any one or more of: Kozak consensus sequences, initiation codons, cis-acting regulatory elements, poly-A tails, internal ribosome entry sites (IRES), structures regulating mRNA longevity, sequences directing the localisation of the mRNA, and so on. An mRNA may comprise multiple UTRs that are the same or different. The one or more UTRs may comprise or be located proximate or adjacent to an OPS.

The term 'expressing a polypeptide' in the context of the present invention refers to production of a polypeptide for which the polynucleotide sequences described herein code. Typically, this involves translation of the supplied mRNA sequence—i.e., the ORF—by the ribosomal machinery of the cell to which the sequence is delivered.

The term 'diseased' as used herein, as in 'diseased cells' and/or 'diseased tissue' indicates tissues and organs (or parts thereof) and cells which exhibit an aberrant, non-healthy or disease pathology. For instance, diseased cells may be infected with a virus, bacterium, prion or eukaryotic parasite; may comprise deleterious mutations; and/or may be cancerous, precancerous, tumoral or neoplastic. Diseased cells may comprise an altered intra-cellular miRNA environment when compared to otherwise normal or so-called healthy cells. In certain instances, disease cells may be pathologically normal but comprise an altered intra-cellular miRNA environment that represents a precursor state to disease. Diseased tissues may comprise healthy tissues that have been infiltrated by diseased cells from another organ or organ system. By way of example, many inflammatory diseases comprise pathologies where otherwise healthy organs are subjected to infiltration with immune cells such as T cells and neutrophils. By way of a further example, organs and tissues subjected to stenotic or cirrhotic lesions may comprise both healthy and diseased cells in close proximity.

The term 'cancer' as used herein refers to neoplasms in tissue, including malignant tumors, which may be primary cancer starting in a particular tissue, or secondary cancer having spread by metastasis from elsewhere. The terms cancer, neoplasm and malignant tumors are used interchangeably herein. Cancer may denote a tissue or a cell located within a neoplasm or with properties associated with a neoplasm. Neoplasms typically possess characteristics that differentiate them from normal tissue and normal cells. Among such characteristics are included, but not limited to: a degree of anaplasia, changes in morphology, irregularity of shape, reduced cell adhesiveness, the ability to metastasize, and increased cell proliferation. Terms pertaining to and often synonymous with 'cancer' include sarcoma, carcinoma, malignant tumor, epithelioma, leukaemia, lymphoma, transformation, neoplasm and the like. As used herein, the term 'cancer' includes premalignant, and/or precancerous tumors, as well as malignant cancers.

The term 'healthy' as used herein, as in 'healthy cells' and/or 'healthy tissue' indicates tissues and organs (or parts thereof) and cells which are not themselves diseased and/or approximate to a typically normal functioning phenotype. It can be appreciated that in the context of the invention the term 'healthy' is relative, as, for example, non-neoplastic cells in a tissue affected by tumors may well not be entirely healthy in an absolute sense. Therefore, 'non-healthy cells' means cells which are not themselves neoplastic, cancerous or pre-cancerous, but which may be cirrhotic, inflamed, or infected, or otherwise diseased, for example. Similarly, 'healthy or non-healthy tissue' means tissue, or parts thereof, without tumors, neoplastic, cancerous or pre-cancerous cells; or other diseases as mentioned above; regardless of overall health. For instance, in the context of an organ comprising cancerous and fibrotic tissue, cells comprised within the fibrotic tissue may be thought of as relatively 'healthy' compared to the cancerous tissue. Models used for approximation of normal functioning phenotypes for 'healthy' cells may include immortalised cell lines that are otherwise close to the originator cells in terms of cellular function and gene expression.

In an alternative embodiment, the health status of a cell, cell type, tissue and/or organ is determined by the quantification of miRNA expression. In certain disease types, such as cancer, the expression of particular miRNA species is affected, and can be up- or down-regulated compared to unaffected cells. This difference in the miRNA transcriptome can be used to identify relative states of health, and/or to track the progression of healthy cells, cell types, tissues and/or organs towards a disease state. The disease state may include the various stages of transformation into a neoplastic cell. In embodiments of the present invention the differential variations in the miRNA transcriptome of cell types comprised within a given organ or organ system is leveraged in order to control protein expression in the different cell types.

As used herein, the term 'organ' is synonymous with an 'organ system' and refers to a combination of tissues and/or cell types that may be compartmentalised within the body of a subject to provide a biological function, such as a physiological, anatomical, homeostatic or endocrine function. Suitably, organs or organ systems may mean a vascularized internal organ, such as a liver or pancreas. Typically, organs comprise at least two tissue types, and/or a plurality of cell types that exhibit a phenotype characteristic of the organ. Tissues or tissue systems may cooperate but not formally be considered as an organ. For example, blood is generally considered a tissue, or even a liquid tissue, but depending upon the definition used may not be regarded as an organ in the strict sense. Nevertheless, the compositions and methods of the invention in certain embodiments may serve to exhibit a protective effect in respect of organs, tissues and tissue systems including the blood, haematopoietic and lymphoid tissue.

The term 'therapeutic virus' as used herein refers to a virus which is capable of infecting and killing cancer cells, sometimes by direct viral lysis (oncolysis), and/or including indirect killing by the stimulation of host anti-tumoral responses. Oncolytic viruses are frequently characterised by having increased activity in diseased cells, including cancer cells, compared with healthy cells. Therapeutic viruses may also include attenuated or modified viruses that are useful in vaccine formulation.

TABLE 1

Examples of Therapeutic Viruses and Subtypes Thereof

| Therapeutic Virus | Type |
|---|---|
| Rhabdoviridae family (e.g., Maraba virus, Vesicular Somatitis virus) | Enveloped RNA |
| Poxviridae family (e.g., Vaccinia virus) | Enveloped DNA |
| Reoviridae family (e.g., Reovirus) | Non enveloped RNA |
| Paramyxoviridae family (e.g., Measles virus, Newcastle Disease virus) | Enveloped RNA |
| Picornaviridae family (e.g., Poliovirus, Coxsackie A virus, Seneca Valley virus) | Non enveloped RNA |
| Togaviridae family (e.g., Semliki Forest Virus, Sindbis Virus) | Enveloped RNA virus |
| Parvoviridae family (e.g., Protoparvovirus) | Non enveloped DNA |
| Herpesviridae family (e.g., Herpes Simplex Virus Type 1) | Enveloped DNA |
| Adenoviridae family (e.g., Adenovirus) | Non enveloped DNA |

In embodiments of the invention viruses may be selected from any one of the Groups I-VII of the Baltimore classification of viruses (Baltimore D (1971). "Expression of animal virus genomes". Bacteriol Rev. 35 (3): 235-41). In specific embodiments of the invention suitable viruses may be selected from Baltimore Group I, which are characterised as having double stranded DNA viral genomes; Group II, which are characterized as having positive single stranded DNA genomes, Group III, which are characterized as having double stranded RNA viral genomes, Group IV, which have single stranded positive RNA genomes; and Group V, which have single stranded negative RNA genomes.

The term 'virulence gene' or 'virulence factor' as used herein refers to a gene or gene product which aids in the replication of a therapeutic virus such as an oncolytic virus within or lysis of the cells which it infects. The term 'replication factor' is used as a synonymous term herein. Virulence factors may typically be viral genes encoded by the viral genome. Virulence factors may be involved in functions such as intracellular immune system suppression and evasion, viral genome replication, the spread or transmission of virions, the production or assembly of structural coat proteins, the activation of viruses in a latent state, the prevention of viral latency, and the takeover of host cell processes. Several virulence factors have cellular or other equivalents which can compensate for the function of these genes if lacking in the virus genome. Some viruses can be modified with exogenous virulence genes, which increase their ability to replicate, lyse cells, and spread.

The term "viral entry receptor" or "viral fusion receptor" refers to a cell surface protein or other marker, or antigen, present on the surface of a target cell, to which a virus may bind before entry into that cell, as part of the 'entry' phase of the viral life cycle. As is well appreciated, the viral genome must enter into the target cell for infection and replication to take place. Binding between the virus and the target cell are thought to be due to interactions between the viral entry receptor and viral proteins present on the viral capsid or the viral envelope (depending on virus type). Subsequent entry may be mediated by membrane fusion (in viruses with a viral envelope), by endocytosis, and/or by injection of the viral genome only. Viral entry receptors may be natural (found in existing organisms), or may be modified, synthesised, and/or engineered to act as a binding target for viral proteins. The viral proteins, which bind to the viral entry receptors, may also be natural (found in existing viruses) or may be modified, synthesised, and/or engineered to bind to a natural or modified/synthesised or engineered viral entry receptor.

In specific embodiments of the present invention, the mRNA sequences enhance or sustain the oncolytic potency of a co-administered virus in a tumor located within an organ through differential expression of one or more proteins or polypeptides that enhance viral virulence preferentially in the tumor. In this way, the mRNA may code for one or more factors that enhance the biological potency of the oncolytic virus by: increased replication and/or increased viral oncolytic activity and/or increased viral progeny and/or increased an adaptive antitumor immune response. In further embodiments of the invention, the compositions may encode a protein or polypeptide that controls the interaction between host immune cells and oncolytic virus within a tumor. In yet a further embodiment, the compositions of the invention can be used to produce proteins or polypeptides that modulate differential patterns of oncolytic or other therapeutic virus activity as well as expression of immune co-stimulatory molecules that are administered via the virion, exogenously or via a delivery particle of the invention.

The term 'polypeptide' as used herein is a polymer of amino acid residues joined by peptide bonds, whether produced naturally or in vitro by synthetic means. Polypeptides of less than around 12 amino acid residues in length are typically referred to as "peptides" and those between about 12 and about 30 amino acid residues in length may be referred to as "oligopeptides". The term "polypeptide" as used herein denotes the product of a naturally occurring polypeptide, precursor form or proprotein. Polypeptides can also undergo maturation or post-translational modification processes that may include, but are not limited to: glycosylation, proteolytic cleavage, lipidization, signal peptide cleavage, propeptide cleavage, phosphorylation, and such like. The term "protein" is used herein to refer to a macromolecule comprising one or more polypeptide chains.

The term 'gene product' as used herein refers to the peptide or polypeptide encoded by at least one coding sequence or Open Reading Frame (ORF) comprised within an mRNA construct of the invention as described herein. A polycistronic mRNA construct may be used, which results in the production of multiple gene products encoded by multiple ORFs located on the same polynucleic strand. It will be appreciated that multiple ORFs may lead to the production in situ of a variety of products—e.g., proteins, peptides or polypeptides—that may cooperate functionally, or may form complexes and/or multimeric proteins with diverse biological and potentially therapeutic effects.

The gene product encoded by the mRNA is typically a peptide, polypeptide or protein. Where a particular protein consists of more than one subunit, the mRNA may code for one or more than one subunit within one or more ORFs. In alternative embodiments, a first mRNA may code for a first subunit, whilst a second co-administered mRNA may code for a second subunit that, when translated in situ, leads to assembly of a multi-subunit protein gene product.

Delivery of mRNA directly to cells allows direct and controllable translation of the desired gene products such as polypeptides and/or proteins in the cells. Provision of mRNA specifically allows not only for the use of cell expression modulation mechanisms, such as miRNA mediated control (as detailed in specific embodiments below), but also represents a finite and exhaustible supply of the product, rather than the potentially permanent change to the transcriptome of a target cell, which an episomal or genomically inserted DNA vector might provide.

In embodiments of the present invention, an mRNA sequence is provided that comprises a sequence that codes for at least one polypeptide in operative combination with one or more untranslated regions (UTRs) that may confer tissue specificity, and stability to the nucleic acid sequence as a whole. By 'tissue specificity', it is meant that translation of the protein product encoded by the mRNA is modulated according to the presence of the UTRs. Modulation may include permitting, reducing or even blocking detectable translation of the mRNA into a protein. The UTRs may be linked directly to the mRNA in cis—i.e., on the same polynucleotide strand. In an alternative embodiment, a first sequence that codes for a gene product is provided and a further second sequence, that hybridises to a portion of the first sequence, is provided that comprises one or more UTRs that confer tissue specificity to the nucleic acid sequence as a whole. In this latter embodiment, the UTR is operatively linked to the sequence that encodes the gene product in trans.

According to specific embodiments of the invention, an mRNA is provided that comprises such associated nucleic acid sequences operatively linked thereto as are necessary to prevent or reduce expression of a gene product in non-diseased liver tissue, e.g., in healthy hepatocytes. The mRNA is hereafter referred to as a 'coding mRNA'. As such, this coding mRNA construct, or transcript, is provided that comprises a 5' cap and UTRs necessary for ribosomal recruitment and tissue and/or organ specific expression (typically, but not exclusively positioned 3' to the ORF), as well as start and stop codons that respectively define one or more ORFs. When the construct is introduced into non-diseased liver, lung, pancreas, breast, brain/CNS, kidney, spleen, muscle, skin and/or colon-GI tract, expression of the gene product is prevented or reduced. In contrast, neoplastic or otherwise diseased cells comprised within the aforementioned organs typically do not conform to normal non-diseased cell expression patterns, possessing a quite different miRNA transcriptome. The polypeptide(s) encoded by the mRNA is translated specifically in these aberrant cells but not—or to a lesser extent—in neighbouring healthy or non-diseased cells. Delivery of the mRNA construct to the organs mentioned above may be achieved via a particulate delivery platform as described herein, or in any suitable way known in the art. Cell type specific expression can be mediated via microRNA modulation mechanisms such as those described in more detail below.

A 'therapeutic component' or 'therapeutic agent' as defined herein refers to a molecule, substance, cell or organism that when administered to an individual human or other animal as part of a therapeutic intervention, contributes towards a therapeutic effect upon that individual human or other animal. The therapeutic effect may be caused by the therapeutic component itself, or by another component of the therapeutic intervention. The therapeutic component may be a coding nucleic acid component, in particular an mRNA. The coding nucleic acid component(s) may code for therapeutic enhancement factors, as defined below. A therapeutic component may also comprise a drug, optionally a chemotherapeutic drug such as a small molecule or monoclonal antibody (or fragment thereof). In some embodiments, a therapeutic component may comprise a cell, such as a recombinantly modified immune effector cell—e.g., a CAR-T cell. In other embodiments of the invention, the therapeutic agent comprises a therapeutic virus, such as an oncolytic virus or a viral vector.

The term 'therapeutic effect' refers to a local or systemic effect in an animal subject, typically a human, caused by a pharmacologically or therapeutically active agent that comprises a substance, molecule, composition, cell or organism that has been administered to the subject, and the term 'therapeutic intervention' refers to the administration of such a substance, molecule, composition, cell or organism. The term thus means any agent intended for use in the diagnosis, cure, mitigation, treatment or prevention of disease or in the enhancement of desirable physical or mental development and conditions in an animal or human subject. The phrase 'therapeutically-effective amount' means that amount of such an agent that produces a desired local or systemic effect at a reasonable benefit/risk ratio applicable to any treatment. In certain embodiments, a therapeutically effective amount of an agent will depend on its therapeutic index, solubility, and the like. For example, certain therapeutic agents of the present invention may be administered in a sufficient amount to produce a reasonable benefit/risk ratio applicable to such treatment. In the specific context of treatment of cancer, a 'therapeutic effect' can be manifested by various means, including but not limited to, a decrease in solid tumor volume, a decrease in the number of cancer cells, a decrease in the number of metastases observed, an increase in life expectancy, decrease in cancer cell proliferation, decrease in cancer cell survival, a decrease in the expression of tumor cell markers, and/or amelioration of various physiological symptoms associated with the cancerous condition. In the specific context of the treatment of a viral, bacterial or parasitic infection, such as by prophylaxis through vaccination, a 'therapeutic effect' may be shown by full or partial resistance to pathogen challenge, presence of circulating antibodies to the pathogen in the human or animal subject, or other known measures of vaccine efficacy.

In one embodiment, the subject to whom therapy is administered is a mammal (e.g., mouse, rat, primate, non-human mammal, domestic animal or livestock, such as a dog, cat, rabbit, cow, horse, sheep, goat and the like), and is suitably a human. In a further embodiment, the subject is an animal model of cancer. For example, the animal model can be an orthotopic xenograft animal model of a human-derived cancer, suitably liver, lung, pancreas, breast, brain, kidney, muscle, skin and/or colon-GI tract cancer.

In a specific embodiment of the methods of the present invention, the subject has not yet undergone a therapeutic treatment, such as therapeutic viral therapy, chemotherapy, radiation therapy, targeted therapy, vaccination, and/or anti-immune checkpoint therapy. In still another embodiment, the subject has undergone a therapeutic treatment, such as the aforementioned therapies.

In further embodiments, the subject has had surgery to remove cancerous or precancerous tissue. In other embodiments, the cancerous tissue has not been removed, for example, the cancerous tissue may be located in an inoperable region of the body, such as in a tissue or organ that if subjected to surgical intervention may compromise the life of the subject, or in a region where a surgical procedure would cause considerable risk of permanent harm or even lethality.

In some embodiments, the provided coding mRNA construct may code for a 'therapeutic enhancement factor'. According to the present invention therapeutic enhancement factors are gene products or polypeptides that may enhance or facilitate the ability of another, co-administered therapeutic agent, to exert a therapeutic effect upon a given cell, suitably the target cell. When introduced into or in the vicinity of the target cell, expression of the therapeutic enhancement factor may cooperate with a co-administered therapeutic agent thereby enabling or enhancing the therapeutic activity of the agent. In some embodiments, the therapeutic enhancement factor may enhance the ability of a co-administered oncolytic virus to lyse cancer cells. In other embodiments of the invention, the therapeutic enhancement factor may effect an alteration of a tumor microenvironment so as to assist or recruit the subject's own immune response. In this latter embodiment, the alteration of the tumor microenvironment may assist co-administration of an oncolytic virus, or a CAR-T or other adoptive cell based therapy, or an immune checkpoint inhibitor such as a monoclonal antibody or equivalent to PD-1/PD-L1. In some embodiments, the therapeutic enhancement factor may enable the conversion of a prodrug into an active form. In other embodiments the therapeutic enhancement factor may act as an adjuvant for a co- or sequentially administered vaccine. Alternatively the therapeutic enhancement factor may act as an adjuvant for a co- or sequentially administered attenuated or modified virus, such as a modified adenovirus utilised in a vaccine formulation.

Multiple therapeutic enhancement factors may be combined in compositions according to specific embodiments of the present invention. In such embodiments, the coding sequences for each therapeutic enhancement factor may be present in separate mRNA molecules. In some embodiments, sequences for more than one therapeutic enhancement factor may be present on the same mRNA molecule. In such cases the polycistronic mRNA molecule further comprises sequences as necessary for the expression of all coded sequences, such as internal ribosome entry sites (IRES).

In embodiments where multiple different mRNA molecules are comprised in one or more delivery system, it is contemplated that each delivery system—e.g., particle, liposome, viral vector system—may comprise one or more than one type of mRNA molecule as the 'payload', that is, not every delivery payload in a particular embodiment will necessarily comprise all of the mRNA molecules provided in said embodiment. In this way, it is also considered possible to direct different delivery systems and their associated sequences to different target cells, with the targeting agents described herein.

The mRNA constructs of certain embodiments of the invention may be synthesised from a polynucleotide expression construct, which may be for example a DNA plasmid. This expression construct may comprise any promoter sequence necessary for the initiation of transcription and a corresponding termination sequence, such that transcription of the mRNA construct can occur. Such polynucleotide expression constructs are contemplated to comprise embodiments of the invention in their own right.

The gene product encoded by the mRNA may be of any type suitable for producing a therapeutic effect. In the context of treating cancer, the gene product encoded by the mRNA may suitably include genes which when expressed by a cancer cell cause or aid in the destruction of the cancer cell.

Tumor suppressor genes such as p53 may be provided by the constructs of the invention. p53 plays a role in cell processes including apoptosis and genomic stability. It is involved in the activation of the DNA repair process in response to genomic damage, and can arrest cell growth and reproduction.

Cell death can occur through a number of mechanisms, and includes programmed cell death or apoptosis, which describes processes for controlled cell death mediated by intrinsic factors which are detected as indicating cell stress. Also encompassed by these terms is cell death mediated by extrinsic signals such as those received by the cells of the immune system, for example cytotoxic T-cells or natural killer cells. Since pathways leading to apoptosis are often inhibited by cancer cells in order to escape cell death, such pathways are a promising target for cancer treatment.

Genes which promote cell death, for instance by apoptosis—so-called suicide genes—which when expressed cause the cell to activate the process of apoptosis, may also be provided by the compositions and constructs of the invention. Cancer cells often possess mutated and/or functionless versions of these apoptosis-related genes, and so cannot undergo apoptosis in response to external signals. Suicide gene therapy may also refer to the introduction of genes which allow the conversion of a non-toxic compound or prodrug into a lethal drug (Duarte et al. Cancer Letters, 2012; 324(2): 160-170). According to embodiments of the invention, such gene products can be introduced selectively into diseased cells, such as neoplastic cells, marking them for destruction by induced apoptosis or delivery of an otherwise non-toxic compound or prodrug.

In specific embodiments of the invention, the mRNA may encode checkpoint inhibitors, such as inhibitors of PD-1 receptor (CD279) or its ligands PD-L1 (B7-H1; CD274) and PD-L2 (B7-DC; CD273). Some cancer cells have a large amount of PD-L1, which helps them evade T-cell mediated immune attack. Hence, the mRNA may encode a protein or polypeptide that binds to or otherwise interferes with the function of the PD-1/PD-L1 or PD-1/PD-L2 axis within diseased or neoplastic cells within a target organ. Suitable proteins or polypeptides may include antibodies, which may be monoclonal or polyclonal, or antigen binding fragments thereof, or other antigen binding microproteins, that bind to PD-1 receptor, PD-L1, PD-L2, or complexes of ligand and receptor. This effect may also be observed by use of protein or polypeptide inhibitors of the cytotoxic T lymphocyte antigen 4 (CTLA4) pathway, another so-called immune checkpoint. Inhibition of either or both pathways is known to result in a change in the immune response within the tumor microenvironment that may positively benefit the health of the patient. In addition, by modulating the immune response in a subject, the compositions of the present invention may show particular utility in combinatorial therapies with other anti-cancer therapeutic approaches, such as radiotherapy or chemotherapy. FDA approved anti-PD-1 pathway inhibitors include pembrolizumab and nivolumab. Known anti-PD-L1 inhibitors include MPDL-3280A, BMS-936559 and atezolizumab. Anti-CTLA-4 therapeutic inhibitors include ipilimumab and tremelimumab. The compositions of the invention may be used to deliver such inhibitors of the programmed cell death pathway- or functional mimetics thereof—selectively to diseased cells within a target organ in a subject by leveraging the differential miRNA environment in those cells. Alternatively, the compositions of the invention may be used in combination with checkpoint inhibitors or other related anti-cancer therapies to deliver a protein that activates immune cells such as IL-12.

Interleukin 12 (IL-12) is an immune-stimulatory cytokine for immune cells including T cells and NK cells. IL-12 is a heterodimeric cytokine that is produced specifically by phagocytic cells as well as antigen-presenting cells and enhances anti-tumor immune responses. A consequence of the potent immune stimulatory properties of IL12 is that systemic administration leads to serious side effects that limit its clinical application in patients. Expression of IL-12 by engineered NK92 at tumor sites has been shown to increase the antitumor activities of chimeric antigen receptor (CAR)-modified T cells (Luo et al. Front Oncol. (2019) Dec. 19; 9:1448). It is believed that IL-12 induced IFNγ accumulation in tumors also promotes the penetration of CAR-T or other host immune cells (e.g., NK cells) into the tumors, thereby enhancing the therapeutic effects (Chinnasamy D. et al. Clin Cancer Res 2012:18/Chmielewski M. et al. Cancer Res 2011; 71/Kerkar S P. Et al. J Clin Invest 2011; 121/Jackson H J. Et al. Nat Rev Clin Oncol 2016; 13). In embodiments of the present invention the compositions of the invention comprise an mRNA that include at least one ORF that encodes functional IL-12 or an analogue or derivative thereof. Since, wild type IL-12 is comprised of a heterodimer of 35 kDa IL-12A and 40 kDa IL-12B subunits, the ORF may comprise one of these subunits and be administered in combination with another mRNA encoding the other subunit thereby allowing the assembly of functional IL-12 in the cell. Alternatively, functional IL-12 may be in the form of a modified single chain version of IL-12 that comprises both subunits within a single ORF (for example, see SEQ ID NO: 63]).

In some embodiments of the invention, the coding mRNA is delivered in conjunction with CAR-T or other adoptive cell therapy to provide transient expression of the coding mRNA.

Chimeric antigen receptor T-cells (CAR-T cells) are immune cells, typically T-lymphocytes, which have been modified to express receptors which target specific cell types, including cancer cells. This adoptive immunotherapy involves the transfer of autologous antigen-specific T cells generated ex vivo to the patient. 'Autologous' means that the T-cells are the patient's T-cells. The T cells used for adoptive immunotherapy can be generated either by expansion of antigen-specific T cells or redirection of T cells through genetic engineering (Park et al. Trends Biotechnol. 2011; 29(11): 550-7). Modified T cells with new or improved specificities have been successfully generated through the insertion of engineered chimeric antigen receptors (CARs).

An example of FDA approved CAR-T cell therapy is tisagenlecleucel (brand name Kymriah), which is an autologous immunocellular therapy involving the use of the patient's T-cells that are genetically engineered to express a high level of a chimeric receptor for CD19 glycoprotein. CD19 is specifically and consistently expressed on the surface of B-cells, including most lymphomas, leukemia, as well as healthy B-cells (Vairy et al. Drug Des Devel Ther. 2018; 12:3885-98).

In some embodiments, the engineered T cells comprise a specific class of T cells, such as, for example, gamma delta T cells, a subtype of T cells that selectively target tumoral cells without affecting healthy ones. CARs have successfully allowed T cells to be redirected against antigens expressed at the surface of tumor cells from various malignancies including lymphomas and solid tumors (Jena, Dotti et al. supra). In some embodiments, the engineered T cells comprise at least a population of autologous T cells in which the CAR-T cells are engineered to eliminate expression of the endogenous αβ T-cell receptor (TCR) to prevent a graft-versus-host response without compromising CAR-dependent effector functions. In some embodiments, the engineered T cells comprise at least a population of allogeneic T cells. In some embodiments, the engineered T cells comprise at least a population of autologous T cells and a population of allogeneic T cells.

In some embodiments, T cell activation results in immune cell activation in which inflammatory cytokines are released by the T cells to promote an inflammation and/or immune response. In some embodiments, T cell activation results in cytotoxic activity in which cytotoxins are released by the T cells to promote cancer cell death. In some embodiments, T cell activation results in proliferation in which interleukins are released by the T cells to promote cell development and division. In some embodiments, T cell activation results in a combination of at least two of immune cell activation, cytotoxic activity, and/or proliferation.

The mRNA compositions provided in embodiments herein are useful to improve the safety and efficacy of CAR-T-cells. For example, the polypeptide encoded by the mRNA described herein may be used to recruit specific immune cells or modified subsets of immune cells such as CAR-T cells to the tumor microenvironment.

In some embodiments, the coding mRNA is used to provide a 'CAR-T target', being a target for the receptors expressed by CAR-T cells to bind to. As the CAR-T cells can be engineered to express particular receptors towards particular targets, so too can compositions according to the invention be used to induce the expression of those targets in a target cell type. Due to the differential expression enabled by embodiments of the present invention, this approach can allow CAR-T cells to selectively target only those cells in which the expression of the provided mRNA occurs and so reduce off-target effects.

By this method, it is possible to induce expression in target cells of CAR-T receptor targets which are not usually expressed by that cell type, in order to allow the CAR-T cells to target only those cells which successfully express the polypeptide encoded by the mRNA of the invention. CAR-T targets can be selected which are rare or absent in cells naturally present within the subject. For instance, when a human subject is to be treated, a CAR-T target which is never naturally found on a human cell, to entirely prevent the CAR-T cells targeting those subject cells which do not express the supplied mRNA.

In some such embodiments, the CAR-T target can be modified, synthesised and/or engineered so that it is effectively targeted by the CAR-T provided. Similarly, the CAR-T cell itself can also or alternatively be designed so that the receptor it is engineered to express is modified, synthesised and/or engineered, to prevent it from binding to cell targets other than those encoded by the mRNA of an embodiment of the invention. In this way, it is also possible to design, modify or synthesise a unique pairing of CAR-T receptors and CAR-T targets which is not present in nature, in order to prevent the CAR-T cells from affecting any cells other than those which express the aforementioned mRNA of the invention.

In some embodiments, the coding mRNA is used to attract CAR-T cells to a particular site in a subject. In some embodiments, the coding mRNA is used to overcome insufficient migration of an immune cell to the tumor microenvironment. In response to specific chemokines, different immune cell subsets migrate into the tumor microenvironment and regulate tumor immune responses in a spatiotemporal manner. In some embodiments, the coding mRNA is used to enhance CAR-T cell activation. In addition, chemokines can directly target non-immune cells, including tumor cells and vascular endothelial cells, in the tumor microenvironment, and they have been shown to regulate tumor cell proliferation, cancer stem-like cell properties, cancer invasiveness and metastasis. In some embodiments, the immune cell is a T cell, a natural killer (NK) cell, a B cell, an antigen-presenting cell (APC) such as a macrophage or dendritic cell, or any combination thereof.

In some embodiments, the coding mRNA can be used to overcome insufficient migration of CAR-T cells to the tumor microenvironment, and prevent off-target CAR-T activity. In some embodiments, the mRNA is delivered to the tumor microenvironment, and the coding mRNA encodes a gene product that attracts or otherwise recruits CAR-T cells to the tumor microenvironment. In some embodiments, the coding mRNA expresses a chemokine. By way of non-limiting example, one or more coding mRNAs can encode one or more chemokines that attract T-cells such as CCL2, CCL3, CCL4, CCL5, CCL20, CCL22, CCL28, CXCL8, CXCL9, CXCL10, CXCL11, CXCL12, XCL1, and any combination thereof. In situations where the reverse effect is desired, such as in autoimmune disease, the coding mRNA can express blockers, antagonists and/or inhibitors of the above-mentioned factors.

In some embodiments, the coding mRNA is transiently expressed in the tumor microenvironment. In some embodiments, the coding mRNA encodes a cytokine or other gene product involved in regulating the survival, proliferation, and/or differentiation of immune cells in the tumor response, such as, for example, activated T cells and NK cells. By way of non-limiting example, the coding mRNA can encode for a cytokine such as IL-1, IL-2, IL-4, IL-6, IL-8, IL-10, IL-12, IL-17, IL-33, IL-35, TGF-beta, TNF α, TNFβ, IFNα, IFMβ, IFNgamma, and any combination thereof. Again, in situations where the reverse effect is desired, such as in autoimmune disease, the coding mRNA can express blockers, antagonists and/or inhibitors of the above-mentioned factors.

In some embodiments, an mRNA delivery system as described herein delivers an mRNA that codes for a gene-editing agent to a target cell population. In some embodiments, the mRNA codes for a sequence-specific nuclease that targets a gene locus and disrupts expression of one or more endogenous gene produces in the target cell population. In some embodiments, the mRNA codes for a sequence-specific nuclease that targets a T cell receptor (TCR)-related gene locus, thereby disrupting expression of one or more domains in the TCR.

In some embodiments, the described mRNA delivery systems may be used to deliver an mRNA that codes for one or more agents that program engineered T cells toward a desired phenotype. In some embodiments, the mRNA may be used to induce markers and transcriptional patterns that are characteristic of a desired T cell phenotype. In some embodiments, the mRNA may be used to promote development of CD26L+ central memory T cells (Tcm), which have been shown to improve CAR-T treatment. (Moffett et al. Nature Commun. 2017; 8(1): 389).

In some embodiments, the described mRNA delivery systems may be used to deliver an mRNA that codes for a member of the Vascular endothelial growth factor (VEGF). This family of signal proteins is an angiogenic factor which stimulates the formation of blood vessels and has been used to repair damaged cardiomyocytes after infarction.

MicroRNAs (miRNAs) are a class of noncoding RNAs each containing around 20 to 25 nucleotides, some of which are believed to be involved in post-transcriptional regulation of gene expression by binding to complementary target sequences in the 3' untranslated regions (3' UTR) of target mRNAs, leading to their silencing. These miRNA complementary target sequences are also referred to herein as miRNA binding sites, or miRNA binding site sequences. Certain miRNAs are highly tissue-specific in their expression; for example, miR-122 and its variants are abundant in the liver and infrequently expressed in other tissues (Lagos-Quintana et al. Current Biology. 2002; 12: 735-739).

The miRNA system therefore provides a robust platform by which nucleic acids introduced into cells can be silenced in selected cell types in a target tissue, and expressed in others. By including a target sequence for a particular given miRNA into an mRNA construct to be introduced into target cells, particularly within a UTR, expression of certain introduced genes can be reduced or substantially eliminated in some cell types, while remaining in others (Brown and Naldini, Nat Rev Genet. 2009; 10(8): 578-585).

In accordance with specific embodiments of the present invention it is contemplated that a plurality of such miRNA target sequences can be comprised within an organ protection sequence, which is then included in the mRNA construct. Where a plurality of miRNA target sequences are present, this plurality may include for example greater than two, greater than three, typically greater than four miRNA target sequences. These miRNA target sequences may be arranged sequentially, in tandem or at predetermined locations within, a specified UTR within the mRNA constructs. Multiple miRNA target sequences may be separated with auxiliary sequences that serve to support or facilitate the functioning of the organ protection sequence as a whole. By way of example, suitable auxiliary sequences may consist of a linker or spacer sequence, which may be randomized, or may comprise a particular sequence, for example, "uuuaaa", although other spacer sequences can also be used. The length of the spacer can vary, and can comprise repetitions of a spacer sequence, for example the spacer "uuuaaa" can be included once (i.e., "uuuaaa"), twice (i.e., "uuuaaauuuaaa"—SEQ ID NO: 1), three times, four times, five times, or six times between each and any target sequence to be linked. In some embodiments, no spacer sequence may be present between binding site sequences.

miRNA-122, despite its abundance in healthy non-diseased liver tissue, is reduced in the majority of liver cancers as well as in diseased cells (Braconi et al. Semin Oncol. 2011; 38(6): 752-763, Brown and Naldini, Nat Rev Genet. 2009; 10(8): 578-585). By the above-mentioned method, it has been found that when the target tissue is the liver, translation of the introduced mRNA sequences can be facilitated in cancerous liver cells and reduced or substantially eliminated in transfected healthy cells, by including miRNA-122 target sequence (for example, SEQ ID NO: 1) in their 3' UTRs.

In a similar way, differential translation of such mRNA is also possible between cancer cells and healthy cells in other organs, by using other miRNA target sequences. Suitable candidates include (but are not limited to) target sites for: miRNA-1, miRNA-125, miRNA-199, miRNA-124a, miRNA-126, miRNA-Let7, miRNA-375, miRNA-141, miRNA-142, miRNA-143, miRNA-145, miRNA-148, miRNA-194, miRNA-200c, miRNA-34a, miRNA-192, miRNA-194, miRNA-204, miRNA-215 and miRNA-30 a,b, c. Table 2 demonstrates further (non-limiting) examples of miRNA sequences where differential expression has been demonstrated.

miRNA-1, miR-133a and miR-206 have been described as examples of muscle and/or myocardium-specific miRNAs (Sempere et al. Genome Biology. 2004; 5:R13; Ludwig et al. Nucleic Acids Research. 2016; 44(8): 3865-3877). miRNA-1 has also been demonstrated to be dysregulated in disease, for example downregulation of miRNA-1 has been detected in infarcted heart tissue (Bostjancic E, et al. Cardiology. 2010; 115(3):163-169), while a drastic reduction of miRNA-1 has also been detected in rhabdomyosarcoma cell lines (Rao, Prakash K et al. FASEB J. 2010; 24(9):3427-3437). Use of miRNA-1, miR-133a and miR-206 may be particularly considered where compositions according to the invention are to be administered intramuscularly, so to reduce expression in local normal myocytes, if desired.

miRNA-125 is downregulated in several solid tumors, such as hepatocellular carcinoma (Coppola et al. Oncotarget 2017; 8); breast (Mattie et al. Mol Cancer 2006; 5), lung (Wang et al. FEBS J 2009), ovarian (Lee et al. Oncotarget 2016; 7), gastric (Xu et al. Mol Med Rep 2014; 10), colon (Tong et al. Biomed Pharmacother 2015; 75), and cervical cancers (Fan et al Oncotarget 2015; 6); neuroblastoma, medulloblastoma (Ferretti et al. Int J Cancer 2009; 124), glioblastoma (Cortez et al. Genes Chromosomes Cancer 2010; 49), and retinoblastoma (Zhang et al; Cell signal 2016; 28).

Several miRNA species are also differentially expressed in glioblastoma multiforme cells (Zhangh et al. J Miol Med 2009; 87/Shi et al. Brain Res 2008; 1236) compared to non-diseased brain cells (e.g., neurons), with miRNA-124a one of the most dysregulated (Karsy et al. Gene Cancer 2012; 3; Riddick et al. Nat Rev Neurol 2011; 7; Gaur et al. Cancer Res 2007; 67/Silber et al. BMC Med 2008; 6).

In lung cancer, a recent meta-analysis confirmed the downregulation of Let-7 (as well as miRNA-148a and miRNA-148b) in non-small-cell lung cancer (Lamichhane et al. Disease Markers 2018).

Similarly, miRNA-375 expression has been found to be downregulated in pancreatic cancer cells, compared to healthy pancreatic cells (Shiduo et al. Biomedical Reports 2013; 1). In the pancreas, miRNA-375 expression has been indicated to be high in normal pancreas cells but significantly lower in diseased and/or cancerous tissues (Song, Zhou et al. 2013). This expression has been shown to relate to the stage of cancer, with expression further reduced with more advanced cancer. It is thought that miRNA-375 is involved with the regulation of glucose-induced biological responses in pancreatic β-cells, by targeting 3-phosphoinositide—dependent protein kinase-1 (PDK1) mRNA and so affecting the PI 3-kinase/PKB cascade (El Ouaamari et al. Diabetes 57:2708-2717, 2008). An anti-proliferative effect of miRNA-375 is implicated by this putative mode of action, which may explain its downregulation in cancer cells.

In the context of disease-specific expression of introduced polynucleotides, target sequences for any miRNA sequence which is disrupted in a particular disease—that is, unregulated or downregulated in diseased cells (such as tumor cells) in comparison to non-diseased cells—is considered suitable for use in the invention. Table 2 discusses further, non-limiting examples of tumor miRNA that are differentially regulated in tumor versus corresponding healthy tissue, which may be used in embodiments of the present invention. It will be appreciated, however, that the present invention is not limited only to instances where a given miRNA or class of miRNAs is downregulated in a first cell type versus a second cell type within a given organ or organ system. On the contrary, it is merely required that there exists a differential expression pattern of a regulatory miRNA between first and second cell types, for example those comprised within an organ or organ system. The differential expression of the miRNA can be exploited using the compositions and methods described herein to enable corresponding differential translation of protein products in those cells.

Examples of cancers where evidence has been found for similar differential miRNA expression between healthy and cancer cells include breast (Nygaard et al, BMC Med Genomics, 2009 Jun. 9; 2:35), ovarian (Wyman et al, PloS One, 2009; 4(4): e5311), prostate (Watahiki et al, PloS One, 2011; 6(9): e24950), and cervical cancers (Lui et al. Cancer Research, 2007 Jul. 1; 67(13):6031-43). WO 2017/132552 A1 describes a wide range of miRNAs with differing expression levels in various cancer cells. In skin, differential expression miRNA expression between healthy tissue and adjacent melanoma cells is also observed.

TABLE 2

| Tissue/Cancer type | Implicated miRNA | Expression Profile | Reference |
|---|---|---|---|
| Liver | miRNA-122 | Reduced in cancer cells | Braconi et al. Seminars in Oncology. 2011; 38(6): 752-763; Brown and Naldini. Nature Reviews Genetics. 2009; 10: 578-585; Fu and Colin. EBioMedicine. 2018; 17-18. |
| Liver | miRNA-125, miRNA-199 Let7 family | Reduced in hepato-carcinoma | Coppola N et al. Oncotarget, 2017; 8(15): 25289-299 Murakami Y. Oncogene 2006; 25 Hou et al. Cancer Cell, 2011; 19(2): 232-243. Shi et al. Medicine. 2017; 96(32): e7764 |
| Brain | miRNA-124a | Reduced in glioblastoma multiforme | Mazzacurati L. Molecular Therapy 23, 2015; Gaur et al. Cancer Res. 2007; 67(5): 2456-68. |

TABLE 2-continued

| Tissue/Cancer type | Implicated miRNA | Expression Profile | Reference |
|---|---|---|---|
| Lung | Let-7 family miRNA-148a/b miRNA-30 family miRNA-126 | Reduced in cancer cells | Edge R E et al. Mol Ther 2008; 16(8): 1437-43 Lamichhane et al. Disease Markers. 2018; ID8309015 |
| Breast | Let7 family | Reduced in cancer | Yu F. Cell 2007; 11431(6): 1109-23 Takamizawa J. Cancer Res 2004; 64(11): 3753-3756 |
| Pancreas | miRNA-375 Let7 family miRNA-142 miRNA-145 miRNA-217 | Reduced in cancer cells | Song S et al. Biomed Rep. 2013 (3): 393-398 |
| Colon | miRNA-143, -145, -194, -34a, -126, -192, -215, Let7 family | Reduced in cancer cells | Michael M Z. Mol Cancer Res 2003; 334 (1): 882-891; Ding et al. Int. J. Mol. Sci. 2018; 19, 2719 |
| Kidney | miRNA-192, -194, -204, -215, -30 family, -141, -200c | Kidney-specific expression | Sempere et al. Genome Biol 2004; 5(3): R13 Wu et al. Nat. Commun. Apr 4; 7: 11169.; Nakada et al. J Pathol. 2008; 216: 418-427 Jiang et al. Oncology Letters (2018) 16, 3038-3044 |
| Skin | miRNA-877, -4300, -4720, -6761 miR-203a, -205, -200c | Reduced in melanoma vs healthy adjacent tissue Tissue specific and reduced in melanoma vs healthy adjacent tissue | Aksenenko et al. BMC Dermatology. 2019; 19: 1. Liu et al. Laboratory Investigation (2012) 92, 1084-1096 |
| Spleen | miRNA-142 miRNA-126 | Hematopoietic cells specific Decreased or mutated in leukemic cells compared to mature cells | Chen et al. Science (2004); 303(5654): 83-86; Trissal et al. Cancer Res. 2018; 78(13): 3510-3521; Merkerova et al. Eur J Haematol 2008; 81(4): 304-10 |
| Muscle and cardiac muscle | miRNA-1, miR-133a miR-206 | Reduced in infarcted heart tissue, drastically reduced in rhabdomyo-sarcoma, compared to healthy cells Reduced in rhabdomyo-sarcoma | Bostjancic E, et al. Cardiology. 2010; 115(3): 163-169; Rao, Prakash K et al. FASEB J. 2010; 24(9): 3427-3437 Ma et al. Int. J. Biol. Sci. 2015; 11: 345-352. |

Treating patients with immunotherapies like oncolytic viruses or CAR-T therapies may have safety issues due to the possibility of off-target effects. Even the expression of certain polypeptides by the provision of coding mRNA sequences can have negative effects on certain organs. Protecting healthy tissues, for example liver, brain, breast, lung, pancreas, colon/GI-tract, skin, muscle, and kidneys is thus paramount for successful clinical applications. For instance, target sequence for specific miRNA that are highly expressed in specific tissues can be used to protect healthy cells, such as miR-1, miR-133a and/or miR-206 to protect healthy muscle and/or myocardium tissues. As a result, it may be desired to use miRNA target sequences which are not necessarily associated with differential expression in diseased and healthy cells. For example, miRNA-142 and miRNA 145 have expression in pancreatic tissue, while miR-9 can be used for brain and lung protection because of its high expression in these tissues.

If more than one tissue is to be protected, a combination of multiple miRNA target sequences is used. For instance, the target sequence for miR-122, miR-203a, miR-1 and miR-30a is used together to protect cells of the liver, skin, muscle and kidney tissues.

Hence, the present compositions may represent an enabling technology platform for enhancing and facilitating the successful adoption of hitherto 'experimental' cellular or viral therapies.

As is evident from this disclosure, the present invention is envisioned to relate to a number of possible combinations of therapies, delivery platforms (such as different nanoparticle compositions), therapeutic agents (such as drugs, CAR-T cells or viruses), encoded polypeptides and target cells, tissues or organs. Each and all of these possibilities have implications for the optimal expression for the encoded polypeptides supplied by the mRNA sequences.

It has been found that the optimisation of one or more characteristics of the miRNA target sequences can lead to particular efficacy at promoting differential expression and thereby healthy organ protection. By the same token, such characteristics can be controlled to increase or decrease the resultant differential expression in particular organ, tissue or cell types, according to the specific context. There may be situations where a variety of expression levels are desired in various different cell types, and it is intended that target sequences can be modified to allow for such an outcome, by varying one or more characteristics as described herein. Also, an miRNA target site sequence can be modified so it is subject to regulation by more than one miRNA, either within the same tissue or in different tissues.

Sequence Matching: the degree to which the target sequences are an exact match with the complementary miRNA sequence (that is, the number of mismatches between the miRNA sequence and the binding site sequence) has been shown to impact the efficacy of resultant expression silencing. For example, an exact or perfect match has been shown to lead to more rapid degradation of the sequence possessing the miRNA binding site sequence (Brown and Naldini, Nat Rev Genet. 2009; 10(8): 578-585. Therefore, if complete, or close to complete silencing of a particular polypeptide product is required in a particular cell type, it may be desired to select an miRNA target sequence which is an exact match, or has at most no more than one base pair mismatch, with an miRNA sequence associated with that cell type. Likewise, if reduced but not absent expression is desired in a particular cell type, an miRNA binding site sequence with an increased number of mismatches can be chosen to allow for this. Examples of several miRNA sequences mentioned herein, including the sequences of the stem-loop pre-miRNA with the eventual processed mature 5P or 3P miRNA and the sequences which form a duplex with the mature miRNA in the pre-miRNA underlined, as well as the mature miRNA sequences and duplex forming sequences themselves, are shown in Table 3 below. The mature miRNA expressed at significant levels in the cell (which can be either or both of the 5P and 3P strands) is marked (*). Table 4 shows the original, imperfectly matched, target sequence which forms the duplex in the pre-miRNA, followed by the mature miRNA sequence and the development of a modified complementary target sequence, which is designed to be a perfect match with the overexpressed mature miRNA sequence. The modified target sequence in the conventional 5' to 3' orientation is shown in bold.

TABLE 3

Optimisation of the miRNA Target Sequences by
Testing 5P vs 3P Mature Binding Sequences (*overexpressed
mature miRNA from RNA-Seq database http://www.mirbase.org)

| | | Nucleotide Sequence |
|---|---|---|
| miRNA-122 | Pre-miRNA [SEQ ID NO: 2] | 5-CCUUAGCAGAGCUGUGGAGUGUGACAAUGGUGUUUGUGUCU AAACUAUCAAACGCCAUUAUCACACUAAAUAGCUACUGCUAGG C-3 |
| | 5P mature* [SEQ ID NO: 3] | 5-UGGAGUGUGACAAUGGUGUUUG-3 |
| | 3P mature [SEQ ID NO: 4] | 5-AACGCCAUUAUCACACUAAAUA-3 |
| miRNA-199a | Pre-miRNA [SEQ ID NO: 5] | 5-GCCAACCCAGUGUUCAGACUACCUGUUCAGGAGGCUCUCA AUGUGUACAGUAGUCUGCACAUUGGUUAGGC-3 |
| | 5P mature [SEQ ID NO: 6] | 5-CCCAGUGUUCAGACUACCUGUUC-3 |
| | 3P mature* [SEQ ID NO: 7] | 5-ACAGUAGUCUGCACAUUGGUUA-3 |
| miRNA-125a | Pre-miRNA [SEQ ID NO: 8] | 5-UGCCAGUCUCUAGGUCCCUGAGACCCUUUAACCUGUGAGG ACAUCCAGGGUCACAGGUGAGGUUCUUGGGAGCCUGGCGUCUG GCC-3 |
| | 5P mature* [SEQ ID NO: 9] | 5-UCCCUGAGACCCUUUAACCUGUGA-3 |
| | 3P mature [SEQ ID NO: 10] | 5-ACAGGUGAGGUUCUUGGGAGCC-3 |
| miRNA-192 | Pre-miRNA [SEQ ID NO: 11] | 5-GCCGAGACCGAGUGCACAGGGCUCUGACCUAUGAAUUGACA GCCAGUGCUCUCGUCUCCCCUCUGGCUGCCAAUUCCAUAGGUC ACAGGUAUGUUCGCCUCAAUGCCAGC-3 |
| | 5P mature* [SEQ ID NO: 12] | 5-UCUGACCUAUGAAUUGACAGCC-3 |
| | 3P mature [SEQ ID NO: 13] | 5-CUGCCAAUUCCAUAGGUCACAG-3 |
| miRNA-let7b | Pre-miRNA [SEQ ID NO: 14] | 5-CGGGGUGAGGUAGUAGGUUGUGUGGUUUCAGGGCAGUGAUG UUGCCCCUCGGAAGAUAACUAUACAACCUACUGCCUUCCCUG-3 |
| | 5P mature* [SEQ ID NO: 15] | 5-UGAGGUAGUAGGUUGUGUGGUU-3 |
| | 3P mature [SEQ ID NO: 16] | 5-CUAUACAACCUACUGCCUUCCC-3 |

TABLE 3-continued

Optimisation of the miRNA Target Sequences by
Testing 5P vs 3P Mature Binding Sequences (*overexpressed
mature miRNA from RNA-Seq database http://www.mirbase.org)

Nucleotide Sequence

| miRNA-375 | Pre-miRNA [SEQ ID NO: 17] | 5-CCCCGCGACGAGCCCCUCGCACAAACCGGACCUGAGCGUUUUGUUCGUUCGGCUCGCGUGAGGC-3 |
|---|---|---|
| | 5P mature [SEQ ID NO: 18] | 5-GCGACGAGCCCCUCGCACAAACC-3 |
| | 3P mature* [SEQ ID NO: 19] | 5-UUUGUUCGUUCGGCUCGCGUGA-3 |
| miRNA-124a | Pre-miRNA [SEQ ID NO: 20] | 5-AGGCCUCUCUCUCCGUGUUCACAGCGGACCUUGAUUUAAAUGUCCAUACAAUUAAGGCACGCGGUGAAUGCCAAGAAUGGGGCUG-3 |
| | 5P mature [SEQ ID NO: 21] | 5-CGUGUUCACAGCGGACCUUGAU-3 |
| | 3P mature* [SEQ ID NO: 22] | 5-UAAGGCACGCGGUGAAUGCCAA-3 |
| miRNA-143 | Pre-miRNA [SEQ ID NO: 23] | 5-GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC-3 |
| | 5P mature [SEQ ID NO: 24] | 5-GGUGCAGUGCUGCAUCUCUGGU-3 |
| | 3P mature* [SEQ ID NO: 25] | 5-UGAGAUGAAGCACUGUAGCUC-3 |
| miRNA-142 | Pre-miRNA [SEQ ID NO: 26] | 5-GACAGUGCAGUCACCCAUAAAGUAGAAAGCACUACUAACAGCACUGGAGGGUGUAGUGUUUCCUACUUUAUGGAUGAGUGUACUGUG-3 |
| | 5P mature* [SEQ ID NO: 27] | 5-CAUAAAGUAGAAAGCACUACU-3 |
| | 3P mature* [SEQ ID NO: 28] | 5-UGUAGUGUUUCCUACUUUAUGGA-3 |
| miR-203a | Pre-miRNA [SEQ ID NO: 29] | 5-GUGUUGGGGACUCGCGCGCUGGGUCCAGUGGUUCUUAACAGUUCAACAGUUCUGUAGCGCAAUUGUGAAAUGUUUAGGACCACUAGACCCGGCGGGCGCGGCGACAGCGA-3 |
| | 5P mature [SEQ ID NO: 30] | 5-AGUGGUUCUUAACAGUUCAACAGUU-3 |
| | 3P mature* [SEQ ID NO: 31] | 5-GUGAAAUGUUUAGGACCACUAG-3 |

TABLE 3-continued

Optimisation of the miRNA Target Sequences by
Testing 5P vs 3P Mature Binding Sequences (*overexpressed
mature miRNA from RNA-Seq database http://www.mirbase.org)

Nucleotide Sequence

| | | |
|---|---|---|
| Let7a | Pre-miRNA [SEQ ID NO: 32] | 5-UGGGAUGAGGUAGUAGGUUGUAUAGUUUUAGGGUCACACCC ACCACUGGGAGAUAACUAUACAAUCUACUGUCUUUCCUA-3 |
| | 5P mature* [SEQ ID NO: 33] | 5-UGAGGUAGUAGGUUGUAUAGUU-3 |
| | 3P mature [SEQ ID NO: 34] | 5-CUAUACAAUCUACUGUCUUUC-3 |
| miR-30a | Pre-miRNA [SEQ ID NO: 35] | 5-GCGACUGUAAACAUCCUCGACUGGAAGCUGUGAAGCCACAG AUGGGCUUUCAGUCGGAUGUUUGCAGCUGC-3 |
| | 5P mature* [SEQ ID NO: 36] | 5-UGUAAACAUCCUCGACUGGAAG-3 |
| | 3P mature [SEQ ID NO: 37] | 5-CUUUCAGUCGGAUGUUUGCAGC-3 |
| miRNA-1b | Pre-miRNA [SEQ ID NO: 38] | 5-UGGGAAACAUACUUCUUUAUAUGCCCAUAUGGACCUGCUAA GCUAUGGAAUGUAAAGAAGUAUGUAUCUCA-3 |
| | 5P mature [SEQ ID NO: 39] | 5-ACAUACUUCUUUAUAUGCCCAU-3 |
| | 3P mature* [SEQ ID NO: 40] | 5-UGGAAUGUAAAGAAGUAUGUAU-3 |
| miRNA-126 | Pre-miRNA [SEQ ID NO: 41] | 5-CGCUGGCGACGGGACAUUAUUACUUUUGGUACGCGCUGUGA CACUUCAAACUCGUACCGUGAGUAAUAAUGCGCCGUCCACGGC A-3 |
| | 5P mature [SEQ ID NO: 42] | 5-CAUUAUUACUUUUGGUACGCG |
| | 3P mature* [SEQ ID NO: 43] | 5-UCGUACCGUGAGUAAUAAUGCG |

TABLE 4

Optimization of the miRNA Target Sequence by
Modifying the Nucleotides Sequence to Obtain a Perfect Match
with the miRNA (*overexpressed mature miRNA
from RNA-Seq database http://www.mirbase.org)

Nucleotide Sequence

| | | |
|---|---|---|
| miRNA-122 | 3P = sequence within pre-miRNA [SEQ ID NO: 4] | 5-AACGCCAUUAUCACACUAAAUA-3 |
| | Perfect matching [SEQ ID NO: 3] | 5P* 5-UGGAGUGUGACAAUGGUGUUUG-3 |
| | Target Sequence [SEQ ID NO: 44] | TS 3-ACCUCACACUGUUACCACAAAC-5 |
| | Orientated 5' -> 3' [SEQ ID NO: 44] | TS 5-CAAACACCAUUGUCACACUCCA-3 |

TABLE 4-continued

Optimization of the miRNA Target Sequence by
Modifying the Nucleotides Sequence to Obtain a Perfect Match
with the miRNA (*overexpressed mature miRNA
from RNA-Seq database http://www.mirbase.org)

Nucleotide Sequence

| miRNA | | |
|---|---|---|
| miRNA-199a | 5P = Target sequence within pre-miRNA [SEQ ID NO: 6] | 5-CCCAGUGUUCAGACUACCUGUUC-3 |
| | Perfect matching [SEQ ID NO: 7] | 3P* 5-ACAGUAGUCUGCACAUUGGUUA-3 |
| | TS [SEQ ID NO: 45] Orientated 5' -> 3' [SEQ ID NO: 45] | TS 3-UGUCAUCAGACGUGUAACCAAU-5 TS 5-UAACCAAUGUGCAGACUACUGU-3 |
| miRNA-125a | 3P = sequence within pre-miRNA [SEQ ID NO: 10] | 5-ACAGGUGAGGUUCUUGGGAGCC-3 |
| | Perfect matching [SEQ ID NO: 9] | 5P* 5-UCCCUGAGACCCUUUAACCUGUGA-3 |
| | TS [SEQ ID NO: 46] Orientated 5' -> 3' [SEQ ID NO: 46] | TS 3-AGGGACUCUGGGAAAUUGGACACU-5 TS 5-UCACAGGUUAAAGGGUCUCAGGGA-3 |
| miRNA-192 | 3P = sequence within pre-miRNA [SEQ ID NO: 13] | 5-CUGCCAAUUCCAUAGGUCACAG-3 |
| | Perfect matching [SEQ ID NO: 12] | 5P* 5-UCUGACCUAUGAAUUGACAGCC-3 |
| | TS [SEQ ID NO: 47] Orientated 5' -> 3' [SEQ ID NO: 47] | TS 3-AGACUGGAUACUUAACUGUCGG-5 TS 5-GGCUGUCAAUUCAUAGGUCAGA-3 |
| miRNA-let7b | 3P = sequence within pre-miRNA [SEQ ID NO: 6] | 5-CUAUACAACCUACUGCCUUCCC-3 |
| | Perfect matching [SEQ ID NO: 15] | 5P* 5-UGAGGUAGUAGGUUGUGUGGUU-3 |
| | TS [SEQ ID NO: 48] Orientated 5' -> 3' [SEQ ID NO: 48] | TS 3-ACUCCAUCAUCCAACACACCAA-5 TS 5-AACCACACAACCUACUACCUCA-3 |
| miRNA-375 | 5P = sequence within pre-miRNA [SEQ ID NO: 18] | 5-GCGACGAGCCCCUCGCACAAACC-3 |
| | Perfect matching [SEQ ID NO: 19] | 3P* 5-UUUGUUCGUUCGGCUCGCGUGA-3 |
| | TS [SEQ ID NO: 49] Orientated 5' -> 3' [SEQ ID NO: 49] | TS 3-AAACAAGCAAGCCGAGCGCACU-5 TS 5-UCACGCGAGCCGAACGAACAAA-3 |
| miRNA-124a | 5P = sequence within pre-miRNA [SEQ ID NO: 21] | 5-CGUGUUCACAGCGGACCUUGAU-3 |
| | [Perfect matching [SEQ ID NO: 22] | 3P* 5-UAAGGCACGCGGUGAAUGCCAA-3 |
| | TS SEQ ID NO: 50] Orientated 5' -> 3' [SEQ ID NO: 50] | TS 3-AUUCCGUGCGCCACUUACGGUU-5 TS 5-UUGGCAUUCACCGCGUGCCUUA-3 |
| miRNA-143 | 5P = sequence within pre-miRNA [SEQ ID NO: 24] | 5-GGUGCAGUGCUGCAUCUCUGGU-3 |
| | Perfect matching [SEQ ID NO: 25] | 3P* 5-UGAGAUGAAGCACUGUAGCUC-3 |
| | TS SEQ ID NO: 51] Orientated 5' -> 3' [SEQ ID NO: 51] | TS 3-ACUCUACUUCGUGACAUCGAG-5 TS 5-GAGCUACAGUGCUUCAUCUCA-3 |
| miRNA-142 | 5P = sequence within pre-miRNA [SEQ ID NO: 27] | 5-CAUAAAGUAGAAAGCACUACU-3 |
| | Perfect matching [SEQ ID NO: 28] | 3P* 5-UGUAGUGUUUCCUACUUUAUGGA-3 |
| | TS [SEQ ID NO: 52] Orientated 5' -> 3' [SEQ ID NO: 52] | TS 3-ACAUCACAAAGGAUGAAAUACCU-5 TS 5-UCCAUAAAGUAGGAAACACUACA-3 |

TABLE 4-continued

Optimization of the miRNA Target Sequence by
Modifying the Nucleotides Sequence to Obtain a Perfect Match
with the miRNA (*overexpressed mature miRNA
from RNA-Seq database http://www.mirbase.org)

Nucleotide Sequence

| | | |
|---|---|---|
| miR-203a | 5P = sequence within pre-miRNA [SEQ ID NO: 30] | 5-AGUGGUUCUUAACAGUUCAACAGUU-3 |
| | Perfect matching [SEQ ID NO: 31] | 3P*5-GUGAAAUGUUUAGGACCACUAG-3 |
| | TS [SEQ ID NO: 53] Orientated 5' -> 3' [SEQ ID NO: 53] | TS 3-CACUUUACAAAUCCUGGUGAUC-5 TS 5-CUAGUGGUCCUAAACAUUUCAC-3 |
| Let7a | 3P = sequence within miRNA [SEQ ID NO: 34] | 5-CUAUACAAUCUACUGUCUUUC-3 |
| | Perfect matching [SEQ ID NO: 33] | 5P* 5-UGAGGUAGUAGGUUGUAUAGUU-3 |
| | TS [SEQ ID NO: 54] Orientated 5' -> 3' [SEQ ID NO: 54] | TS 3-ACUCCAUCAUCCAACAUAUCAA-5 TS 5-AACUAUACAACCUACUACCUCA-3 |
| miR-30a | 3P = sequence within pre-miRNA SEQ ID NO: 37] | 5-CUUUCAGUCGGAUGUUUGCAGC-3 |
| | Perfect matching [SEQ ID NO: 36] | 5P* 5-UGUAAACAUCCUCGACUGGAAG-3 |
| | TS [SEQ ID NO: 55] Orientated 5' -> 3' [SEQ ID NO: 55] | TS 3-ACAUUUGUAGGAGCUGACCUUC-5 TS 5-CUUCCAGUCGAGGAUGUUUACA-3 |
| miRNA-1b | 5P = sequence within pre-miRNA [SEQ ID NO: 39] | 5-ACAUACUUCUUUAUAUGCCCAU-3 |
| | Perfect matching [SEQ ID NO: 40] | 3P* 5-UGGAAUGUAAAGAAGUAUGUAU-3 |
| | TS [SEQ ID NO: 56] Orientated 5' -> 3' [SEQ ID NO: 56] | TS 3-ACCUUACAUUUCUUCAUACAUA-5 TS 5-AUACAUACUUCUUUACAUUCCA-3 |
| miRNA-126 | 5P = sequence within pre-miRNA [SEQ ID NO: 39] | 5-CAUUAUUACUUUUGGUACGCG-3 |
| | Perfect matching [SEQ ID NO: 40] | 3P* 5-UCGUACCGUGAGUAAUAAUGCG-3 |
| | TS [SEQ ID NO: 57] Orientated 5' -> 3' [SEQ ID NO: 57] | TS 3-AGCAUGGCACUCAUUAUUACGC-5 TS 5-CGCAUUAUUACUCACGGUACGA-3 |

It is known that variants and polymorphisms of miRNA sequences can be found, and that miRNA families exist with similar properties. In the present invention, it is envisioned that all suitable variants and family members of particular miRNA sequences and associated binding sites can be used where appropriate. On the other hand, apparently closely related miRNA sequences can have different expression profiles (Sun et al, World J Gastroenterol. 2017 Nov. 28), so in some situations it will be necessary to determine whether a specific substitution is appropriate, by reference to the literature. For example, Let-7 is part of a wider family with a number of related variants, which can be denoted as Let-7a to Let-7k, and so on. As discussed above, such variants and polymorphisms may vary in their efficacy at allowing for miRNA-mediated silencing, and it is intended that particular selections can therefore be made to allow for the desired level of silencing in a particular cell type.

The presence of a plurality of miRNA target sequences in the mRNA construct enables improved efficacy of the differential expression of the supplied polypeptide or polypeptides. Without being bound by theory, it is thought that with an increased number of target sites, the likelihood of translation inhibition by the miRNA is increased. Multiple miRNA target sites can comprise multiple copies of substantially the same target sequence, thereby introducing redundancy. Alternatively or additionally, the multiple target sequences can comprise substantially different sequences, thereby allowing the mRNA construct to be targeted by more than one species of miRNA. In this way, differential expression of a supplied mRNA construct can be achieved for more than one cell type, and/or in more than one organ, as is evident from the discussion of organs and their associated specific miRNA expression above. Both approaches are considered to be possible within the same sequence or multiple sequences. An intermediate approach is also envisioned, wherein target sites are included which are intended to be targets for the same miRNA sequence, but have differences in order to bind different miRNA variants of the same family, e.g., Let7.

Some advantages associated with the use of multiple target sites include an increase in the efficiency of differential expression of polypeptides supplied by the mRNA sequences of the present invention, within a single organ. Use of different binding site sequences, or sequences which are applicable to more than one tissue or organ type can enable differential expression to be achieved in different cell types in more than one organ or tissue. This may be desirable when systemic administration of compositions according to the invention is used, and it is necessary to avoid off-target effects in more than one organ.

Even with localised or targeted administration, it is possible that supplied mRNA constructs may encounter or accumulate in organs, tissues, and/or cells for which they were not intended. In particular, liver and spleen tissue may accumulate administered compositions, due to the physiological function of these organs. In these cases, to avoid off-target effects, it may be advantageous for the supplied constructs to comprise miRNA target sequences which would enable reduced expression in these tissues. Conversely, it may be desirable for expression to be encouraged in some organs, tissues and/or cell types but not others, which can be achieved by the selection of miRNA target sequences accordingly.

Particular combinations of miRNA target sites can relate to particular combinations of target organs, which may be especially effective in different contexts. For example, administered compositions may accumulate in the liver and spleen, and therefore the use of miRNA target sequences associated with those organs can give directed protection to healthy cells which may be contacted with the compositions. For example, the binding site sequences can provide one or more targets for each of miRNA-122 and miRNA-142, or any other combination of liver and spleen-associated miRNA sequences, for example any combination of those listed for these organs in Table 2. Such combinations could include, for example, at least one copy of at least one target site selected from miRNA-122, miRNA-125, and miRNA-199 (liver); at least one copy of at least one binding site sequence selected from miRNA-192, miRNA-194, miRNA-204, miRNA-215, and miRNA-30 a,b,c (kidney); and at least one copy of a binding site for miRNA-142 (spleen).

Such an approach may be especially advantageous for certain varieties of delivery nanoparticles. For instance, liposome-based nanoparticles may be prone to accumulate in the liver, kidneys and spleen. Other nanoparticle types or alternative administration approaches may accumulate in different organs or tissues, or the targeting of the compositions may cause particular organs or tissues to be in particular need of modulation of expression. For example, intramuscular administration may lead to accumulation in muscle tissue, and subcutaneous administration may lead to accumulation in skin tissue, with effects on which cell types would benefit from protection. It is therefore possible to select generic, likely longer, sequences comprising miRNA binding site sequences which give broad protection from unwanted expression in multiple organs, or to select particular miRNA binding site sequences to allow specific protection in one or more organs as required in a particular situation, which may allow for shorter sequences, and/or the inclusion of repeated binding site sequences (see below). In such a way, the delivered mRNA sequence can be optimised with respect to the mode of delivery (or vice versa).

In some cases, the miRNA target sequences used in the organ protection sequence may not be associated with the tissues or organs to be treated, and may not be designed to lead to differential expression between healthy and diseased cells within said tissues and organs. The miRNA binding sequences may rather be chosen to prevent off-target effects in organs which are not intended to be treated. For example, compositions and methods according to the invention could be designed for the treatment of skin, for instance, for the treatment of melanoma. Application of the compositions to the skin could be topical, or intratumoral (IT), such as by injection directly into the tumor or into blood supply leading directly into the tumor. In such cases, however, the composition could be taken up by the bloodstream, lymphatic system, or by these means or otherwise contact and/or accumulate in organs other than the skin, such as the liver, kidneys and/or spleen. In such cases, the miRNA target sequences may be chosen to accommodate for undesirable biodistribution and to prevent expression of the encoded mRNA within such off-target organs. For instance, the use of miRNA target sequences associated with the liver, kidneys and spleen may be chosen, and so prevent expression within healthy cells comprised within these organs. Examples of potential combinations of miRNA target sequences which could allow for this are set out above.

It is also envisioned that since a perfect match between a binding site sequence and an miRNA sequence is not required for miRNA-mediated silencing to occur, and since some miRNA sequences (especially sequences which are present within similar cell types) have considerable similarity, it is possible that sequences could be devised that could provide a target for more than one miRNA sequence. For example, miR-122 and miR-199 have similar binding site sequences, and a sequence which is substantially complementary to both miRNA could be designed and included as a miRNA target sequence, for example by slightly modifying a miR-122 binding site sequence. In this way, both miR-122 and miR-199 could bind to such a sequence, increasing degradation of the mRNA. Similarly, a target sequence for the Let-7 miRNA could serve as a target sequence for other members of the Let-7 family. Binding site sequences for different miRNAs can be aligned with any suitable alignment technique and compared for shared nucleotides, whereupon a binding site sequence comprising those shared nucleotides can be designed.

In specific embodiments of the invention, the number of times a particular target site sequence is repeated within an mRNA may impact the efficacy of silencing mediated by the binding site sequences. For instance, an increased number of repeats of one miRNA target site can increase the likelihood of the relevant miRNA binding to it, and so the likelihood of translation inhibition or degradation before translation occurs. As a result, if more complete miRNA-mediated silencing is required in a particular cell type, more repeats of a suitable target sequence for an miRNA expressed in those cells can be used. Likewise, reduced but not absent expression can be achieved by including fewer binding site sequences, with or without any of the other approaches discussed herein. Therefore, the same binding site sequence can be provided in the mRNA once, twice, three times, four times, five times, or more, and can be provided alone or in combination with target site sequences for other miRNAs.

According to certain embodiments, the order of the miRNA target sites comprised within the mRNA sequence may affect the resultant organ protection efficacy. For example, the target sequences for miRNA-122, let 7b, miRNA-375, miRNA-192, miRNA-142, (present in liver, lung, breast, pancreas, kidney, and spleen cells) can be presented in this order, or in a number of other permutations, for example:

miRNA-122-miRNA-375-Let 7-miRNA-192-miRNA-142;

miRNA-122-miRNA-375-Let 7-miRNA-142-miRNA-192; or miRNA-122-Let 7-miRNA-375-miRNA-142-miRNA-192.

As another example, the target sequences for miRNA-122, Let 7a, miRNA-142, miRNA-30a, miRNA-143, (present in liver, lung/colon, spleen/haematopoeitic cells, kidney, and colon cells) can be presented in this order, or in a number of other permutations, for example:

miRNA-122-Let7a-miRNA-142-miRNA-30a-miRNA-143;
miRNA-122-miRNA-142-Let7a-miRNA-143-miRNA-30a; or
miRNA-122-miRNA-30a-Let7a-miRNA-143-miRNA-142

In specific embodiments of the invention described in more detail below the target sequences for miRNA-122, miRNA-192 and miRNA-30a (present in liver, colon and kidney) can be presented in a variety of combinations such as:

miRNA-122-miRNA-192-miRNA-30a;
miRNA-122-miRNA-30a-miRNA-192; or
miRNA-192-miRNA-122-miRNA-30a

In further embodiments of the invention described in more detail below the target sequences for Let7b, miRNA-126 and miRNA-30a (present in liver, colon, spleen, lung and kidney) can be presented in a variety of combinations such as:

Let7b-miRNA-126-miRNA-30a;
Let7b-miRNA-30a-miRNA-126; or
miRNA-126-Let7b-miRNA-30a

Such combinations can be useful in protecting tissues likely to be affected by administration of compositions designed to be used in treatments for certain cancers, as discussed herein.

As a further example, the target sequences for miRNA-122, miRNA-203a, miRNA-1, miRNA-30a (present in liver, skin, muscle/myocardium, and kidney) can be presented in this order, or in a number of other permutations, for example:

miRNA-122-miRNA-203a-miRNA-1-miRNA-30a;
miRNA-122-miRNA-1-miRNA-203a-miRNA-30a; or
miRNA-122-miRNA-30a-miRNA-1-miRNA-203a

Such a combination can be useful in protecting tissues likely to be affected by administration of compositions designed to induce an immune response, as discussed below in relation to vaccines and similar approaches.

The present invention therefore allows different approaches to be selected which are tuneable to the coding sequence being delivered by the mRNA, and in which cell types. In other words, the differential expression allowed by the present invention is 'configurable' in order to allow for whatever level of expression or reduced expression is required.

For example, compositions of the invention may be used in conjunction with oncolytic viruses, in order to introduce virulence factors into target cancer cells, to increase the viral activity and lysis within those cells, while using the differential expression made possible by the present invention to prevent expression of those factors in healthy cells. In such cases, the composition of the invention and the oncolytic virus may contact particular cells, organs and tissues, which may be the same or different, depending for example on the nature of each of the composition and the virus, the mode of administration, and any targeting mechanisms which are used. It can be appreciated that it is necessary to reduce expression of the virulence factors only in healthy cells where the composition and the virus are expected to coincide. Cells, organs or tissues which the mRNA of the invention reaches and is expressed in, but which the oncolytic virus would not reach, would be less likely to require reduced expression. Therefore miRNA target sequences can be chosen and tuned with one or more of the approaches as discussed above, in order to allow full expression of the mRNA product in the target cancer cells, and to reduce expression of the mRNA of the invention to the greatest extent possible in the healthy cells which are contacted by both the composition and the virus, with miRNA sequences for other organs less of a priority to include.

For instance, oHSV for treating glioblastoma may be coadministered with mRNA encoding a virulence factor and carrying a target sequence for miR-124a, so that the virulence factor is not expressed in the healthy brain, and the virus can replicate only where the virulence factor is expressed, that is, in the brain tumor. In another example involving oVV and liver, the mRNA construct causes the expression of a virulence factor, but the construct will carry miR-122 or miR-199 so the protein is not expressed in healthy tissue, restricting the effect of the mRNA to tumor cells only.

In another embodiment, the delivered mRNA may code for a immunostimulatory or anti-immunosuppressive protein, or in another way may act to induce an immune response. In such cases, it may be desired to have maximal expression of the encoded product in the target diseased cells, but also to have reduced but still present expression in surrounding healthy tissue of the target organ. On the other hand, it may be desirable for expression of such immune-stimulating products in certain tissues (such as brain or other neural tissue) to be avoided completely, and/or for expression to be reduced in cells, tissues and organs where the composition is likely to accumulate, to prevent off-target immune responses and possible systemic reaction. Therefore, in one example the miRNA target sequences can be determined by one or more of the approaches discussed above to allow full expression in target diseased cells, partially reduce expression in healthy cells in the target organ, while more completely reducing expression in neural tissue and sites of accumulation.

In some embodiments, more than one different mRNA sequence may be provided in a single composition. These different sequences can encode different polypeptides, and/or different miRNA target sites. In this way, a single composition can allow for multiple different polypeptides to be expressed. By using different combinations of miRNA target sequences in the separate mRNA sequences, different cell types or target organs can express, or be protected from the expression of certain polypeptides, according to the desired objective. For instance, if healthy cells in liver and brain must be protected from the expression of a polypeptide 'A', but it is desired to express a polypeptide 'B' in healthy brain, but not liver, a first mRNA sequence could comprise the sequence of 'A', with target sites for miRNA-122, miRNA-125a and miRNA-124a, while a second mRNA sequence could comprise the sequence of 'B', with binding sites for miRNA-122 and miRNA-125a.

It can be appreciated that the person of skill in the art will be able to devise combinations of miRNA target sites, polypeptide sequences and multiple mRNA sequences in order to achieve any combination of expression in a given set of organ and cell types. The relevant organs and tissue types relating to these sequences are discussed above and in Table 2. FIG. 1 shows schematic views of mRNA constructs according to some embodiments of the invention. An ORF is preceded by a start codon and terminated with a stop codon, and a subsequent series of up to five or more binding site sequences are present in the 3'UTR. As shown in FIG. 1, the miRNA target sites (BS1 to BS5) that define the OPS may be separated by spacers, or no spacer at all if preferred. The ORF can code for example for a polypeptide as described herein. Variability in the stop codon is envisioned in any embodiment, and there may in all embodiments be no stop codon between the ORF and the binding site sequences.

The UTR of the mRNA sequences supplied by the present invention can be selected to have similarity, for example greater than 90% similarity, to part or all of a UTR sequence expressed in one of the cell types within the target organ. Particular cell types can have genes which are up- or down-regulated in expression, and the UTR sequence can mediate this regulation, for instance through encouraging the stability or degradation of the relevant mRNA sequences.

As an example, UTRs associated with genes which are known to be upregulated in cancer cells may have one or more features, such as miRNA binding site sequences, which encourage their stability and translation in these cancer cells. By incorporating similar sequences into supplied mRNA sequences, stability and translation can be improved in cancerous cells but not non-cancerous or healthy cells.

It is also considered that the cancer to be treated by the invention may be a secondary cancer in the target tissue, that is, a metastasis from a cancer elsewhere than the target tissue. For example, a liver metastasis might originate from a cancer of the oesophageal, stomach, colon, rectum, breast, kidney, skin, pancreas or lung, and may be adenocarcinoma or another type of cancer. In these cases, alternative miRNA sequences may need to be selected in order to provide differential expression in healthy, non-cancerous and/or cancerous cells. Indeed, there may be an increased choice of candidate miRNA sequences in such cases, due to the different tissue origin of metastasised cells.

In certain situations, it is possible that more than one candidate for an miRNA sequence which exhibits differential expression in different cell types in a target tissue may exist. In such cases, it may be advantageous that a plurality of miRNA target sequences are included in the mRNA construct, and that these sequences may be substantially different sequences. However, it is also envisaged that each of the plurality of miRNA target sequences may be substantially the same sequence.

Combination Therapies
Therapeutic Viruses: Oncolytic Viruses

As mentioned above, oncolytic viral therapy is the process of using therapeutic viruses to infect and kill cancer cells, sometimes by direct viral lysis, but also including indirect killing by the stimulation of host anti-tumoral responses. While oncolytic viruses are frequently characterised by having increased activity in cancer cells compared with healthy cells, off-target effects caused by damage to healthy cells have been documented (Russell et al. Nat. Biotechnol. 2012; 30(7):658-670).

In order to increase safety and decrease off-target effects, oncolytic viruses may be modified or selected to reduce their virulence, for example by the deletion of virulence factors or genes involved in functions such as intracellular immune system suppression and evasion, viral genome replication or transcription, and the takeover of host cell processes. The historical production of safe forms of live viruses for use in vaccination is another source of attenuated viruses. In other cases, particular mutations or even additional genes have been seen to enhance oncolytic activity in particular oncolytic viruses. Non-exhaustive examples of the virulence genes commonly added, mutated or deleted in oncolytic viruses may be found in Table 5.

TABLE 5

| Oncolytic virus | Mutation | Reference |
| --- | --- | --- |
| Vesicular Stomatitis Virus, marabavirus | G protein (Q242R mutation) M protein (L123W mutation) | Brun et al 2010, Mol Ther.; 18(8): 1440-1449. |
| Vaccinia virus | Ribonucleotide reductase (RR1, RR2) inactivation Thymidine kinase (TK) inactivation A56R inactivation | Buller et al. Nature (London) 1985; 317. Puhlamm M et al. Cancer Gene Ther 2000; 7 Slabaugh M B et al. J Virol 1984; 52 |
| Measles virus | NIS gene-Human thyroidal iodide symporter | Aref et al 2016, Viruses, 8, 294 |
| Newcastle disease virus | Fusion protein (F) cleavage site | Vigil et al 2007 Cancer Res; 67: (17). Marchini et al 2015 |
| Parvovirus | NS protein NS1 | Virology Journal 12: 6 |
| Herpes Simplex Virus Type 1 (HSV-1) | Viral ribonucleotide reductase (ICP6) inactivation; serine/threonine-protein kinase (US3) inactivation; ICP34.5 and ICP47 inactivation (Neurovirulence and immune system evasion); UL43 inactivation (Cell fusion) inactivation; UL49.5 inactivation (T-cell evasion) inactivation; UL55 and UL56 | Liu et al (2003) Gene Therapy volume 10, 292-303; Goldsmith et al 1998 J Exp Med. 187(3): 341-348; |
| Adenovirus | E1B-55, E3, E1a promoter, E3 gp19kD, E1A 924bp), E1A, deletion in E3 and E4, E3 quaitotal deletion, chimeric ad3/Ad11p E2B region, E3-6.7K + gp19K E1A, ChAdOx1, ChAdOx2 | Baker et al 2018, Cancers, 10, 201 |

The attenuation or modification of oncolytic viruses in this way can play a role in the selectivity of oncolytic viruses to cancer cells: since the process of carcinogenesis often involves the inactivation of genes that play protective roles against both cancer (such as by regulating cell division or apoptosis), and viral infection, oncolytic viruses which are attenuated as described can retain their virulence in cancer cells, due to the absence of the usual antiviral genes in these cells. Therefore, in healthy cells the attenuated virus cannot defend against the normal antiviral responses, and is eliminated, whereas in cancer cells this response is absent, and the virus can lyse the cells. However, this approach is rarely completely effective, as firstly partial inactivation of antiviral responses in cancer cells is more common than a complete lack of antiviral activity (Haralambieva et al, Mol. Ther., 2007; 15(3): 588-597), meaning that virulence can still be reduced in these cells, and secondly infection of healthy cells can still occur.

Similarly, as viruses typically utilise the cellular machinery of the host cell in order to replicate their genomes, but this machinery is typically downregulated in healthy, quiescent, non-replicating cells which are not replicating their own genomes, many viruses possess genes which compensate for the host machinery. For example, ribonucleotide reductase enzymes are necessary for the production of deoxyribonucleotides from ribonucleotides; these enzymes are typically downregulated in quiescent host cells, and several viruses possess genes for their own enzyme of this type, in order to have a source of deoxyribonucleotides. Since replicating cancer cells may have the expression of these enzymes unregulated, an attenuated oncolytic virus with its own ribonucleotide reductase enzyme gene deleted can still replicate in cancer cells. However, for reasons similar to the above, this approach may not be completely effective, either in protecting healthy cells from infection, or in restoring virulence in cancer cells. For example, not all cells in a tumor are replicating at any given time, and as such sufficient deoxyribonucleotides may not be available for viral replication in the majority of cancer cells.

Following the above, when a composition or method according to the present invention is used in conjunction with oncolytic viral therapy, the therapeutic enhancement factor provided by the constructs of the invention may be a factor which increases the efficacy of the oncolytic virus in cancer cells, for example enhancing replication of the virus, or the ability of the virus to lyse the cells in which it resides. In particular, where the oncolytic virus has been modified to attenuate its function, for example by the deletion of one or more genes for virulence factors, the therapeutic factor may replace the deleted gene with mRNA for a gene product which is a copy of the viral gene product, or a gene product with substantial homology to the deleted gene, or which otherwise compensates for the deletion of the gene. In such embodiments, by the differential expression in healthy and cancerous cells which is made possible by the invention, the replacement gene product can be expressed only in cancer cells, enhancing viral activity and lysis in these cells, rather than in healthy cells, where expression of the provided mRNA is inhibited by the presence of the miRNA target sites.

By similar means, mRNA coding for factors which increase the resistance of cells to oncolytic viruses can be expressed preferentially in healthy cells, again promoting viral activity in cancerous cells compared to healthy cells.

A benefit of this approach is that, unlike previous therapies using oncolytic viruses, it does not rely on which cellular antiviral genes and processes may be inactivated due to carcinogenesis, nor on cell replication processes which may be activated in some cancer cells but not others. As a result, a greater scope of which virulence genes can be deleted from oncolytic viruses is allowed. Thus, oncolytic viruses can be modified to completely lack replicative ability in healthy cells, and, in cancer cells where the function of the deleted virulence genes are replaced by means of the invention, the virus can be restored to full potency. As a result, side effects can be reduced, and efficacy increased. Similarly, since the differential expression of the provided mRNA relies on miRNA expression differences between cancer and healthy cells, virulence can be restored in all transfected cancer cells, and not only those that, for example, are undergoing replication at time of administration.

In a particular embodiment, the oncolytic virus is HSV-1, part of the herpesvirus family. Attenuated versions of HSV may be engineered or selected to be deficient in ICP6, which encodes a viral ribonucleotide reductase (Aghi et al, Oncogene. 2008; 27(30): 4249-4254) and/or in US3, which encodes a serine/threonine-protein kinase, and plays several roles in the virus' lifecycle, including blocking host cell apoptosis (Kasuya et al, Cancer Gene Therapy, 2007; 14(6): 533-542).

In another embodiment, the oncolytic virus is part of the poxvirus family, in particular, it may be Vaccinia virus. Attenuated versions of Vaccinia may be engineered or selected to be deficient in one or more subunit of ribonucleotide reductase (RR1 and RR2) and/or in thymidine kinase (TK) (Buller et al. Nature (London) 1985; (317): 813-815; Puhlmann M et al. Cancer Gene Ther 2000; 7(1): 66-73; Slabaugh M B et al. J Virol 1984; 52(2): 507-514).

An alternative or additional approach which can be used with oncolytic viruses involves the provision of viral entry receptors. For viruses to complete their life cycle they, or at least their genomes, must enter into a host cell. This entry is thought to require the binding of one or more viral protein present on the viral capsid or viral envelope if present, to one or more viral entry receptor on the surface of the target host cell. This is followed by viral entry into the cell, for example by membrane fusion, endocytosis or genetic injection. Binding between viral proteins and viral entry receptors may act only to bring the virus into proximity with the cell, and/or may mediate the entry of the virus more directly. Viral entry receptors generally serve a purpose for the cell which expresses them, frequently related to cellular adhesion. The viral proteins present on a virus and the viral entry receptors to which they bind often dictate the cells which it is competent to infect.

In the present context, compositions according to the invention can be used to provide mRNA to target cells such that the cells produce particular viral entry receptors. The cells may then display these viral entry receptors on the cell surface. This can allow viruses to bind to these receptors, undergo cell entry, and replicate and/or lyse within the cells. By the differential expression enabled by the present invention, the expression of these viral entry receptors can be restricted to particular cell, tissue and/or organ types (such as diseased cells within a particular tissue), while other cell, tissue and/or organ types (such as healthy cells or off-target organs) can be protected by preventing them from expressing the viral entry receptors.

For example, herpes simplex virus (HSV) is thought to enter a target cell by initial interaction of its viral envelope glycoproteins glycoprotein C (gC) and glycoprotein B (gB) with heparan sulfate-containing proteoglycans (HSPGs). (Agelidis and Shukla, Future Virol. 2015 Oct. 1; 10(10): 1145-1154. doi:10.2217/fvl.15.85). Subsequently, glycoprotein D (gD) binds to one or more of three known major viral entry receptors, namely herpes virus entry mediator (HVEM), 3-O-sulfated Heparan Sulfate (3-OS HS), or nectin-1 (with HSV-2 also able to bind nectin-2). This binding drives recruitment of a fusion complex including other glycoproteins gB, gH and gL, and eventually fusion of the viral envelope with the plasma membrane. As a result, in some embodiments the mRNA of the invention may encode viral entry receptors for gD, such as one or more of the group consisting of HVEM or a nectin such as nectin-1 or nectin-2. Receptors that bind gB other than via heparan sulfate-containing protein have also been discovered, such as paired immunoglobulin-like receptor (PILRα), an inhibitory receptor found on monocytes, macrophages and dendritic cells, myelin-associated glycoprotein (MAG), and non-muscle myosin heavy chain (NMHC)-IIA (Agelidis and Shukla). Accordingly, in some embodiments, the mRNA of the invention may encode viral entry receptors for gB, such as one or more of the group consisting of PILRα, NMHC-IIA, and MAG.

For Vaccinia virus, which is the prototype poxvirus, there are two main infectious forms of the virus: the mature virion (MV), which has a single membrane, and the extracellular enveloped virion (EV), which has an additional outer membrane that is disrupted prior to fusion. Vaccinia MVs can enter the cell at neutral pH at the plasma membrane or through an endocytic route at low pH. EVs shed their outer membrane at the cell surface allowing MV-like particles to fuse with the plasma or endosomal membrane following macropinocytosis. Then the Vaccinia MVs attached to the host cell via interaction of four viral proteins: viral protein D8, A27 and H3 bind cellular glycoaminoglycans such as heparan sulfate and chondroitin, and viral protein A26 binds the cell surface extracellular matrix protein laminin (Moss, Viruses. 2012; 4(5): 688-707; Chiu et al. *J Virol.* 2007; 81(5): 2149-2157). In some embodiments the mRNA of the invention may encode an extracellular laminin to promote the virus attachment.

By this method, it is possible to induce expression in target cells of viral entry receptors which are not usually expressed or are not usually overexpressed by that cell type, in order to allow infection only of cells which successfully express the polypeptide encoded by the mRNA of the invention. This can mitigate the risk of the virus infecting non-target cells. Viruses may therefore be chosen which, in order to infect a cell, require viral entry receptors which are comparatively rare or absent in healthy cells naturally present within the subject. For instance, when a human is to be treated, the virus may require a viral entry receptor which is never naturally found on a human cell, so as to entirely prevent viral entry into cells which do not express the supplied mRNA.

In addition, the viral entry receptor encoded can be modified, synthesised and/or engineered so that it is effectively bound by the virus provided. Similarly, the virus itself can also or alternatively be designed so that the viral protein which binds to the viral entry receptor is modified, synthesised and/or engineered, to prevent it from binding to viral entry receptors other than those encoded by the mRNA of the invention. In this way, it is also possible to design, modify or synthesise a unique pairing of viral protein and viral entry receptor which is not present in nature, in order to prevent the virus from infecting any cells other than those which express the mRNA of the invention.

In a further embodiment of the invention the ORF within a nucleic acid construct as defined herein may encode a protein that decrease a host anti-viral response. This may be beneficial in instances where therapeutic oncovirus is depressed or eliminated by a host immune response. In one embodiment, the ORF expresses a B18R protein (Accession No. YP_233081). The B18R gene is a vaccinia viral gene that encodes a type I interferon-binding protein that blocks interferon alpha transmembrane signalling. Hence, expression of B18R in diseased or cancerous cells but not in healthy primary cells may assist in persistence and replication of a co-administered oncolytic virus.

Cytokines

It is contemplated that the compositions and methods as described herein may act to induce an immune response against disease or infection from a pathogenic organism. In particular, immune responses may be induced against cancer cells. The process of carcinogenesis frequently involves ways in which the cancer cells attempt to evade the immune system, involving changes to the antigens produced and displayed by these cells, In some embodiments, the mRNA provided by the invention comprises at least one polynucleotide encoding a protein that is a bispecific T-cell engager (BiTE), an anti-immunosuppressive protein, or an immunogenic antigen. The term "anti-immunosuppressive protein" as used herein is a protein that inhibits an immunosuppressive pathway.

The invention encompasses compositions supplying mRNA coding for an anti-immunosuppressive protein that is an anti-regulatory T-cell (Treg) protein or an anti-myeloid-derived suppressor cell (MDSC) protein. In some embodiments, the anti-immunosuppressive protein is a VHH-derived blocker or a VHH-derived BiTE.

The term "immunogenic antigen" as used herein refers to a protein that increases an inflammatory or immunogenic immune response. In particular embodiments, the anti-immunosuppressive and immunogenic antigens induce an anti-tumor immune response. Examples of such proteins include antibody or antigen binding fragments thereof that bind to and inhibit immune checkpoint receptors (e.g., CTLA4, LAG3, PD1, PDL1, and others), proinflammatory cytokines (e.g., IFNγ, IFNα, IFNβ, TNFα, IL-12, IL-2, IL-6, IL-8, GM-CSF, and others), or proteins that binding to and activate an activating receptor (e.g., FcγRI, Fcγlla, FcγIIIa, costimulatory receptors, and others). In particular embodiments, the protein is selected from EpCAM, IFMβ, anti-CTLA-4, anti-PD1, anti-PDL1, A2A, anti-FGF2, anti-FGFR/FGFR2b, anti-SEMA4D, CCL5, CD137, CD200, CD38, CD44, CSF-1R, CXCL10, CXCL13, endothelin B Receptor, IL-12, IL-15, IL-2, IL-21, IL-35, ISRE7, LFA-1, NG2 (also known as SPEG4), SMADs, STING, TGFβ, VEGF and VCAM1.

The invention encompasses compositions supplying mRNA coding for functional macromolecules to targeted cell populations used in cell-based therapies. In some embodiments, the targeted cell population is a genetically engineered T cell population. In some embodiments, the targeted cell population is a population of chimeric antigen receptor T cells (CAR-T cells).

The coding mRNA may be used to attract a population of immune cells or a combination of immune cell populations to a particular site in a subject. In some embodiments, the coding mRNA and the delivery particles are used to attract immune cells to the tumor microenvironment. In some embodiments, the coding mRNA and the delivery particles are used to overcome insufficient migration of an immune cell to the tumor microenvironment. In some embodiments, the immune cell is a T cell, a natural killer (NK) cell, a B cell, an antigen-presenting cell (APC) such as a macrophage or dendritic cell, or any combination thereof. In some embodiments, the coding mRNA and the delivery particles are used to attract CAR-T cells to the tumor microenvironment.

The coding mRNA may be used to overcome insufficient migration of CAR T cells to the tumor microenvironment. In some embodiments, the delivery particles specifically target the tumor microenvironment, and the coding mRNA encodes a gene product that attracts or otherwise recruits CAR-T cells to the tumor microenvironment. In some embodiments, the coding mRNA expresses a chemokine. By way of non-limiting example, the coding mRNA can encode a chemokine that attracts T-cells such as CCL2, CCL3, CCL4, CCL5, CCL20, CCL22, CCL28, CXCL8, CXCL9, CXCL10, CXCL11, CXCL12, XCL1, and any combination thereof. In situations where the reverse effect is desired, such as in autoimmune disease, the coding mRNA can express blockers, antagonists and/or inhibitors of the above-mentioned factors.

The coding mRNA may be delivered to and transiently expressed within the tumor microenvironment. In some embodiments, the coding mRNA encodes a cytokine or other gene product involved in regulating the survival, proliferation, and/or differentiation of immune cells in the tumor response, such as, for example, activated T cells and NK cells. By way of non-limiting example, the coding mRNA can encode for a cytokine such as IL-1, IL-2, IL-3, IL-4, IL-5, IL-6, IL7, IL-8, IL-9, IL-10, IL-11, IL-12, IL-17, IL-33, IL-35, TGF-beta, and any combination thereof. Again, in situations where the reverse effect is desired, such as in autoimmune disease, the coding mRNA can express blockers, antagonists and/or inhibitors of the above-mentioned factors, for example, inhibitors of TGF-beta.

The compositions supplying mRNA may be designed to target particular cell subtypes and, upon binding to them, stimulate receptor-mediated endocytosis, thereby introducing the synthetic mRNA they carry to the cells, which can now express the synthetic mRNA. Because nuclear transport and transcription of the transgene are not required, this process is fast and efficient.

In some embodiments, the coding mRNA may code for receptors or other cell surface proteins associated with immune cells (such as costimulators) or immune pathways, or for molecules which target such receptors. For example, the coding mRNA may code for molecules targeting the following cellular receptors and their ligands selected from one or more of: CD40, CD40L, CD160, 2B4, Tim-3, GP-2, B7H3 and B7H4. Similarly, the coding mRNA may code for dendritic cell activators selected from one or more of GM-CSF, TLR7 and TLR9. In one embodiment, the coding mRNA codes for one or more T-cell membrane protein 3 inhibitors. In one embodiment, the coding mRNA codes for one or more inhibitors of NF-κB.

The Toll-like receptor (TLR) family are involved in pathogen recognition and the activation of innate immunity. TLR8 in particular can recognise single stranded RNA and therefore plays a role in the recognition of ssRNA viruses by the activation of the transcription factor NF-κB and an antiviral response. Therefore, embodiments where the coding mRNA encodes a member of the TLR family, for example TLR8, are considered where an antiviral response is desired.

In some embodiments, the mRNA delivery system delivers an mRNA that codes for a gene-editing agent to a target cell population. In some embodiments, the mRNA codes for a sequence-specific nuclease that targets a gene locus and disrupts expression of one or more endogenous gene produces in the target cell population. In some embodiments, the mRNA codes for a sequence-specific nuclease that targets a T cell receptor (TCR)-related gene locus, thereby disrupting expression of one or more domains in the TCR. Suitably a T cell receptor type protein includes MHC class I-related protein (MR1), as described further in the Examples below.

In some embodiments, the mRNA delivery systems may be used to deliver an mRNA that codes for one or more agents that program engineered T cells toward a desired phenotype. In some embodiments, the mRNA nanoparticle delivery compositions may be used to induce markers and transcriptional patterns that are characteristic of a desired T cell phenotype. In some embodiments, the mRNA nanoparticle delivery compositions may be used to promote development of CD26L+ central memory T cells (Tcm), which have been shown to improve CAR-T treatment. (See e.g., Moffett, Coon supra). In some embodiments, compositions supply mRNA encoding one or more transcription factors to control cell differentiation in a target cell population. In some embodiments, the transcription factor is Foxo1, which controls development effector-to-memory transition in CD8 T-cells.

In some embodiments, the mRNA delivery compositions include a surface-anchored targeting domain that is specific for a T cell marker, such as, for example, a surface antigen found on T cells. In some embodiments, the surface-anchored targeting domain is specific for an antigen that selectively binds the nanoparticle to T-cells and initiates receptor-induced endocytosis to internalize the mRNA nanoparticle delivery compositions. In some embodiments, the surface-anchored targeting domain selectively binds CD3, CD8, or a combination thereof. In some embodiments, surface-anchored targeting domain is or is derived from an antibody that selectively binds CD3, CD8, or a combination thereof.

By means of the invention, differential expression of the above-mentioned gene products can be achieved in different cell types, for example, in healthy cells, non-diseased, diseased and cancer cells. By this method, an immune response can be triggered targeted towards diseased cells while sparing the non-diseased or healthy cells.

The introduction of coding nucleotide sequences into a target cell often requires the use of a delivery agent or 'in vivo delivery composition' to transfer the desired substance from the extracellular space to the intracellular environment. Frequently, such delivery agents/compositions may comprise delivery particles. Delivery particles may undergo phagocytosis and/or fuse with a target cell. Delivery particles may contain the desired substance by encapsulation or by comprising the substance within a matrix or structure.

The term 'delivery particle' as used herein refers to particles which can comprise therapeutic components by encapsulation, holding within a matrix, the formation of complex or by other means, and deliver a therapeutic component such as a coding nucleic acid sequence into a target cell. Delivery particles may on the micro-scale, but in specific embodiments may typically be on the nanoscale—i.e., nanoparticles. Nanoparticles are typically sized at least 50 nm (nanometres), suitably at least approximately 100 nm and typically at most 150 nm, 200 nm, although optionally up to 300 nm in diameter. In one embodiment of the invention the nanoparticles have a mean diameter of approximately at least 60 nm. An advantage of these sizes is that this means that the particles are below the threshold for reticuloendothelial system (mononuclear phagocyte system) clearance, i.e., the particle is small enough not to be destroyed by phagocytic cells as part of the body's defence mechanism. This facilitates the use of intravenous delivery routes for the compositions of the invention.

Alternative possibilities for the composition of the nanoparticles include polylactic acid (PLA), poly(lactic-co-glycolic acid) (PLGA), a lipid- or phospholipid-based particles such as liposomes or exosomes; particles based on proteins and/or glycoproteins such as collagen, albumin, gelatin, elastin, gliadin, keratin, legumin, zein, soy proteins, milk proteins such as casein, and others (Lohcharoenkal et al. BioMed Research International; Volume 2014 (2014)); colloidal nanoparticles; and particles based on metals or metallic compounds such as gold, silver, aluminium, copper oxides, metal-organic cycles and cages (MOCs) and so on.

In particular, polymers comprising polyethyleneimine (PEI) have been investigated for the delivery of nucleic acids. Nanoparticle vectors composed of poly(ß-amino esters) (PBAEs) have also been shown to be suitable for nucleic acid delivery, especially in coformulation with polyethylene glycol (PEG) (Kaczmarek J C et al Angew Chem Int Ed Engl. 2016; 55(44): 13808-13812). Dendrimers are also contemplated for use. Particles of such coformulations have been used to deliver mRNA to the lung.

Also considered are particles based on polysaccharides and their derivatives, such as cellulose, chitin, cyclodextrin, and chitosan. Chitosan is a cationic linear polysaccharide obtained by partial deacetylation of chitin, with nanoparticles comprising this substance possessing promising properties for drug delivery such as biocompatibility, low toxicity and small size (Felt et al., Drug Development and Industrial Pharmacy, Volume 24, 1998—Issue 11). It is envisioned that combinations between the above constituents may be used.

The delivery particles may comprise aminoalcohol lipidoids. These compounds may be used in the formation of particles including nanoparticles, liposomes and micelles, which are particularly suitable for the delivery of nucleic acids. An illustrative example for the production of nanoformulations comprising particles according to some embodiments of the invention may be found in the Examples.

The delivery particles may be targeted to the cells of the target tissue. This targeting may be mediated by a targeting agent on the surface of the delivery particles, which may be a protein, peptide, carbohydrate, glycoprotein, lipid, small molecule, nucleic acid, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, aptamers, etc.

When administered to a subject, a therapeutic component is suitably administered as part of the in vivo delivery composition and may further comprise a pharmaceutically acceptable vehicle in order to create a pharmaceutical composition. Acceptable pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilising, thickening, lubricating and colouring agents may be used. When administered to a subject, the pharmaceutically acceptable vehicles are preferably sterile. Water is a suitable vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. Pharmaceutical compositions, if desired, can also contain minor amounts of wetting or emulsifying agents, or buffering agents.

The medicaments and pharmaceutical compositions of the invention can take the form of liquids, solutions, suspensions, gels, modified-release formulations (such as slow or sustained-release), emulsions, capsules (for example, capsules containing liquids or gels), liposomes, microparticles, nanoparticles or any other suitable formulations known in the art. Other examples of suitable pharmaceutical vehicles are described in Remington's Pharmaceutical Sciences, Alfonso R. Gennaro ed., Mack Publishing Co. Easton, Pa., 19th ed., 1995, see for example pages 1447-1676.

For any compound or composition described herein, the therapeutically effective amount can be initially determined from in vitro cell culture assays. Target concentrations will be those concentrations of active component(s) that are capable of achieving the methods described herein, as measured using the methods described herein or known in the art.

As is well known in the art, therapeutically effective amounts for use in human subjects can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

It is contemplated that embodiments of the invention may include compositions formulated for use in medicine. As such, the composition of the invention may be suspended in a biocompatible solution to form a composition that can be targeted to a location on a cell, within a tissue or within the body of a patient or animal (i.e., the composition can be used in vitro, ex vivo or in vivo). Suitably, the biocompatible solution may be phosphate buffered saline or any other pharmaceutically acceptable carrier solution. One or more additional pharmaceutically acceptable carriers (such as diluents, adjuvants, excipients or vehicles) may be combined with the composition of the invention in a pharmaceutical composition. Suitable pharmaceutical carriers are described in 'Remington's Pharmaceutical Sciences' by E. W. Martin. Pharmaceutical formulations and compositions of the invention are formulated to conform to regulatory standards and can be administered orally, intravenously, topically, intratumorally, or subcutaneously, or via other standard routes. Administration can be systemic or local or intranasal or intrathecal. In particular, compositions according to the invention can be administered intravenously, intralesionally, intratumorally, subcutaneously, intra-muscularly, intranasally, intrathecally, intra-arterially and/or through inhalation.

Further intended are embodiments wherein the composition of some embodiments of the invention is administered separately to or in combination with alternative antitumoral or otherwise anti-cancer therapeutic components. These components can include oncolytic viruses, small molecule drugs, chemotherapeutics, radiotherapeutics or biologicals. The components may be administered concurrently with the composition of the invention, and may be comprised within delivery particles, or may be administered separately, before or after administration of the composition of the invention, by any means suitable.

It is also contemplated that the composition of some embodiments of the invention may be used in in vitro and/or ex vivo methods, for example in a laboratory setting. An example of an in vitro method is wherein a composition including a delivery system comprising an mRNA sequence as described herein is administered to target in vitro cells, and the miRNA binding site sequences comprised in the mRNA sequence allow for differential expression of the coding sequence of the mRNA in different cell types within the target in vitro cells. Similarly, a method is contemplated wherein a composition comprising a delivery system and an mRNA sequence as described herein is administered to a target ex vivo sample taken from an animal, and the miRNA binding site sequences comprised in the mRNA sequence allow for differential expression of the coding sequence of the mRNA in different cell types within the target sample.

Vaccines mRNA constructs and compositions as described herein can be used in vaccine therapy, in the enhancement of the efficacy of a conventional vaccine, and/or as a novel vaccine form for use against infectious pathogens, such as viruses, bacteria, fungi, protozoa, and helminths (worms); or for use in treating diseases such as cancer.

In some embodiments, the coding mRNA can code for an antigen against which an immune response is desired. Delivery of such antigens can be used to induce a local immune response as discussed above, or in order to provoke an adaptive immune response to the antigen itself—that is, to induce immunity against that antigen, similar to a vaccine. In such cases, the compositions according to the invention may be combined with adjuvants to encourage the generation of an immune response. Suitably, one or more proinflammatory cytokines may be utilised as an adjuvant—e.g., selected from: IFNγ; IFNα; IFNβ; TNFα; IL-12; IL-2; IL-6; IL-8; and GM-CSF.

Prophylactic Vaccine to Prevent Infectious Diseases or to Prevent Pathogen Infection For example, the coding mRNA can encode a bacterial, viral or otherwise microbial protein against which an immune reaction is desired, in whole or part. In some cases, immunity can be generated against only part of a bacterial, viral or otherwise microbial protein, so the encoding of only those parts is also envisaged. In particular, parts of a microbial protein which are displayed externally can be selected as likely targets for immune recognition. In some embodiments, the coding mRNA can encode one or more viral proteins of the Severe acute respiratory syndrome coronavirus 2 virus (SARS-CoV-2), that is, the virus responsible for the Covid-19 pandemic. This virus has four structural proteins, the S (spike), E (envelope), M (membrane), and N (nucleocapsid) proteins. In some embodiments, the coding mRNA encodes all or part of the spike protein of SARS-CoV-2. In some embodiments, the mRNA encodes the prefusion form of the S protein ectodomain (amino acids 1 to 1208 with proline substitutions at residues 986 and 987; GenBank MN908947). In some embodiments, the mRNA encodes the Spike protein's Receptor Binding Domain or RBD (residues 319 to 591; GenBank MN908947). As an external part of this protein, this is a likely location for epitopes which could be recognised by the immune system. In a particular embodiment, the coding mRNA additionally comprises at least one organ protection sequence (OPS), wherein the OPS sequence comprises at least a first, a second and a third micro-RNA (miRNA) target sequence. One of the target sequences can be a sequence capable of binding with miRNA-1. The target sequences can comprise sequences capable of binding with one or more of miRNA-1, miR-133a, miR-206, miRNA-122, miR-203a, miR-205, miR-200c, miR-30a, and/or let7a/b, suitably with all of these.

It can be appreciated that the above-mentioned approach is particular suitable for preparing vaccine therapeutic compositions similar to typical 'toxoid' vaccines, where an immune response is induced against an inactivated toxin produced by a bacterium or other organism, or 'subunit' vaccines, where an immune response is induced against a fragment of a target micro-organism.

While any embodiment of the invention described herein may have, as a proposed target tissue, the blood or subdivisions thereof (such as hematopoietic cells, lymphoid cells, and so on), it is particularly considered that the blood and subdivisions thereof may be particularly appropriate in embodiments where the aim is to induce an immune response, where an immune response is to be induced against the product encoded by the coding mRNA, and/or optionally where the aim is to provide a vaccine therapy. Peripheral blood mononuclear cells (PBMC) are particularly contemplated as targets for such approaches, and suitably, antigen presenting cells (APC).

Conventional vaccines function, at least in part, by presenting pathogen-specific antigen to the immune system (exogenous antigen), so that an immune reaction can be induced against it, and so that this exogenous antigen can be recognised and rapidly countered when it is next encountered. So-called antigen presenting cells (APC) are key to this process. While all nucleated cells can present endogenous antigen to cytotoxic T cells (CD8+), certain cells are 'professional' APC, including dendritic cells, macrophages and B cells, with the ability to detect and present exogenous antigens. These cells internalise and process exogenous antigens, and present them or fragments of them (immunodominant epitopes) on the surface, in association with major histocompatibility complexes type II (MHC-II), and often co-stimulatory molecules, to shape an enhanced T cells responses, such as CD4+ helper T cells, that play pivital role in initiating B cells driven antibody production (adaptive immunity).

Previous efforts have demonstrated that mRNA encoding influenza proteins can be administered in lipid nanoparticles, leading to recruitment of immune cells and the translation of the mRNA by monocytes and dendritic cells (Liang et al Efficient Targeting and Activation of Antigen-Presenting Cells In vivo after Modified mRNA Vaccine Administration in Rhesus Macaques. *Mol Ther.* 2017). Therefore, transfection of professional APCs (such as monocytes and dendritic cells) with mRNA constructions or compositions as described herein encoding exogenous antigens or epitopes thereof is contemplated to allow for antigen presentation, and the induction of long-lasting adaptive immunity against that antigen. However, expression of antigen within the professional APC is not necessary, and expression of antigen by other tissue can be effective in inducing a desired immune response, as produced antigen can be taken up and processed by professional APC in the normal way after production.

In addition or instead of this, mRNA constructions or compositions as described herein can be used to deliver and express products associated with the process of vaccine-induced immunity, such as cytokines, chemokines, co-stimulatory molecules, or major histocompatibility complexes. If mRNA coding for both antigen and further components are administered, these can be formulated as separate mRNA constructs, or together on the same, polycistronic mRNA, as described above. It can be appreciated that mRNA encoding such products associated with the process of vaccine-induced immunity can be used in combination with any type of vaccine, i.e., combination with protein-based (toxoid, recombinant, conjugated vaccines), mRNA and DNA-based vaccines, live-attenuated vaccines, inactivated vaccines, or recombinant-vector based vaccines (e.g., MVA or adenovirus platform).

For example, macrophages require activation by T-cell secretion of interferon gamma (IFN-γ) in order to express Therefore, induction of IFN-γ expression by transfection with mRNA constructs and compositions as described can enhance the induction of a vaccine-induced immune response, whether resulting from a conventional vaccine approach or an approach using mRNA constructs and compositions as described herein to induce antigen expression. Similarly, the induction of cell receptors involved in immunogenic processes such as TLR, suitably TLR8 as discussed above, can also be carried out using mRNA constructs and compositions as described herein.

IL-12 is produced by dendritic cells, macrophages, neutrophils, and human B-lymphoblastoid cells in response to antigenic stimulation, and is involved in the stimulation and growth of T cells. IL-12 is a pro-stimulatory and proinflammatory cytokine with key roles in the development of the Th1 subset of helper T cells. IL-12 was originally discovered because of its ability to induce interferon-gamma (IFN-γ) production, cell proliferation, and cytotoxicity mediated by natural killer cells and T cells. It is now established that IL-12 also plays a key role in the development of Th1 responses, leading to IFN-γ and IL-2 production. These cytokines can in turn promote cytotoxic T-cell responses and macrophage activation. Therefore, in another embodiment, it may be desired to administer mRNA constructs and/or compositions leading to IL-12 expression in order to enhance vaccine potency or enhance a vaccine-induced immune response, whether resulting from a conventional vaccine approach or an approach using mRNA constructs and compositions as described herein to induce exogenous antigen expression.

Granulocyte-macrophage colony-stimulating factor (GM-CSF or CSF2; GenBank AAA52578) is an immunomodulator produced by various cell types, including T cells, B cells, macrophages, mastocytes cells, endothelial cells, fibroblasts, and adipocytes. GM-CSF also modulates the function of antigen presenting cells and is involved in the enhancement of dendritic cell activation, and the enhancement of mononuclear phagocyte maturation. GM-CSF has been previously used in vaccines to stimulate a response (Yu et al. Novel GM-CSF-based vaccines: One small step in GM-CSF gene optimization, one giant leap for human vaccines. *Hum Vaccin Immunother.* 2016). In particular, GM-CSF has been shown to improve vaccine response for bacterial disease or infection including but not limited to diphtheria prevention (Grasse M et al. GM-CSF improves the immune response to the diphtheria-component in a multivalent vaccine. Vaccine. 2018), and tuberculosis prevention (Wang et al, Enhanced immunogenicity of BCG vaccine by using a viral-based GM-CSF transgene adjuvant formulation. Vaccine. 2002). Similar improvements have been found or theorised using GM-CSF in vaccine approaches for viral disease or viral infection including but not limited to coronaviruses, influenzae viruses (Liu et al Influenza virus-like particles composed of conserved influenza proteins and GPI-anchored CCL28/GM-CSF fusion proteins enhance protective immunity against homologous and heterologous viruses. *Int Immunopharmacol.* 2018), and porcine reproductive and respiratory syndrome virus (Yu et al Construction and in vitro evaluation of a recombinant live attenuated PRRSV expressing GM-CSF. Virol J. 2014).

Therefore, introduction of coding mRNA for GM-CSF using mRNA constructs or compositions as described herein can be used to enhance vaccine immunogenicity, through both antibody and cellular immune responses. Such approaches can therefore be used as vaccine adjuvants, enhancers, or immunological boosters in human and other recipients, and in both preventive and therapeutic vaccine types. Similar effects may be seen for other CSF type proteins such as macrophage colony stimulating factor (M-CSF or CSF1; GenBank BC021117) and granulocyte colony stimulating factor (G-CSF or CSF3; GenBank BC033245)

Other examples of products associated with the process of vaccine-induced immunity which can be induced using mRNA constructs or compositions as described herein include modulators of the Nuclear Factor NF-κB pathway, which has been implicated in the development of vaccine response to the tuberculosis (BCG) vaccine (Shey et al. Maturation of innate responses to mycobacteria over the first nine months of life. *J Immunol.* 2014).

mRNA constructs and compositions according to the above discussion can comprises any organ protection sequences as described herein. However, in particular embodiments, the organ protection sequences are selected to protect one or more of muscle, liver, kidney and skin (for example, using target sequences for miRNA-1, miRNA-122, miR-30a and/or miR-203a). In some embodiments, target sequences for all four of miRNA-1, miRNA-122, miR-30a and miR-203a are included in the organ protection sequences. Such a combination is thought to be effective in protecting muscle tissue (as compositions may be administered intramuscularly), as well as liver and pancreas tissue. Subcutaneous or intradermal administration is also common, and one or more of the miRNA target sequences associated with the skin (see Table 2) may also be used to protect cells of the skin.

It is also considered advantageous to avoid the use of miRNA-142 target sequences in such constructs and compositions, as this miRNA is abundant in cells of haematopoietic origin and immune cells, and therefore could lead to a reduction in expression in the cells anticipated to mediate the vaccine-mediated response.

Therapeutic Vaccine (or active immunotherapy)

In addition to the conventional preventive or prophylactic vaccinations, a newer field is that of therapeutic vaccines which aim to provoke an immune response against targets which are already present in the body, for example, against persistent infections or cancer. This has proven much more challenging, because in such cases the immune response has often been downregulated or otherwise restrained by tolerance mechanisms which act to protect the disease from the normal immune response (Melief et al Therapeutic cancer vaccines *JCI* 2015).

Therefore, in one embodiment, mRNA constructs as described herein coding for tumoral antigen are provided, for translation in tumour cells. This aims to induce an immune response against the cancer cells as discussed previously. By selective use of the organ protection sequences according to the invention as will by now be evident, expression can be reduced in cell types, tissues and/or organs other than the target tumour tissue, whether that be healthy cells in the tissue surrounding the tumour of the same or different tissue type, or other organs which may be affected by administration use or systemic dispersal.

Such administration can occur in combination with therapeutic vaccines, in order to improve the immune response generated, or can themselves be the therapeutic vaccines, as the immune system reacts to the introduced enhancers in order to mount a response against the tumour.

Combinations with Therapeutic Viruses as Vaccine to Treat Cancer (Therapeutic Cancer Vaccine as Viral Based Immunotherapies)

Cancer treatment vaccines, also called therapeutic vaccines, are a type of immunotherapy that boost the immune system to recognize and destroy cells carrying cancer-specific antigen (neoantigen), which are not found on healthy cells. For instance, colorectal neoantigen include MUC1, which is commonly found on colorectal tumour cells. Other neoantigens may be specific to the patient tumour. In this later case, the cancer treatment vaccine will be a personalised neoantigen vaccine. Cancer treatment vaccines are used in patients which are already diagnosed with cancer. The therapy can destroy cancer cells, stop tumour growth and spreading, or prevent the cancer from coming back after other treatments have ended. Cancer vaccines may contain the antigen against which an immune response is desired, as well as adjuvants, which strengthen the immune response.

A typical cancer vaccination strategy may involve selecting a suitable vector to deliver the tumor-associated neoantigen to the main antigen presentation cells of the immune system, e.g., dendritic cells, which are able to generate a long lasting anti-tumoral immune response. In certain embodiments, an adenovirus (Ad) vector, may be used as a vehicle for the delivery of neoantigen genes due to its high efficiency and its low risk for insertional mutagenesis. Adenovirus vectors, such as the ChAdOx1 or ChAdOx2 vectors, are a promising genetic vaccine platform as they rapidly evoke strong humoral and cellular immune responses against the transgene product and the Ad capsid proteins. This has been demonstrated by the generation of anti-tumor T-cell responses, both in vitro and in vivo through dendritic cells infected by tumoral neoantigen-encoding Ad vectors. Therefore, in one embodiment, mRNA constructs as described herein coding for one or more immunomodulators can be used to attract and activate the cellular response generated by the therapeutic cancer vaccine. Suitable immunomodulators as described herein may include IL-12, as well as derivatives (e.g., single chain forms), and homologues thereof.

Similar to its potential role in preventive/prophylactic vaccines as discussed previously, GM-CSF has also been identified as a potential adjuvant for therapeutic vaccines (Yan et al Recent progress in GM-CSF-based cancer immunotherapy. *Immunotherapy*. 2017; Zhao et al Revisiting GM-CSF as an adjuvant for therapeutic vaccines. *Cell Mol Immunol*. 2018). Similarly, CD40 ligand (CD40L), delivered as part of a virus-based vaccine to enhance antigen-specific immunity against cancer, has been shown to improve immune response and the induction of natural killer (NK) cell activation and expansion (Medina-Echeverz et al Synergistic cancer immunotherapy combines MVA-CD40L induced innate and adaptive immunity with tumor targeting antibodies. Nat Commun. 2019). mRNA constructs and compositions as described herein can therefore be used to induce the expression of GM-CSF or CD40L, to enhance anti-tumoral immune response before, during or after cancer treatment vaccines.

It can also be desired to induce an immune response against patient-specific antigen, including 'neoantigen', novel antigen produced by cancer cells as the result of mutations (Lichty et al Going viral with cancer immunotherapy. Nat Rev Cancer. 2014). In another embodiment, therefore, mRNA constructs and/or compositions as described herein can be designed comprising mRNA coding for the neoantigen of a patient. These can be in conjunction with any other mRNA coding for immunomodulators, immune enhancers, and other effector compounds, as discussed above, either in the same or different mRNA constructs. Such approaches aim to induce tumor cells to produce antigenic protein of enhanced effect, allowing the immune system to better recognise those tumor cells. This cellular response against the tumor cells can also be enhanced by further inducing the expression of immunomodulators by the cancer cells.

Hence, according to specific embodiments of the present invention there is provided an mRNA as described herein that encodes a therapeutic enhancement factor, such as an immunostimulatory or immune-modulatory protein or polypeptide, for use in combination with a cancer immunotherapeutic such as a cancer vaccine. The cancer vaccine may comprise a therapeutic virus (e.g., see Table 5), such as a modified human or primate adenovirus, and the immunostimulatory or immune-modulatory protein or polypeptide may comprise biologically active IL-12 and/or GM-CSF.

In another embodiment, mRNA constructs and/or compositions as described herein coding for a modulator and/or inhibitor of the NF-kB pathway are provided, for expression in or by tumoral cells, as discussed throughout.

The compositions and methods of the invention are exemplified by, but in no way limited to, the following Examples.

EXAMPLES mRNA Constructs

All mRNA constructs are synthetized by Trilink Biotechnologies (San Diego, Calif.) from a generated DNA sequence. These mRNAs resemble fully processed, capped and polyadenylated mRNAs and are ready for translation by the ribosome.

Formulation

All mRNA constructs are formulated into a multi-component nanoparticle of ionizable lipid-like material C12-200, phospholipid DOPE, cholesterol and lipid-anchored polyethylene glycol C14-PEG2000-DMPE mixture. This particular composition and specific weight ratio (10:1) of C12-200:mRNA and molar [%] composition of lipid-like material, phospholipid, cholesterol and PEG was optimized for high transfection efficiency in vivo (Kauffman K. J., Nano Letter. 2015, 15, 7300-7306) and is referred to as $DMP^{CTx}$-mRNA. To make the formulations, lipid components were dissolved in ethanol and mixed at 1:3 ratio with mRNA diluted in 10 mM citrate buffer (pH 3) using a T junction mixing apparatus. Formulations were dialyzed in 20 kDa membrane dialysis cassettes against phosphate buffered saline (PBS, pH 7.4) for 4 hours at room temperature. When necessary, formulations were then concentrated using Amicon Ultra centrifugal filtration units (100 kDa cutoff). Subsequently, formulations were transferred to a new tube ready for characterization. Efficacy of mRNA encapsulation and concentration is measured using the Ribogreen RNA assay (Invitrogen) according to the manufacturer's protocol. Polydispersity Index (PDI) and size ($Z_{ave}$) of the lipid nanoparticles are measured using dynamic light scattering (Zetasizer Nano-ZS, Malvern).

Figure 2:
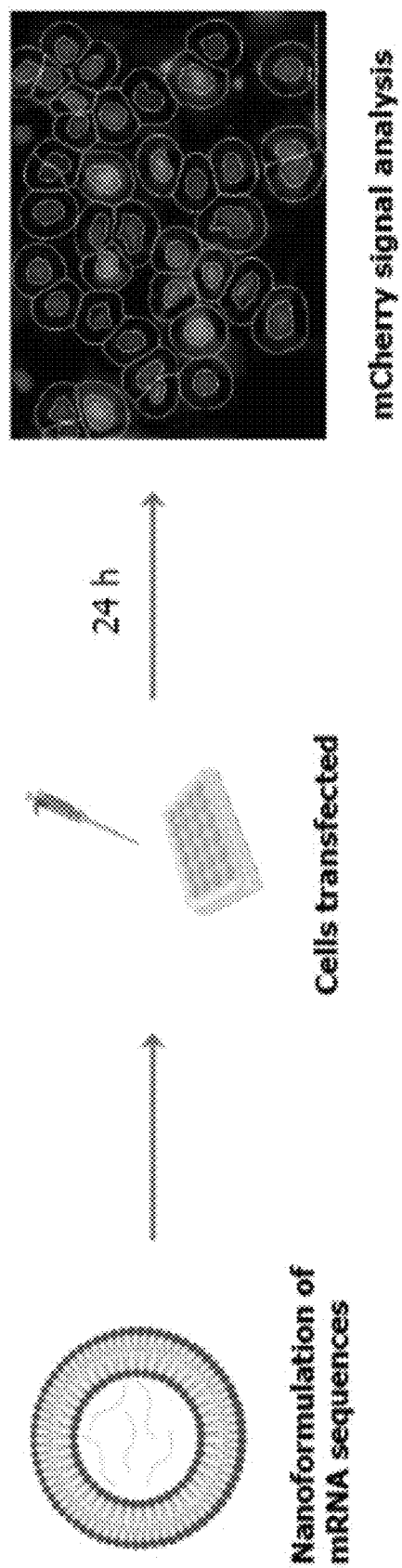
FIG. 2 shows a schematic of the protocol carried out to determine the expression of the reporter gene mCherry after administration of compositions as described herein to various cell types, mCherry signal analysis is carried out by fluorescence microscopy (Texas Red and DAPI filters), with cell nuclei stained with Hoechst 33342.

Formulations are used to transfect cells in a multi-well plate assay as depicted in FIG. 2. Formulations are suitably diluted to around 1.5 pmol/well of $DMP^{CTx}$-mRNA. The readout of the assay is to detect expression of the mRNA via mCherry fluorescence, with Hoechst 33342 staining (NucBlue Liver ReadyProbes Reagent, Life Technologies) to stain cell nuclei and determine cell density. mCherry fluorescence was quantified 24 h after transfection using fluorescence microscopy (Cytation Systems from BIOTEK or EVOS FL Auto from Thermofisher Scientific).

These formulations are also used to transfect cells in in vivo animal studies.

Cell Cultures and Transfection

All cells were grown at 37° C. in the presence of 5% $CO_2$. In vitro single transfections of cultured cells (Hep3B, AML12, 786-0, hREC, HCT-116) were performed as follows: one day prior to transfection, cells were seeded in a 96-well tissue culture treated microwell plate in recommended complete media and cell density listed in Table 5. The next day, cells were transfected with 1.5 pmol of $DMP^{CTx}$-mRNAs in 200 uL of reduced serum medium (Opti-MEM medium, Gibco) by direct addition of mRNA-$DMP^{CTx}$ to the medium in the well, with gentle mixture of the cultured cells as needed. After 4 hours of incubation, the Opti-MEM medium was removed and substituted by complete media.

TABLE 5

Medium and Cell Density Used for in vitro Transfection of DMP$^{CTx}$-mRNA

| Cell Type | | Complete Medium | Cell density for seeding microwells |
|---|---|---|---|
| Hep3B | Human hepatocellular carcinoma (ATCC HB-8064) | Eagle's Minimum Essential Medium, 10% Fetal Bovine Serum | 60,000 cells per mL |
| AML12 | Normal murine liver cells (ATCC CRL-2254) | DMEM: F12, 10 ug/mL insulin, 5.5 ug/mL transferrin, 5 ng/selenium, 40 ng/mL dexamethasone, 10% Fetal Bovine Serum | 60,000 cells per mL |
| 786-0 | Human renal adenocarcinoma (ATCC 1932) | RPMI-1640, 10% Fetal Bovine Serum | 60,000 cells per mL |
| HREC | Normal human renal mixed cells (ATCC PCS-400-012) | Renal Epithelial Cell Basal Medium (ATCC PCS-400-030), Renal Epithelial Cell Growth kit (ATCC PCS-400-040) | 60,000 cells per mL |
| HCT-116 | Human colorectal carcinoma | McCoy's 5A medium, 10% Fetal Bovine Serum | 400,000 cells per mL |

For transfection of human normal hepatocytes (Sigma Product Reference No MTOXH1000), cells were plated in 24-well Collagen coated plates at a cell density of 250,000 cells per mL using Sigma recommended thawing, fully supplemented plating and culture media (references MED-HHTM, MED-HHPM, MED-HHPMSP, MED-HHCM, MED-HHCMSP). Transfection of mRNA-DMP$^{CTx}$ was performed in culture medium containing 5% FBS. After 4 hours of incubation, the mRNA mixture was removed, and fully supplemented medium was added back to the wells.

For transfection of normal epithelial adult colonic cells (Cell Applications, Inc., reference 732Cn-05a), cells were thawed, plated and cultured using GI Epithelial Cell Thawing Solution and GI Epithelial Cell Defined Culture Medium (Cell Applications Inc., references 716DC-50 and 716T-20). 96-well microplate wells were pretreated with GI Epithelial Cell Coating Solution (Cell Applications, Inc., reference 025-05) and 60,000 cells per well were seeded. The next day, cells were transfected with 1.5 pmol of DMP$^{CTx}$-mRNAs in 200 uL of reduced serum medium (Opti-MEM medium, Gibco) by direct addition of mRNA-DMP$^{CTx}$ to the medium in the well, with gentle mixture of the cultured cells as needed. After 4 hours of incubation, the Opti-MEM medium was removed and substituted by the culture medium.

For transfection of normal human lung/bronchial cells (BAES-2B cells, ATCC CRL-9609), cells were grown in BEGM medium (Lonza) supplemented with BEGM Bronchial Epithelial SingleQuots kit (Lonza). Cells were seeded in Collagen I coated microwell plates at a density of 75,000 cells per mL. The next day, cells were transfected with 1.5 pmol of DMP$^{CTx}$-mRNAs in 200 uL of reduced serum medium (Opti-MEM medium, Gibco) by direct addition of DMP$^{CTx}$-mRNA to the medium in the well, with gentle mixture of the cultured cells as needed. After 4 hours of incubation, the Opti-MEM medium was removed and substituted by the culture medium.

Fluorescence Microscopy 24 hours following transfection, cells nuclei were stained using the Hoechst 33342 dye (NucBlue™ Live Ready-Probes™ Reagent from Invitrogen). Nuclei staining and mCherry fluorescence were detected in live cells using a fluorescence microscope (Cytation instrument from Biotek or EVOS® FL Imaging Systems from Thermofisher Scientific). Images were acquired with filter cubes Texas Red and DAPI and a 20× objective.

Example 1

Unoptimized Vs Optimized MIRNA Target Sequence (Unmatched Vs Matched)

To investigate the potential of the present invention to successfully transfect target cells with construct mRNA and subsequently drive better protein differential expression than the unmodified miRNA target sequence, the DMP$^{CTx}$ mRNA platform, modified with miRNA binding sites, is first evaluated in vitro using human cancer cell lines and normal primary cell for each organ. Purified mCherry mRNA is used for tracking transfection and translation efficiency in cultured cells.

For instance, miRNA-122 is an abundant, liver-specific miRNA, the expression of which is significantly decreased in human primary hepatocarcinoma (HCC) and HCC derived cell lines such as Hep3B. The objective of this example study is to demonstrate that modification of the 3'-untranslated region (UTR) of an mRNA sequence by the insertion of an optimized miRNA-122 targeted sequences (for example, variant 2) may result in a higher translational repression of exogenous mRNA in normal hepatocytes, but not in tested HCC cell lines. For that purpose, an mCherry mRNA construct was modified to include at least one unoptimized miRNA-122 target sequence in the 3'-UTR (variant 1) or at least one optimized perfect matching target sequence (variant 2). The mRNA construct is transfected into murine AML12 normal hepatocytes, known to express high level of miRNA-122. An mCherry mRNA construct with no miRNA target sequence was used as a positive control. mCherry fluorescence was detected 24 h after single transfection of the mCherry mRNA constructs using fluorescence microscopy (EVOS FL Auto from Thermofisher Scientific). Alternative quantification methodology can be used to verify the expression of the delivered construct, including Western blot or proteome analysis techniques such as mass spectrometry.

```
Variant 1 [SEQ ID NO: 4]:
5'-AACGCCAUUAUCACACUAAAUA-3'
(unmatched miR-122 target sequence)

Variant 2 [SEQ ID NO: 44]:
5'-CAAACACCAUUGUCACACUCCA-3'
(perfect matched miR-122 target sequence)
```

Results

Figures 9A, 9B, 9C, 9D:
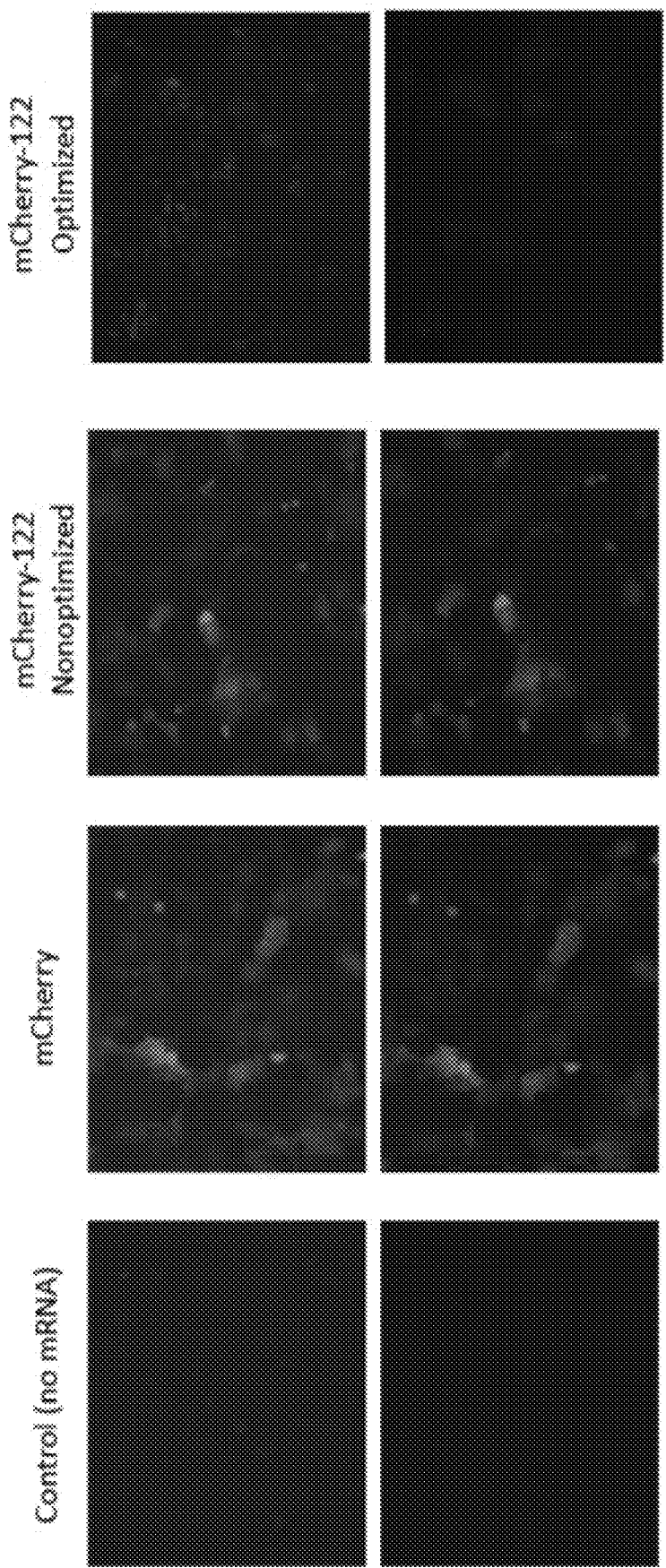
FIGS. 9A-9D show comparison of mCherry signal in AML12 murine liver hepatocytes transfected with compositions as described herein that comprise an unperfect matched duplex (2*) MOP sequence that binds to miRNA122. For each of (FIG. 9A), (FIG. 9B), (FIG. 9C) and (FIG. 9D), the top panel is a superimposition of images acquired with the Texas Red and DAPI filter cubes, showing cell nuclei staining and mCherry fluorescence. The bottom panel represents an image acquired with the Texas Red filter cube and shows the mCherry fluorescence only.

As shown in FIG. 9B the expression of mCherry mRNA without MOP is strong in AML12 cells. When a single imperfectly matched miR-122 target sequence (Variant 1) is included in the 3' UTR, expression of mCherry remains evident (see FIG. 9C. The effect of perfect matching using Variant 2 is clear with much reduced mCherry expression apparent in FIG. 9D, right hand panel.

Example 2

Comparing the Effect of Repeat Numbers of miRNA Target Sequences

To investigate the potential of the present invention to drive better differential expression by increasing the number of target sequences in the mRNA construct, mCherry mRNA was modified to include one, two or four optimized miRNA-122 miRNA target sequences in the 3'-UTR and translation efficiency was evaluated and compared in vitro in human Hep3B cancer cell lines and corresponding normal AML12 primary cells. An mCherry mRNA construct with no miRNA target sequence was used as a positive control. miR-122 target sequences are linked using specific nucleotide (like uuuaaa) as shown in FIG. 1. mCherry fluorescence was detected 24 h after single transfection of the mCherry mRNA constructs by fluorescence microscopy (EVOS FL Auto from Thermofisher Scientific). Alternative quantification methodology can be used to verify the expression of the delivered construct, including Western blot or proteome analysis techniques such as mass spectrometry also.

Results

Figure 8A:
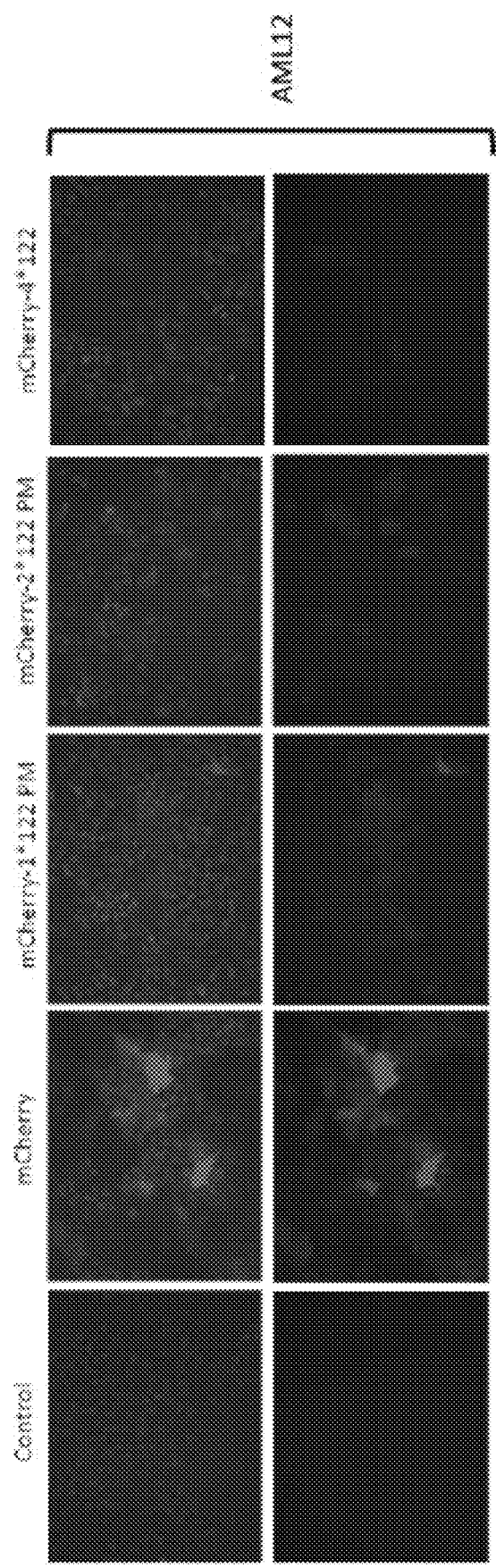
FIGS. 8A-8B show comparison of mCherry signal in liver cells transfected with compositions as described herein that comprise a perfect matched multiplexed MOP sequence that binds to miRNA-122 replicated once (1*), twice (2*) or four times (4*), and shows that there is some dose dependence in suppression of mCherry expression in AML12 normal hepatocytes (FIG. 8A), but far less so in Hep3B cancer cells (FIG. 8B). For each of (FIG. 8A) and (FIG. 8B), the top panel is a superimposition of images acquired with the Texas Red and DAPI filter cubes, showing cell nuclei staining and mCherry fluorescence. The bottom panel represents an image acquired with the Texas Red filter cube and shows the mCherry fluorescence only. A control of no injected mRNA is included as well as mRNA for mCherry but without a MOP sequence.
Figure 8B:
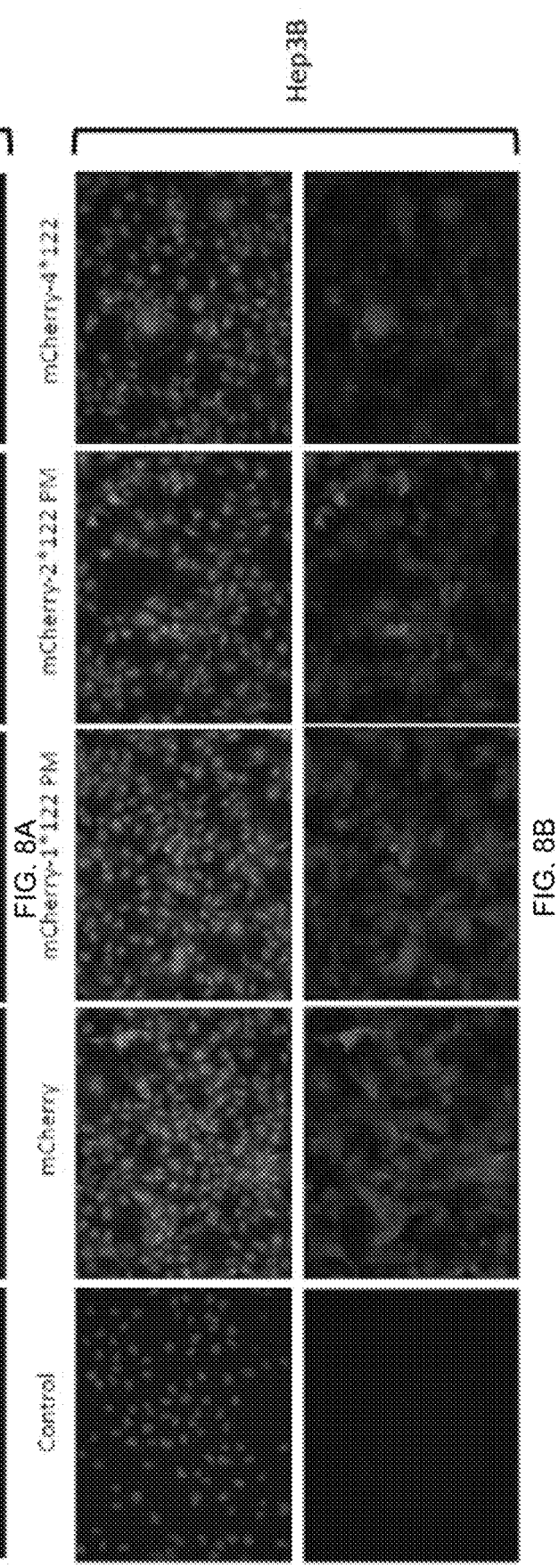

The results of multiplexing a binding site sequence are shown in FIGS. 8A-8B. There is some dose dependence in suppression of mCherry expression in AML12 normal hepatocytes (a), with two and four repetitions of the binding site sequence showing high levels of suppression of mCherry. However, the effect is less evident for Hep3B cancer cells (b), where the levels of mCherry expression remain largely consistent for one or two repetitions of the miRNA binding site, with only a slight reduction in expression for the four-fold multiplexed sequence.

Example 3

Assessing the Effect of a Multi-Organ Protection (MOP) Sequence on mCherry Expression Compared to mCherry without Mop To investigate the potential of the MOP sequences to reduce or eliminate translation of an ORF in non-diseased cells comprised within one or more organs selected from the group consisting of: liver; pancreas; brain and CNS; kidney; spleen; gut, including oesophagus, stomach, intestine, colon, and rectum; lung; skin and breast, mCherry mRNA is modified to include at least three non-optimized miRNA target sequences in the 3'-UTR, wherein the first, second and third miRNA target sequences are all different from each other. In this example target sequences that are optimized to bind to miR-122, Let7b and miR-192 are provided enabling multi-organ protection for non-diseased cells in liver, lung/breast and kidney respectively. Translation efficiency is evaluated and compared in vitro in human cancer cell lines and corresponding normal primary cells for each protected organ. An mCherry mRNA construct with no miRNA target sequence is used as a positive control. mCherry fluorescence is quantified 24 h after single transfection of the mCherry mRNA constructs using a fluorescence imaging system (Cytation instrument from BIOTEK). Target sequences are linked using specific nucleotide (like uuuaaa).

Example 4

Proof of Concept of Multi-Organ Protection Methods In Vitro

To investigate the potential of the present invention to demonstrate differential expression of a particular ORF in multiple different recipient cell types, mCherry mRNA was modified as in Example 3 to include three or five miRNA target sequences in the 3'UTR. In a first mRNA sequence target sequences for miR-122, Let7b and miR-192 are provided (mCherry-3MOP), and in a second mRNA sequence target sequences for miR-122, miR-124a, Let7b, miR-375, and miR-192 are provided (mCherry-5MOP). A control mCherry mRNA sequence was also used without miRNA target sequences.

The prepared mRNA sequences were nanoformulated as described above. The prepared nanoparticles were transfected into cell lines (FIG. 2) corresponding to human normal hepatocytes (Sigma Product Reference No MTOXH1000); murine normal hepatocytes (AML12 from ATCC), and human hepatocarcinoma cells (Hep3B from ATCC). In addition, a cell line corresponding to normal human kidney cells (hREC from ATCC) was transfected with mCherry-3MOP mRNA, and control mCherry RNA. Cells were seeded in a 24-well plate. 0.5 ug of mRNA was transfected per well and imaging was performed 24 h post-transfection with a Cytation 5 instrument (Biotek).

Figure 3:
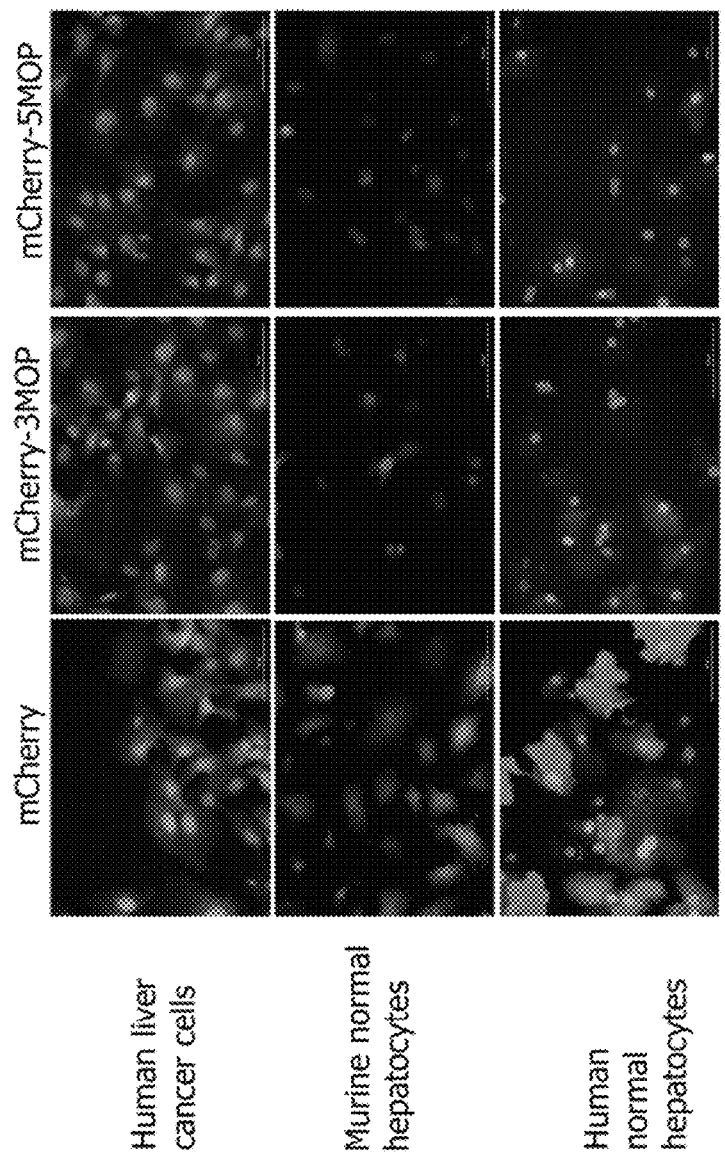
FIG. 3 shows mCherry signal in three liver cell types following the above protocol, and demonstrates significant reduction of cell signal in both normal murine and human hepatocytes when transfected with mCherry-3MOP or mCherry-5MOP mRNA, compared to the signal found in human liver cancer cells (Hep3B) or in normal murine hepatocyte (AML12) cells after transfection with control mCherry mRNA. The images are superimposition of images acquired with Texas Red and DAPI filters, showing mCherry fluorescence signal and cell nuclei staining.
Figure 4:
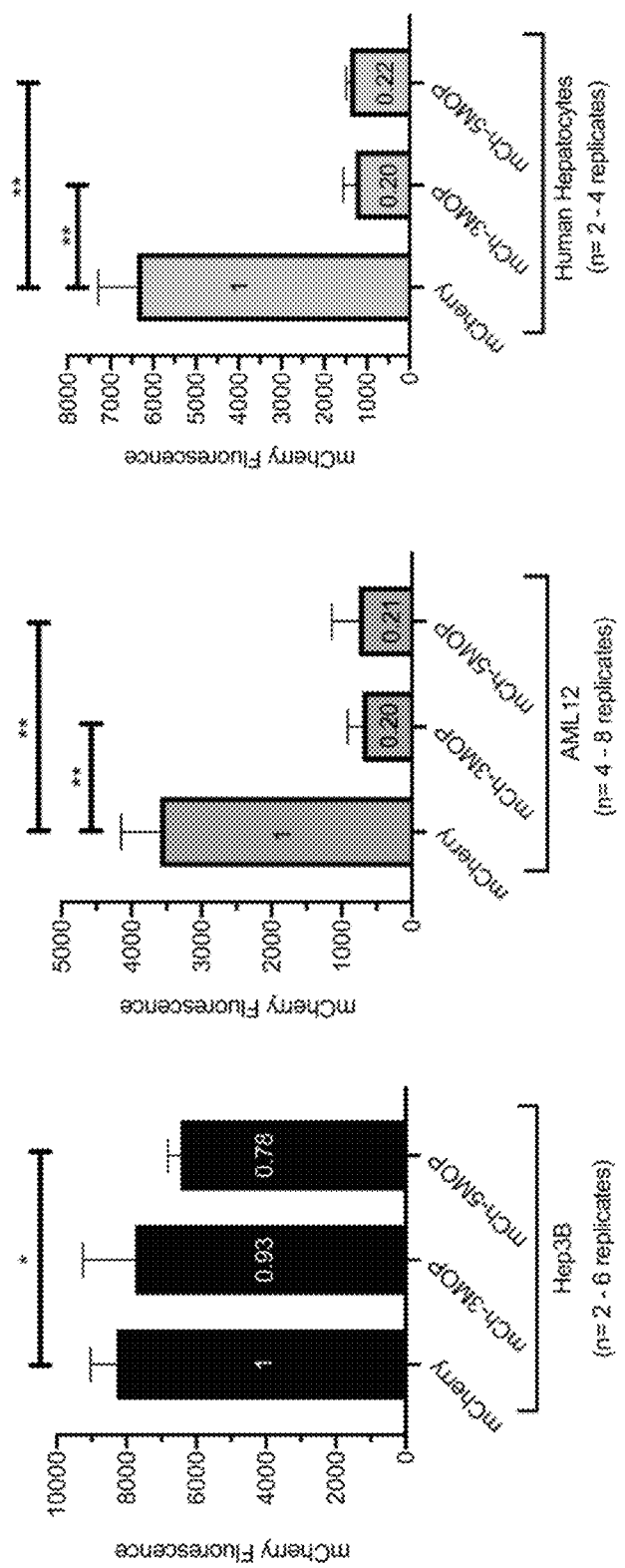
FIG. 4 shows quantification of mCherry fluorescence in the transfected cells using a Cytation instrument (Biotek).

FIG. 3 shows mCherry signal in the three liver cell types, and demonstrates significant reduction of cell signal in both normal murine and human hepatocytes when transfected with mCherry-3MOP or mCherry-5MOP mRNA, compared to the signal found in the human liver cancer cells (Hep3B) or in the normal cells after transfection with control mCherry mRNA. This indicates a reduction in mCherry translation in normal cells as a result of the inclusion of the miRNA target sequences. FIG. 4 shows quantification of mCherry fluorescence in the transfected cells using the Gen5 Imaging Software from Biotek. Background signal has been subtracted. Values represent the mean and standard deviation of fluorescence signal per cell. Statistically significant differences for assessed mRNA compared to control are shown as * P<0.05, ** P<0.005. The results demonstrate approximately 80% reduction in protein expression in normal liver cells (human and murine) when 3MOP or 5MOP miRNA target sequences are used, while less reduction is seen in tumoral cells.

FIG. 5A shows mCherry signal in transfected normal human kidney cells (hREC ATCC-PCS-400-012). A reduction in signal is visible in the mCherry-3MOP treated cells, indicating a reduction in mCherry translation. This is quantified in FIG. 5B using the Gen5 Imaging Software from Biotek, which likewise shows around a 60% reduction in mCherry signal in normal kidney cells after transfection with mCherry-3MOP. In FIG. 5B, background signal has been subtracted, and values represent the mean and standard deviation of fluorescence signal per cell. Statistically significant differences for assessed mRNA compared to control are shown as * P<0.05.

In FIGS. 6A-6F, the results of an experiment in liver cells using an alternative configuration of a 3MOP sequence are shown. In this instance the 3MOP sequence comprises miRNA binding sites that have been perfectly matched to miRNA122, miRNA192 and miRNA30a. The expression in Hep3B cancer cells is clearly seen in FIG. 6C when compared to murine AML12 hepatocytes in FIG. 6F, where no discernible expression is visible.

FIGS. 7A-7F show the results of another alternative configuration of the 3MOP sequence. In this instance the 3MOP sequence comprises miRNA binding sites that have been perfectly matched to Let7b, miRNA126 and miRNA30a. Again, the mCherry expression in Hep3B cancer cells is clearly seen in FIG. 7C when compared to murine AML12 hepatocytes in FIG. 7F, where no discernible expression is visible.

FIGS. 10A-10F demonstrate the effects of tissue and organ specific protection in the kidney for the same 3MOP sequence as used in the experiments for FIGS. 7A-7F (miRNAlet7b-miRNA126-miRNA30a). The expression of mCherry is almost completely suppressed in hREC human kidney cells (FIG. 10F) but not in 786-0 renal adenocarcinoma cells (FIG. 10C). In FIGS. 11A-11F, the alternative 3MOP sequence is tested (miRNA122-miRNA192-miRNA30a). Both the MOP sequences tested for FIGS. 10A-10F and 11A-11F comprise perfect match binding sequence for miRNA30a, which is protective of kidney; however, the latter 3MOP further comprises a perfect match miRNA-192 binding site which provides a putative double layer of kidney protection (see Table 2, above). In FIGS. 11A-11F the expression of mCherry is not visible in hREC human kidney cells (FIG. 11F) but is clearly evident in 786-0 renal adenocarcinoma cells (FIG. 11C).

FIGS. 13A-13F demonstrate the effects of tissue and organ specific protection in the colon for the same 3MOP sequence as used in the experiments for FIGS. 11A-11F (miRNA122-miRNA192-miRNA30a). The expression of mCherry is almost completely suppressed in human colon epithelial cells (FIG. 13C) but not in HCT-116 cells (FIG. 13F). In FIGS. 14A-14F, the alternative 3MOP sequence is tested (miRNAlet7b-miRNA126-miRNA30a). The MOP sequence tested for FIGS. 14A-14F comprise a perfect match binding sequence for Let7b, which is broadly protective of colon tissue. In FIGS. 14A-14F, the expression of mCherry is highly reduced in colon epithelial cells (FIG. 14c) and also in HCT-116 cells (FIG. 14F).

FIGS. 15A-15C demonstrate the effects of tissue and organ specific protection in the lung using the MOP sequence comprising binding sites for miRNAlet7b, miRNA126, and miRNA30a. Similar to the other assays described above, a bronchial epithelial cell line was selected that represents the closest approximation of healthy non-cancerous human lung tissue: the BEAS-2B cell line. Whilst BEAS-2B cells are immortalized via infection with replication-defective SV40/adenovirus 12 hybrid, this is to enable improved handling and cloning. The cells are used in assays to study differentiation of squamous cells as a model of normal functioning lung epithelium. In FIG. 15C, presence of the MOP sequence results in very high levels of suppression of mCherry expression compared to the absence of MOP.

The results shown in FIGS. 7F, 10F, 14C and 15C show that inclusion of the miRNAlet7b-miRNA126-miRNA30a MOP sequences provides effective protection from associated ORF expression in healthy liver, kidney, colon and lung. The results for FIGS. 6F, 11F, and 13C show that the alternative MOP comprising miRNA122-miRNA192-miRNA30a binding sequences provides effective protection for healthy liver, kidney and colon tissue.

This example demonstrates that organ protection sequences comprising multiple different miRNA target sequences can also act to drive differential expression in cells derived from multiple different organs, and can differentiate between normal and tumoral cells in multiple tissues.

Example 5

ORF Selection of the Viral Entry Receptor, Nectin, Together with OPS Protection

The present invention aims to increase the expression of a viral entry receptor at the surface of cancer cells in order to improve the infectivity of the cancer cells by an oncolytic virus—e.g., oncolytic HSV (oHSV). For instance, an mRNA encoding HSV viral entry receptor nectin-1 is transfected into a human or murine cancer cell line at different concentration. Nectin-1 expression is measured by western blot analysis in cell lysates. Then, a mRNA encoding Nectin-1 is modified to include at least three similar or different miRNA target sequences (such as disclosed in Example 4) and differential mRNA expression is evaluated in cancer cell lines and corresponding normal primary cells for at least one organ comprised from the group consisting of: liver; pancreas; brain and CNS; kidney; spleen; gut, including oesophagus, stomach, intestine, colon, and rectum; lung; skin and breast. Reduced expression of Nectin-1 protein at the surface of non-diseased cells, as compared to that in cancer cells, is assessed by Western blot analysis. Alternative quantification methodology can be used to verify the expression of the delivered construct.

Nectin 1 mRNAs Constructs

For the following embodiment, an isotype 1 of the Nectin 1 protein coding sequence is used. This mRNA is followed by a 3' UTR that comprises the perfect match MOP sequence: miR122-miR192-miR30a (122-192-30a), which allows liver, colon and kidney protection respectively. Alternative MOP sequences may also be utilized, such as miRLet7b-miR126-miR30a (let-7b-126-30a), or different combinations comprised from these or other miRNA binding sequences. The construct is synthetized by Trilink Biotechnologies (San Diego, Calif.) from a generated DNA sequence. These mRNAs resemble fully processed, capped and polyadenylated mRNAs and are ready for translation by the ribosome. As control, the same construct is synthetized without the MOP sequence (e.g., mRNA expressing Nectin 1 only without any MOP).

In vitro Nectin 1 Transfections

To study whether Nectin 1 increases infectivity oncolytic HSV (oHSV), hepatocytes are used because of their known low level of Nectin 1 expression. For in vitro transfection of the Nectin 1 constructs, human liver hepatocarcinoma Hep3B cells and normal primary human hepatocytes transfected with the $DMP^{CTx}$-mRNA Nectin 1 comprising the following MOP sequence in the 3'UTR: miRNA-122, miRNA-192, and miRNA-30a binding sequence (Nectin-MOP). The transfection of the Nectin-MOP construct leads to high expression level of Nectin 1 protein in Hep3B cancer cells, while keeping its level low in healthy hepatocytes due to the miRNA122 binding sequence protection.

Transfections of the mRNAs are performed by using the $DMP^{CTx}$ technology as follows: one day prior to transfection, cells are seeded separately into a microwell plate at a density of 60,000 cells per mL. The next day, cells are transfected either with a vehicle control of PBS alone, with Nectin 1-122-192-30a (Nectin-MOP), or with Nectin 1 without MOP sequence (Nectin). The transfection is carried out by direct addition of mRNA-$DMP^{CTx}$ to the cultured medium in the well, with gentle mixture of the cultured cells as needed.

Nectin 1 Detection by Immunoblot and Immunofluorescence

To control the Nectin 1 translation, immunoblot is performed as follows. Culture media is removed, cells are washed with cold PBS and cell pellets are lyzed in RIPA (radioimmunoprecipitation assay) buffer (Boston Bioproducts) with a cocktail of protease inhibitors (Sigma). Cells fractions are separated to isolated membrane protein from cytoplasmic soluble proteins. Proteins are then separated by polyacrylamide gel electrophoresis and transferred onto PVDF (polyvinylidene difluoride) membranes by electroblotting. After blocking with 5% nonfat dry milk in TBS-Tween 20 (Boston Bioproducts), membranes are incubated with a primary anti-Nectin 1 or b-actin (control) antibody, followed by incubation with a secondary antibody (e.g., HRP (horseradish peroxidase)-conjugated antibody). Protein detection is then performed using Clarity™ Western ECL Substrate (Bio Rad) and LI-CORE® system (LI-COR), respectively.

To control that Nectin 1 is well located at the surface of the cells, immunofluorescence is performed as follows. Transfected cells are grown on coverslips (pre-incubated with 0.2% gelatin for 30 min), rinsed in PBS, and pre-extracted in 0.5% CSK-Triton supplemented with 10 mM ribonucleosidevanadyl complex (VRC) (New England Biolabs) on ice for 2 min. Cells are then washed once in CSK supplemented with 10 mM VRC, and incubated on ice for 2 min, followed by fixation by 4% paraformaldehyde in PBS at room temperature for 10 min. Cells are then washed twice with PBS and blocked in 1% bovine serum albumin in PBS containing RNase inhibitor (Roche) at room temperature for 20 min. Incubation is carried out at room temperature for 1 hr with primary antibody raised against Nectin 1 (ab229464) at 1/500 in PBS containing 1% bovine serum albumin and RNase inhibitor (Roche). Cells is washed three times in PBS containing 0.02% Tween-20 (PBS-T). After incubating with fluorescent-conjugated goat anti-rabbit secondary antibody at room temperature for 30 min, cells are washed three times in PBS-T. The slides are then mounted with a drop of Vectashield with 4',6-diamidino-2-phenylindole (DAPI). Imaging is performed with a fluorescence microscope (EVOS FL Auto from Thermofisher or Cytation instrument form Biotek).

Results

Transfection of $DMP^{CTx}$-mRNA Nectin-MOP construct transfection will lead to expression in the Hep3B cancer cells whereas the healthy hepatocytes will be protected from the mRNA translation due to the MOP sequence. Transfection of the mRNA construct without the MOP sequence will show high expression of the Nectin 1 protein in both cancer and normal liver cells due to the absence of the sequence protection. Immunoblot results will show a band around ~57kDA, corresponding to the Nectin 1 protein, in the protein lysates from the Hep3B cells transfected by both constructs. Whereas the band will be present only in the healthy hepatocytes that are transfected by mRNA without the MOP sequence, The immunofluorescence experiments will show that only the cells that were positive in immunoblot display the Nectin 1 properly located at the membrane.

Protein samples will be prepared at interval times after the mRNA transfection to determine when a high level of Nectin 1 is expressed in the cell membrane. This information will serve as the point of reference for the infection with the oHSV.

Example 6

Assessment of Whether Nectin-1 Increases Infectivity (Co Infection with HSV, In Vitro)

The present invention aims to increase oncolytic virus infectivity of cancer cells. An mRNA encoding a viral entry receptor is transfected in cancer cells in combination with an oncolytic virus. Increased cytopathogenic effect, increased viral load, increased cancer cell death are evaluated. For instance, an mRNA encoding HSV viral entry receptor Nectin-1 is modified to include at least three similar or different miRNA target sequences and differential mRNA expression is evaluated in cancer cell lines and corresponding normal cells for at least one organ comprised from the group consisting of: liver; pancreas; brain and CNS; kidney; spleen; gut, including oesophagus, stomach, intestine, colon, and rectum; lung; skin and breast. Cancer cells and corresponding normal cell will be transfected with the modified nectin-1 mRNA construct. An oncolytic HSV (oHSV) is used subsequently to infect the cells and increased cell death will be evaluated for both cancer and normal cells.

Efficiency of the oHSV Infection

The oncolytic virus MG18L strain of the oHSV (Us3Δ, UL39 (ICP6)$^-$, LacZ$^+$) is used in these experiments to infect healthy hepatocytes and Hep3B cells. Prior to viral infection, the cells are transfected, or not, with $DMP^{CTx}$ Nectin-MOP or Nectin 1 without the MOP sequence. Cells are then infected with serial dilutions of oHSV. As mentioned in Example 5, alternative MOP sequences may also be utilized, such as miRLet7b-miR126-miR30a (let-7b-126-30a), or different combinations comprised from these or other miRNA binding sequences.

Nectin 1 is confined at the adherent junctions in epithelial cells and may not be fully accessible to the virus (Yoon and Spear, 2002). Calcium depletion disrupts cell junctions and induces redistribution of the Nectin 1 over the entire cell surface, which enhances the fraction of cells that could be infected by HSV (Yoon and Spear, 2002). In this embodiment, calcium depletion may be performed by including, but not limited to, a treatment with BAPTA-Na4 molecule that is a calcium chelator. A combinatorial effect of BAPTA-Na4 treatment and Nectin-MOP on oHSV-infected Hep3B cells is performed to assess whether the infectivity is increased upon calcium chelation. BAPTA-Na4 is added to the cell media before the oHSV infection.

At different timepoints post-infection, the viability of transfected cell lines is measured by MTT assay according to vendor instructions (Cell Proliferation kit I, Sigma). Absorbance is measured at 550-600 nm with a 96-well plate to determine dose-response curves and 50% effective dose values (ED50).

In parallel, at various intervals post-infection, the replication of the oHSV is also assessed by using real-time PCR assays with primers complementary to the oHSV genome, including, but not limited to, the US6 gene that encodes the Glycoprotein D (Forward primer: CCCCGCTGGAACTAC-TATGA [SEQ ID NO: 58]; and Reverse primer: TCGGTGCTCCAGGATAAACT [SEQ ID NO: 59]). Genomic and viral DNAs are isolated from cells by using the QIAamp DNA Mini Kit (Qiagen) according to the manufacturer's protocol. Real-time PCR is performed using an iQ SYBR Green Supermix (Bio-Rad) on QuantStudio 6 Flex Rel-Time PCR Instrument (Applied Biosystems). Relative oHSV detection level is calculated based on ΔΔCt method. Internal control, like the human Gapdh gene (Forward primer: CCCACACACATGCACTTACC [SEQ ID NO: 60]; Reverse primer: CCCACCCCTTCTCTAAGTCC [SEQ ID NO: 61]), is used for signal normalization.

Because the MG18L strain contains the *Escherichia coli* LacZ gene that encodes b-galactosidase, a lacZ assay can serve as a marker of infection and viral particles titer are determined by end-point dilution assay using a monolayer of Vero cells. After Hep3B cell infection experiments, viral particles are recovered in the supernatant. 10 uL of serial dilutions are incubated with Vero cells for 1-2 h at 37° C. The cells are then washed to remove the virus inoculum and incubated at 37° C. for 2-3 days until plaques develop. The cells are then fixed with a solution of 2% paraformaldehyde and 0.2% glutaraldehyde. Plaques are stained using a 0.1% solution of X-Gal (5-bromo-4-chlor-3-indolyl-β-D-galactopyranoside) and counted using an inverted microscope.
Results Hep3B cancer cells and normal hepatocytes transfected with $DMP^{CTX}$ Nectin without MOP sequence should both express high level of Nectin 1 in the cell membrane and are both expected to be highly susceptible to oHSV MG18L, resulting in cell death. Real-time PCR and viral end-point dilution assay will show increased in viral titer post-infection, indicating increased viral replication for both cell types. When not transfected by Nectin 1 mRNA prior to viral infection, both cell types will display relative poor susceptibility to oHSV MG18L. Healthy hepatocytes transfected with $DMP^{CTX}$ Nectin-MOP will give similar results, as Nectin 1 protein will not be expressed in these cells due to the presence of high level of miRNA-122, ultimately inhibiting translation of the mRNA by binding to the MOP sequence. Hep3B cancer cells transfected with Nectin-MOP will exhibit a high susceptibility to MG18L infection due to the high expression of Nectin 1, which results from the lower expression of miRNA-122 in hepatocellular carcinoma.

Example 7

Assessment of Whether Nectin-1 Increases Infectivity of Co-Infection with HSV, In Vivo This experiment describes a mammalian model to determine whether susceptibility to oHSV infection can be increase in human hepatocarcinoma by expressing Nectin-1 in the tumour, while sparing healthy liver tissue.

Subcutaneous Xenograft of Hep3b Cells in SCID Mice

Female CB17/Icr-$Prkdc^{scid}$/IcrIcoCrl Fox Chase SCID mice are used for subcutaneous xenograft. Hep3B cells are resuspended in 1:1 PBS:Matrigel™ and then injected on to the right flank of each mouse. Tumor growth is monitored twice a week by observation and palpation. Sufficient and homogeneous tumor size between group is defined as the starting point to perform a treatment trial.

Intra Tumoral Injection of Nectin 1 and Detection of the Translated Nectin 1 Protein $DMP^{CTx}$ Nectin-MOP, Nectin, or saline solution is intratumoral (IT) injected in mice multiple times during a treatment period, in combination or not with BATPA-Na4. As mentioned in previous examples 5 and 6, an alternative MOP may be used. At different timepoints, the mice are sacrificed, and the tumors are collected and prepared into FFPE blocks for further analysis. Liver and other non-diseased organs such as spleen, lungs, and kidneys, are also collected and prepared into FFPE blocks in order to investigate the biodistribution of the mRNA formulations. Immunohistochemistry is then performed to assess the expression of Nectin-1 in the tissues.

Results

The IT injection of the $DMP^{CTx}$ Nectin-MOP will lead to high level of Nectin 1 expression in Hep3B tumours, while its expression will be reduced in healthy liver, while its expression in non-diseased organs is reduced (e.g., liver, kidneys, lungs, spleen). Such differential expression for the Nectin 1 should be achieved in tumoral cells and non-diseased tissues due to the presence of the miRNA binding sites in the 3' UTR of the mRNA constructs. However, the absence of these miRNA binding sites in the $DMP^{CTx}$ Nectin without MOP will lead to expression of Nectin 1 non-diseased organs, such as liver, lungs, spleen and kidneys.

Efficiency of the oHSV Infection

Before, at the same time, or after $DMP^{CTx}$ Nectin-MOP, Nectin, or saline solution treatment, randomly grouped mice are treated by intravenous (IV) injection of MG18L or virus buffer. BAPTA-Na4 or saline buffer may be injected intratumorally before, at the same time, or after oHSV infection to observe the combinatorial effect of Nectin 1 and BAPTA-Na4 to the infectivity of the virus. The size of tumors are measured by caliper every 3 or 4 days in order to observe the combined therapeutic effect on tumor growth. At different point after infection, subgroups of mice are sacrificed. Tumors and non-diseased tissues (e.g., liver, kidneys, lungs, spleen) are collected and prepared into FFPE blocks for analysis by immunohistochemistry. The virus localization is detected using antibodies against HSV glycoprotein D followed by incubation with appropriate fluorescent-conjugated secondary antibodies for detection.

Results

The Hep3B tumors pre-treated with $DMP^{CTx}$ Nectin-MOP or Nectin are expected to be more susceptible to the oHSV infection and should be significantly smaller in size and displaying higher amount of glycoprotein D compared to the tumors treated with oHSV alone. The combined BAPTA-4Na—Nectin 1 treatment should enhance the sensitivity of the tumor to the oHSV. Due to the intravenous injection of the oHSV, non-diseased tissues, such as healthy liver, kidneys, lungs, and spleen, are to be protected from oHSV infection in mice treated with $DMP^{CTx}$ Nectin-MOP. Different schedules of DMPCTx and oHSV administration will allow to determine the best conditions for increasing oHSV infection of tumour cells (e.g., pre-treatment of tumours with $DMP^{CTx}$ before oHSV administration, co-administration of $DMP^{CTx}$ and oHSV, or treatment with $DMP^{CTx}$ after oHSV injection).

Example 8 mRNA Coding for Monomorphic MHC Class I-Related Protein (MR1) Expression Delivered to Cancer Cells to Determine Increase in Cancer Cell Lysis from MR1-Restricted T Lymphocyte Cells The present invention aims to increase anti-tumoral effect linked to MR1-restricted T lymphocytes cells that recognize MR1 at the surface of cancer cells.

For instance, an mRNA encoding MR1 as the ORF is modified as described in previous examples to include a MOP having at least three similar or different miRNA target sequences, and differential mRNA expression is evaluated in cancer cell lines and corresponding normal primary cells for at least one organ comprised from the group consisting of: liver; pancreas; brain and CNS; kidney; spleen; gut, including oesophagus, stomach, intestine, colon, and rectum; lung; skin and breast. Cancer cells and corresponding normal cells are transfected with the modified MR1 mRNA construct. PBMC or T-lymphocytes are used subsequently to lyse cancer cells that express preferentially MR1 (for example, as described in Crowther et al Nature Immunology, volume 21, pages 178-185(2020)).

MR1 mRNA Constructs

For the following experiment, the isotype 1 of the human MR1 mRNA is used. This mRNA is followed by a 3' UTR that comprises the perfect match MOP sequence (MR1-MOP): miR122-miR375-miR30a (122-375-30a), which allows liver, pancreas and kidney protection respectively. Alternative MOP sequences may also be utilized or different combinations comprised from these or other miRNA binding sequences. The construct is synthetized by Trilink Biotechnologies (San Diego, Calif.) from a generated DNA sequence. These mRNAs resemble fully processed, capped and polyadenylated mRNAs and are ready for translation by the ribosome. As a negative control for liver, pancreas, and kidney non-protection, the same construct is synthetized without the MOP sequence (MR1)

In Vitro MR1 Transfections

Liver and pancreatic cancer cell lines are used in order to study whether MR1 increases anti-tumoral effect linked to MR1-restricted T lymphocytes cells that recognize MR1 at the surface of cancer cells, because MR1 seems to be not highly expressed in these organs (The Human Protein Atlas). For in vitro transfection of the MR1 constructs, human liver hepatocarcinoma Hep3B (ATCC® HB-8064™), and human pancreatic adenocarcinoma BxPC-3 cells are obtained, for example from ATCC (CRL-1687™).

Normal human hepatocytes, and normal human pancreatic duct epithelial H6c7 cells (Kerafast ECA001-FP) are used as negative controls to observe the liver and pancreatic protection of the MR1-MOP construct. The exogenous MR1 will be not translated in the healthy hepatocytes and pancreatic cells due to the presence of the miR122 and miR375 binding sequences in the 3' UTR of the mRNA construct, respectively.

Transfections of the mRNAs are performed by using the $DMP^{CTx}$ technology as follow: one day prior to transfection, cells are seeded separately into a microwell plates and grown in complete medium (EMEM/10% FBS). The next day, cells are transfected either with PBS (negative control), $DMP^{CTx}$ MR1-MOP or MR1. The transfection is carried out by direct addition of mRNA-$DMP^{CTx}$ to the cultured medium in the well, with gentle mixture of the cultured cells as needed.

MR1 Detection by Immunoblot and Immunofluorescence

Both immunoblot and immunofluorescence experiments are performed upon transfection kinetic.

To control the MR1 translation, immunoblot is performed as follows. Culture media is removed, cells are washed with cold PBS and cell pellets are lysed in RIPA (radioimmunoprecipitation assay) buffer (Boston Bioproducts) with a cocktail of protease inhibitors (Sigma). Cells fractions are separated to isolated membrane protein from cytoplasmic soluble proteins. Proteins are then separated by polyacrylamide gel electrophoresis and transferred onto PVDF (polyvinylidene difluoride) membranes by electroblotting. After blocking with 5% nonfat dry milk in TBS-Tween 20 (Boston Bioproducts), membranes are incubated with a primary anti-MR1 or b-actin (control) antibody, followed by incubation with a secondary antibody (e.g., HRP (horseradish peroxidase)-conjugated antibody). Protein detection is then performed using Clarity™ Western ECL Substrate (Bio Rad) and LI-COR® system (LI-COR), respectively.

To control that MR1 is well located at the surface of the cells, immunofluorescence is performed as follows. Cells are grown on coverslips (pre-incubated with 0.2% gelatin for 30 min), rinsed in PBS, and pre-extracted in 0.5% CSK-Triton supplemented with 10 mM ribonucleoside-vanadyl complex (VRC) (New England Biolabs) on ice for 2 min. Cells are then washed once in CSK supplemented with 10 mM VRC, and incubated on ice for 2 min, followed by fixation by 4% paraformaldehyde in PBS at room temperature for 10 min. Cells are then washed twice with PBS and blocked in 1% bovine serum albumin in PBS containing RNase inhibitor (Roche) at room temperature for 20 min. Incubation is carried out at room temperature for 1 hr with primary antibody raised against MR1 (ab229987) at 1/100 in PBS containing 1% bovine serum albumin and RNase inhibitor (Roche). Cells is washed three times in PBS containing 0.02% Tween-20 (PBS-T). After incubating with fluorescent-conjugated goat anti-rabbit secondary antibody at room temperature for 30 min, cells are washed three times in PBS-T. The slides are then mounted with a drop of Vectashield with 4',6-diamidino-2-phenylindole (DAPI). Imaging is performed with a fluorescence microscope (EVOS FL Auto from Thermofisher or Cytation instrument form Biotek).

Results

After transfection, MR1-MOP construct should be translated only in the cancer cell lines, whereas the normal cells will be protected due to the presence of miR122 and miR375 binding sequences in the MOP sequence. Immunoblot results will allow to observe a higher band around ~39kDA, corresponding to the MR1 protein, in the protein lysates from the cancer cells transfected by both constructs and from healthy cells that are transfected by MR1. Protein lysates from the healthy cells transfected by the MR1-MOP construct and from all cell lines transfected with a vehicle control of PBS alone should display reduced MR1 expression. The immunofluorescence experiments will demonstrate that the translated MR1 protein is properly located at the membrane. This observation will mean that the MR1 will be accessible for the MR1-restricted T lymphocytes cells. The kinetics will allow determination at which time, after transfection, the MR1 has the highest abundance and/or location at the surface, which will serve as the point of reference for cell lysis induced by the T cells.

Efficiency of the Cell Lysis by MR1-Restricted T Lymphocytes Cells

To study whether the MR1 translation increase cell lysis by MR1-restricted T lymphocytes cells, cytotoxicity assay is performed by using MC.7.G5 cells from Sewell lab. MC.7.G5 is a T cell clone that recognizes MR1 and kills cancer cells presenting MR1 at the surface (Crowther et al., 2020). Hep3B, BxPC-3, normal hepatocytes and H6c7 cells transfected or not with the different MR1 constructs (target cells) are labeled with mCi chromium (PerkinElmer, Waltham, Mass.), washed with FBS, and allowed to leach in FBS to remove any excess chromium from the cells. After chromium labeling, target cells are washed and plated. MC.7.G5 cells are added to the target cells at the desired MC.7.G5 cell to target cell ratio. The cells were co-cultured in target-cell media supplemented with IL-2 and IL-15. Target cells are also incubated alone or with 1% Triton X-100 detergent to give the spontaneous and total chromium released from the target cells, respectively. After incubation, at 37° C. and 5% CO2, the supernatants are harvested (10% of total volume), mixed with Optiphase supermix scintillation mixture (PerkinElmer) in 96-well polyethylene terephthalate plates (PerkinElmer), sealed, and the amount of released chromium measured indirectly on a 1450 Microbeta counter (PerkinElmer). The percentage of specific target cell lysis by MC.7.G5 cells is calculated according to the following formula: (experimental release [with MC.7.G5 cells and target cells]–spontaneous release from target cells)/ (total release from target cells–spontaneous release from target cells)×100.

Results

The cell lysis induced by MC.7.G5 cells will be enhanced in the cancer cell lines transformed with MR1-MOP and MR1 mRNA construct compared to cancer cells transformed with PBS (negative control). MC.7.G5 will remain inert to healthy cells due to the fact (i) that the healthy hepatocytes and pancreatic cells will not translate MR1 due to the miRNA binding sequences present and (ii) that MC.7.G5 cells does not kill healthy cells.

Example 9

Assessment of Whether MR-1 Increases Infectivity of Co-Infection with HSV, In Vivo Subcutaneous Xenograft of Hep3B and BxPC-3 Cells in PBMC-Humanized Mice To study the recruitment of T lymphocytes to a tumor site, in vivo experiments are performed on human peripheral blood mononuclear cells (PBMC) humanized mice, which permits testing with human T lymphocytes. Humanized mice are developed by injecting PBMCs into immunodeficient mice, such as NSG™/NOG® and BRG mice.

Hep3B and BxPC-3 cells are resuspended in 1:1 PBS: Matrigel™ and then injected on to the right flank of each mouse. Tumor growth is monitored twice a week by observation and palpation. Sufficient and homogeneous tumor size between group is defined as the starting point to perform a treatment trial.

Intra Tumoral Injection of MR1 and Detection of the Translated MR1 Protein

Formulated DMP$^{CTx}$ MR1-MOP, MR1, or saline solution is injected intra-tumorally (IT) in mice multiple times during a treatment period. At different kinetic points, the mice are sacrificed, and the tumors are collected and prepared in FFPE blocks for immunohistochemistry analysis. Non-diseased liver, pancreas, and kidneys are also collected and prepared in FFPE blocks in order to investigate the biodistribution and the organ protection of the formulations. Immunihistochemistry is performed using an anti-MR! primary antibody and a HRP-conjugated secondary antibody.

Results

The IT injection of the formulated DMP$^{CTx}$ MR1-MOP or MR1 should both lead to expression of MR1 at surface of the tumor cells. A differential expression for the MR1 will be achieved in tumoral cells and non-diseased liver, pancreas, and kidney cells when the MR1-MOP is administrated in vivo due to the presence of the miRNA binding sites in the MOP sequence. However, the absence of MOP sequence in the MR1 construct will induce a significant increase of the MR1 detection in non-diseased liver, pancreas, and kidneys.

Tumor Growth and Recruitment of T-Lymphocytes at the Tumor Site

After IT injections of the DMP$^{CTx}$ MR1-MOP, MR1, or saline solution, the size of tumors is measured by caliper every 3 or 4 days in order to observe the effect of the treatment on tumor growth.

At different timepoints after injection, mice are sacrificed and half of the tumor, the liver, the colon, and the kidney is dissociated in single cells. Organs are minced into small pieces and cells are dissociated by incubation at 37° C. with Collagenase A (Sigma) and DNAse (StemCell). Single cells are stained with Fixable Live/Dead Violet Dye VIVID and the surface fluorescent-conjugated antibodies: anti-CD3 (PerCP) clone UCHT1 (BioLegend), anti-CD8 (FITC) clone BW135/80 (Miltenyi Biotec). The single stained cells are then observed by cytometry to determine the rate of the recruitment of the T cells at the tumor site.

In parallel, the other half of the tumor, the liver, the colon, and the kidney are collected and prepared in FFPE blocks for immunohistochemistry analysis using the protocol described above. Antibodies against cleaved caspase-3 (Cell Signaling Technology), Ki67 (Pierce), and CD3 (BioLegend) and CD8 (Miltenyi Biotec) are used to observe apoptosis, to determine the rate of proliferative cells and the recruitment of T cells including, but not limited to, unconventional MAIT cells at the tumor site respectively.

Results

The growth of the tumors treated with MR1-MOP or MR1 should be decreased, and the size of the tumor is expected to be smaller than tumors treated with saline solution, due to the cell lysis induced by the recruitment of the MR1-restricted T lymphocytes cells. Moreover, the tumors treated with MR1-MOP or MR1 will display higher apoptosis (caspase-3 staining) with a lower proliferative rate cells (Ki67 staining) and the recruitment of T cells at the tumor site will be increase, compared to the saline treated tumor. This is due to the expression of MR1 that increases anti-tumoral effect of the MR1-restricted T lymphocytes cells. Liver, pancreas and kidneys will be protected in the mice treated by MR1-MOP, whereas these organs will display higher apoptosis (caspase-3 staining) with a lower proliferative rate cells (Ki67 staining) and a higher recruitment of T cells in mice treated with MR1 without the MOP sequence.

Example 10

ORF Selection of the Type I Interferon Receptor, B18R, Together with OPS Protection for Enhanced Oncolytic Virus Activity The present invention aims to reduce anti-viral effects linked to interferon mediated responses that can reduce the effectiveness of oncolytic viral therapies, such as poxviruses including Vaccinia virus, when used on tumor cells. B18R limits the effectiveness of IFN alpha produced following TLR activation (Waibler, Z. Journal of Virology; February 2009, 1563-1571), and limits adaptive T cell responses (Gomez, C. E. et al. Journal of Virology; March 2012, 5026-5038).

For instance, an mRNA encoding B18R as the ORF is modified as described in previous examples to include a MOP having at least three similar or different miRNA target sequences, and differential mRNA expression is evaluated in cancer cell lines and corresponding normal primary cells for at least one organ comprised from the group consisting of: liver; pancreas; brain and CNS; kidney; spleen; gut, including oesophagus, stomach, intestine, colon, and rectum; lung; skin and breast. Cancer cells and corresponding normal cells are transfected with the modified B18R mRNA construct.

B18R mRNAs Constructs

For the following embodiment, the vaccinia virus (Western Reserve strain) B18R mRNA is used (GenBank Acc: YP233081). This mRNA is followed by a 3' UTR that comprises the perfect match MOP sequence: miR122-miR192-miR30a (122-192-30a). The construct is synthetized by Trilink Biotechnologies (San Diego, Calif.) from a generated DNA sequence. These mRNAs resemble fully processed, capped and polyadenylated mRNAs and are ready for translation by the ribosome. As a negative control, the same construct is synthetized without the MOP sequence (B18R-w/o_MOP).

In Vitro B18R Transfections

To study whether B18R may assist in persistence and replication of a co-administered oncolytic virus, human hepatocytes are used because they are sensitive to oncolytic Vaccinia Virus (oVV) infection. For in vitro transfection of the B18R constructs, human liver hepatocarcinoma Hep3B are purchased from ATCC (ATCC® HB-8064™). Normal human hepatocytes are used to observe liver protection as the exogenous B18R will be not translated in the healthy hepatocytes due to the miR-122 binding sequence protection.

Transfections of the mRNAs are performed by using the DMP$^{CTx}$ technology as follows: one day prior to transfection, cells are seeded separately into a microwell plate. The next day, cells are transfected either with PBS alone (negative control), DMP$^{CTx}$ B18R-MOP or B18R. The transfection is carried out by direct addition of mRNA-DMP$^{CTx}$ to the cultured medium in the well, with gentle mixture of the cultured cells as needed.

B18R Detection by Immunoblot

At various time points upon transfection, immunoblot is performed in order to control the B18R translation as follows. Culture media is removed, cells are washed with cold PBS and cell pellets are lysed in RIPA (radioimmunoprecipitation assay) buffer (Boston Bioproducts) with a cocktail of protease inhibitors (Sigma). Cells fractions are separated to isolated membrane protein from cytoplasmic soluble proteins. Proteins are then separated by polyacrylamide gel electrophoresis and transferred onto PVDF (polyvinylidene difluoride) membranes by electroblotting. After blocking with 5% nonfat dry milk in TBS-Tween 20 (Boston Bioproducts), membranes are incubated with a primary anti-B18R or b-actin (control) antibody, followed by incubation with a secondary antibody (e.g., HRP (horseradish peroxidase)-conjugated antibody). Protein detection is then performed using Clarity™ Western ECL Substrate (Bio Rad) and LI-COR® system (LI-COR), respectively.

Results

After transfection, B18R-MOP construct will be translated only in the Hep3B cancer cells, whereas the healthy hepatocytes will be spared due to the high level of miR-122 in non-diseased liver. DMP$^{CTx}$ B18R construct will lead to high protein expression in both healthy and cancer cell lines due to the absence of the MOP sequence. Immunoblot results will allow to observe a band around ~80kDA, corresponding to the B18R protein, in the protein lysates from the Hep3B cells transfected by both constructs, whereas the band will be present only in the healthy hepatocytes that are transfected by DMP$^{CTx}$ B18R without MOP sequence. Protein lysates from the healthy hepatocytes transfected by the B18R-MOP construct and from both cell types transfected with a vehicle control of PBS alone will show no band. Samples will be prepared at different timepoints after transfection to determine when the highest amount of B18R protein is expressed.

Efficiency of the Oncolytic Vaccinia Virus Infection

As mentioned previously, B18R improves the antitumor activity of oncolytic virus, such as oVV, by blocking the interferon antiviral defense mechanism (Fu et al., 2012; Mol. Ther. Vol. 20, Issue 10: 1871-1881). It has been observed in vitro that B18R allows oncolytic viruses to resist the inhibitory effect of externally added IFN in tumor cells. To determine whether translated B18R in Hep3B cells allows persistence and replication of oVV lacking B18R, in vitro infections are performed as follow. Hep3B and normal hepatocytes are transfected or not with DMP$^{CTx}$ B18R-MOP or B18R mRNAs. Before, at the same time, or after the transfection, cells are infected with serial dilutions of either oVV deleted for B18R (oVV_DB18R) or not (oVV_WT), by using the Western strain DJ2R, eGFP$^+$, DI4L, with or without the presence of IFNs in the media.

At different timepoints post-infection, the viability of transfected cell lines is measured by MTT assay according to vendor instructions (Cell Proliferation kit I, Sigma). Absorbance is measured at 550-600 nm with a 96-well plate to determine dose-response curves and 50% effective dose values (ED50).

Because the oVV Western strain used is eGFP positive, the replication of the virus can be followed by quantification of the fluorescent signal on a plate reader.

Results

Hep3B cancer cells transfected with the B18R-MOP or B18R mRNA constructs will both express high level of B18R protein, which should induce a resistance to the externally added IFN. Thus, transfected cells will be infected and killed by the oVV_DB18R. The heathy hepatocytes transfected with B18R mRNA construct in presence of IFN will give similar results. However, healthy hepatocytes transfected by the B18R-MOP mRNA construct will exhibit a significant low susceptibility to oVV_DB18R in presence of IFN due to the inhibition of the high amount of miRNA-122 in non-diseased liver and the presence of the MOP sequence in the mRNA construct.

All transfected cell lines will be sensitive to the infection by oVV_WT, in presence and in absence of IFN. Indeed, the B18R protein will be translated by the virus itself. Finally, all the transfected cells lines will be sensitive to either oVV_DB18R or oVV_WT in absence of IFN in the media. Altogether, these results will show that exogenous transfected B18R acts as a therapeutic enhancement factor and with the present formulation will improve oncolytic virus replication and persistence in presence of IFN.

Example 11

B18R In Vivo Experiments

Subcutaneous Xenograft of Hep3B and BxPC-3 Cells in PBMC-Humanized Mice

To determine whether exogenous B18R blocks interferon alpha transmembrane signaling that induces persistence and replication of oVV, in vivo experiments are performed on human peripheral blood mononuclear cells (PBMC) humanized mice. Humanized mice are developed by injecting PBMCs into immunodeficient mice, such as NSG™/NOG® and BRG mice.

Hep3B cells are resuspended in 1:1 PBS:Matrigel™ and then injected on to the right flank of each mouse. Tumor growth is monitored twice a week by observation and palpation. Sufficient and homogeneous tumor size between group is defined as the starting point to perform a treatment trial.

Intra Tumoral Injection of B18R and Detection of the Translated B18R Protein

Formulated DMP$^{CTx}$ B18R-MOP, B18R, or saline solution is injected intra-tumorally (IT) in mice during a treatment period. At various timepoints, the mice are sacrificed, and tumors, as well as non-diseased organs such as liver and kidney are collected, and flash frozen in liquid $N_2$. Each tissue is ground in $N_2$, filtered and powder is resuspended in RIPA buffer for immunoblot assay as described above.

Results

The IT injection of the DMP$^{CTx}$ B18R-MOP or B18R will both induce translation of B18R in the tumor cells. A differential expression for the B18R will be achieved between tumoral cells and non-diseased liver with the B18R-MOP. However, the absence of the MOP in the B18R mRNA will lead to high level of B18R in the healthy liver and kidney cells.

Efficiency of the Oncolytic Vaccinia Virus (oVV)

Before, at the same time, or after formulated DMP$^{CTx}$ B18R-MOP, B18R, or saline solution treatment is administered to the tumour, randomly grouped mice are treated by intravenous injection of the oncolytic vaccinia virus (Western strain; DJ2R, eGFP$^+$, DI4L) or virus buffer. The size of tumors is measured by caliper every 3 or 4 days in order to observe the combined therapeutic effect on tumor growth. At various timepoints after treatment, mice are sacrificed. Tumors and livers are then collected and prepared in FFPE blocks for further immunohistochemistry analysis. IHC is performed with antibodies against cleaved caspase-3 (Cell Signaling Technology) to observe apoptosis, Ki67 (Pierce) to determine the rate of proliferative cells followed by incubation with appropriate HRP-conjugated secondary antibodies. Since the oVV strain used in this experiment carries the eGFP locus, the replication and the persistence of the oVV into the tumor site can be follow by IHC assay with anti-GFP antibody.

Results

The tumors pre-treated with B18R-MOP or B18R will be more susceptible to oVV infection and will be significantly smaller in size, displaying higher GFP signal (infection marker) and apoptosis (caspase-3 staining), with a lower proliferative rate cells (Ki67 staining) compared to the tumors treated with oVV alone or with virus buffer. The liver will be protected from oVV infection in the mice treated with B18R-MOP compared to mice treated with B18R without the MOP sequence, whose organs will be significantly more susceptible to the oVV infection. It will be possible to observe a better effect on tumor regression when the tumors are pre-treated with B18R before oVV infection, than when the B18R and oVV are co-administered at the same time or when the B18R is injected after the oHSV injection. Because intratumoral B18R injection will prime the tumor to the oVV infection by decreasing the immune system responses within the tumor, we will observe a higher oVV replication rate and persistence of the oVV in the tumor compared to the non B18R pre-treated tumor.

Example 12

Transfection of Human PBMCS with IL-12 and GM-CSF mRNAs

IL-12 and/or GM-CSF are immunomodulatory cytokines that may be utilised in combination with anti-tumour therapies such as in combination with therapeutic viruses, or as adjuvants co-administered with vaccine compositions. In this experiment, DMP$^{CTx}$ hGM-CSF (human GM-CSF) and hdcIL-12 (double chain human IL-12 p70) or hscIL-12 (single chain human IL-12 p70), with or without a MOP sequence were administered in vitro to human PBMCs at a range of dosages. Noncoding mRNA for hscIL-12 p70 and hGMCSF we also used as negative control (NC). The expression of protein within the cell was shown to be linked to the dose of mRNA administered.

In Vitro Transfection Efficiency and Toxicity of LNP-Immunomodulators IL-12 and GM-CSF PBMC cells from 5 different donors (18-55 years old) were obtained from AllCells and cultured in suspension in AIM V medium (Gibco) at 37° C. in an atmosphere of 5% CO2. 300,000 PBMC cells were seeded per well in a round-bottom 96-well plate and transfected with DMP$^{CTx}$ formulated mRNAs encoding either IL-12 single or double chain variants or GM-CSF, with or without MOP sequence (see Table 6, below). Positive control to validate PBMCs are functioning normally was performed with wells containing 300,000 PBMC cells with LPS (ThermoFisher, 00-4976) added to the media at a final concentration of 100 ng/mL. Negative controls were performed in parallel, with wells without PBMC cells nor LNP transfection (BG-C), wells with only 150,000 non-transfected PBMC cells (LC), and wells with 300,000 non-transfected PBMC cells (HC).

4 hours after transfection, human AB heat-inactivated serum (Sigma) was added to a final concentration of 1%. 6 hours after transfection, 60 μL of the supernatant of each well were transferred to a new 96-well plate, cells were removed by centrifugation and the supernatants were frozen at −80° C. for MSD assay. 21 hours after transfection, Tween-20 was added to HC wells at a final concentration of 1.1%. 24 hours after transfection, all supernatants from each well were collected by centrifugation. 60 μL of supernatant were frozen at −80° C. for MSD assay and the remaining 130 μL were frozen at −80° C. for LDH assay.

MSD assay for human cytokines IL-12p70 and GM-CSF analysis was performed using a U-PLEX assay (Meso Scale Discovery) and following the manufacturer's instructions. The data were plotted into a bar graph using Graph Pad Prism.

LDH assay was performed using the Cytotoxicity Detection KitPLUS (LDH) from Roche (4744926001) and following the manufacturer's instructions.

Results

FIGS. 12A-12B show detectable levels of both human IL-12 p70 and GM-CSF from MOP containing constructs 6 h after transfection. The presence of the MOP in the mRNA minimises off-target expression in liver, skin, muscle and kidney tissues. The LDH assay showed that DMP$^{CTx}$ mRNAs encoding for either IL-12 single or double chain variants or GM-CSF did not induce significant cellular cytotoxicity in the PBMCs above the negative control.

TABLE 6

ORF and 3' UTR for IL-12 MOP and GM-CSF MOP

Human single chain IL-12 MOP (hscIL12-MOP) with 3' UTR perfect matching complementary sequence to miR-122-5P, miR-1-3P, miR-203a-3P, miR-30a-5P are underlined
[SEQ ID NO: 62]
AUGUGUCACCAGCAGUUGGUCAUCUCUUGGUUUUCCCUGGUUUUUCUGGCAUCUCCCCU
CGUGGCCAUAUGGGAACUGAAGAAAGAUGUUUAUGUCGUAGAAUUGGAUUGGUAUCCGG
AUGCCCCUGGAGAAAUGGUGGUCCUCACCUGUGACACCCCUGAAGAAGAUGGUAUCACC
UGGACCUUGGACCAGAGCAGUGAGGUCUUAGGCUCUGGCAAAACCCUGACCAUCCAAGU
CAAAGAGUUUGGAGAUGCUGGCCAGUACACCUGUCACAAAGGAGGCGAGGUUCUAAGCC
AUUCGCUCCUGCUGCUUCACAAAAAGGAAGAUGGAAUUGGUCCACUGAUAUUUUAAAG
GACCAGAAAGAACCCAAAAAUAAGACCUUUCUAAGAUGCGAGGCCAAGAAUUAUUCUGG
ACGUUUCACCUGCUGGUGGCUGACGACAAUCAGUACUGAUUUGACAUUCAGUGUCAAAA
GCAGCAGAGGCUCUUCUGACCCCCAAGGGGUGACGUGCGGAGCUGCUACACUCUCUGCA TABLE 6-continued ORF and 3' UTR for IL-12 MOP and GM-CSF MOP GAGAGAGUCAGAGGGGACAACAAGGAGUAUGAGUACUCAGUGGAGUGCCAGGAGGACAG
UGCCUGCCCAGCUGCUGAGGAGAGUCUGCCCAUUGAGGUCAUGGUGGAUGCCGUUCACA
AGCUCAAGUAUGAAAACUACACCAGCAGCUUCUUCAUCAGGGACAUCAUCAAACCUGAC
CCACCCAAGAACUUGCAGCUGAAGCCAUUAAAGAAUUCUCGGCAGGUGGAGGUCAGCUG
GGAGUACCCUGACACCUGGAGUACUCCACAUUCCUACUUCUCCCUGACAUUCUGCGUUC
AGGUCCAGGGCAAGAGCAAGAGAGAAAAGAAAGAUGAGUCUUCACGGACAAGACCUCA
GCCACGGUCAUCUGCCGCAAAAAUGCCAGCAUUAGCGUGCGGGCCCAGGACCGCUACUA
UAGCUCAUCUUGGAGCGAAUGGGCAUCUGUGCCCUGCAGUGGUGGCGGUGGCGGCGGAU
CUAGAAACCUCCCCGUGGCCACUCCAGACCCAGGAAUGUUCCCAUGCCUUCACCACUCC
CAAAACCUGCUGAGGGCCGUCAGCAACAUGCUCCAGAAGGCCAGACAAACUCUAGAAUU
UUACCCUUGCACUUCUGAAGAGAUUGAUCAUGAAGAUAUCACAAAAGAUAAAACCAGCA
CAGUGGAGGCCUGUUUACCAUUGGAAUUAACCAAGAAUGAGAGUUGCCUAAAAUUCCAGA
GAGACCUCUUUCAUAACUAAUGGGAGUUGCCUGGCCUCCAGAAAGACCUCUUUUAUGAU
GGCCCUGUGCCUUAGUAGUAUUUAUGAAGACUUGAAGAUGUACCAGGUGGAGUUCAAGA
CCAUGAAUGCAAAGCUUCUGAUGGAUCCUAAGAGGCAGAUCUUUCUAGAUCAAAACAUG
CUGGCAGUUAUUGAUGAGCUGAUGCAGGCCCUGAAUUUCAACAGUGAGACUGUGCCACA
AAAAUCCUCCCUUGAAGAACCGGAUUUUUAUAAAACUAAAAUCAAGCUCUGCAUACUUC
UUCAUGCUUUCAGAAUUCGGGCAGUGACUAUUGAUAGAGUGAUGAGCUAUCUGAAUGCU
UCCUAACAAACACCAUUGUCACACUCCAUUUAAAAUACAUACUUCUUUACAUUCCAUUU
AAACUAGUGGUCCUAAACAUUUCACUUUAAACUUCCAGUCGAGGAUGUUUACA Human single chain IL-12 without MOP
[SEQ ID NO: 63]
AUGUGUCACCAGCAGUUGGUCAUCUCUUGGUUUUUCCCUGGUUUUUCUGGCAUCUCCCCU
CGUGGCCAUAUGGGAACUGAAGAAAGAUGUUUAUGUCGUAGAAUUGGAUUGGUAUCCGG
AUGCCCUGGAGAAAUGGUGGUCCUCACCUGUGACACCCCUGAAGAAGAUGGUAUCACC
UGGACCUUGGACCAGAGCAGUGAGGUCUUAGGCUCUGGCAAAACCCUGACCAUCCAAGU
CAAAGAGUUUGGAGAUGCUGGCCAGUACACCUGUCACAAAGGAGGCGAGGUUCUAAGCC
AUUCGCUCCUGCUGCUUCACAAAAAGGAAGAUGGAAUUUGGUCCACUGAUAUUUUAAAG
GACCAGAAAGAACCCAAAAAUAAGACCUUUCUAAGAUGCGAGGCCAAGAAUUAUUCUGG
ACGUUUCACCUGCUGGUGGCUGACGACAAUCAGUACUGAUUUGACAUUCAGUGUCAAAA
GCAGCAGAGGCUCUUCUGACCCCCAAGGGGUGACGUGCGGAGCUGCUACACUCUCUGCA
GAGAGAGUCAGAGGGGACAACAAGGAGUAUGAGUACUCAGUGGAGUGCCAGGAGGACAG
UGCCUGCCCAGCUGCUGAGGAGAGUCUGCCCAUUGAGGUCAUGGUGGAUGCCGUUCACA
AGCUCAAGUAUGAAAACUACACCAGCAGCUUCUUCAUCAGGGACAUCAUCAAACCUGAC
CCACCCAAGAACUUGCAGCUGAAGCCAUUAAAGAAUUCUCGGCAGGUGGAGGUCAGCUG
GGAGUACCCUGACACCUGGAGUACUCCACAUUCCUACUUCUCCCUGACAUUCUGCGUUC
AGGUCCAGGGCAAGAGCAAGAGAGAAAAGAAAGAUGAGUCUUCACGGACAAGACCUCA
GCCACGGUCAUCUGCCGCAAAAAUGCCAGCAUUAGCGUGCGGGCCCAGGACCGCUACUA
UAGCUCAUCUUGGAGCGAAUGGGCAUCUGUGCCCUGCAGUGGUGGCGGUGGCGGCGGAU
CUAGAAACCUCCCCGUGGCCACUCCAGACCCAGGAAUGUUCCCAUGCCUUCACCACUCC
CAAAACCUGCUGAGGGCCGUCAGCAACAUGCUCCAGAAGGCCAGACAAACUCUAGAAUU
UUACCCUUGCACUUCUGAAGAGAUUGAUCAUGAAGAUAUCACAAAAGAUAAAACCAGCA
CAGUGGAGGCCUGUUUACCAUUGGAAUUAACCAAGAAUGAGAGUUGCCUAAAAUUCCAGA
GAGACCUCUUUCAUAACUAAUGGGAGUUGCCUGGCCUCCAGAAAGACCUCUUUUAUGAU
GGCCCUGUGCCUUAGUAGUAUUUAUGAAGACUUGAAGAUGUACCAGGUGGAGUUCAAGA
CCAUGAAUGCAAAGCUUCUGAUGGAUCCUAAGAGGCAGAUCUUUCUAGAUCAAAACAUG
CUGGCAGUUAUUGAUGAGCUGAUGCAGGCCCUGAAUUUCAACAGUGAGACUGUGCCACA
AAAAUCCUCCCUUGAAGAACCGGAUUUUUAUAAAACUAAAAUCAAGCUCUGCAUACUUC
UUCAUGCUUUCAGAAUUCGGGCAGUGACUAUUGAUAGAGUGAUGAGCUAUCUGAAUGCU
UCCUAA

Human GMCSF 4MOP mRNA (hGMCSF-MOP) perfect matching
complementary sequence to miR-122-5P, miR-1-3P, miR-203a-3P,
miR-30a-5P are underlined
[SEQ ID NO: 64]
AUGUGGCUGCAGAGCCUGCUGCUCUUGGGCACUGUGGCCUGCAGCAUCUCUGCACCCGC
CCGCUCGCCCAGCCCCAGCACGCAGCCCUGGGAGCAUGUGAAUGCCAUCCAGGAGGCCC
GGCGUCUCCUGAACCUGAGUAGAGACACUGCUGCUGAGAUGAAUGAAACAGUAGAAGUC
AUCUCAGAAAUGUUUGACCUCCAGGAGCCGACCUGCCUACAGACCCGCCUGGAGCUGUA
CAAGCAGGGCCUGCGGGGCAGCCUCACCAAGCUCAAGGGCCCCUUGACCAUGAUGGCCA
GCCACUACAAGCAGCACUGCCCUCCAACCCCGGAAACUUCUGUGCAACCCAGAUUAUC
ACCUUUGAAAGUUUCAAAGAGAACCUGAAGGACUUUCUGCUUGUCAUCCCCUUUGACUG
CUGGGAGCCAGUCCAGGAGUGACAAACACCAUUGUCACACUCCAUUUAAAAUACAUACU
UCUUUACAUUCCAUUUAAACUAGUGGUCCUAAACAUUUCACUUUAAACUUCCAGUCGAG
GAUGUUUACA Human GM-CSF without MOP
[SEQ ID NO: 65]
AUGUGGCUGCAGAGCCUGCUGCUCUUGGGCACUGUGGCCUGCAGCAUCUCUGCACCCGC
CCGCUCGCCCAGCCCCAGCACGCAGCCCUGGGAGCAUGUGAAUGCCAUCCAGGAGGCCC
GGCGUCUCCUGAACCUGAGUAGAGACACUGCUGCUGAGAUGAAUGAAACAGUAGAAGUC
AUCUCAGAAAUGUUUGACCUCCAGGAGCCGACCUGCCUACAGACCCGCCUGGAGCUGUA
CAAGCAGGGCCUGCGGGGCAGCCUCACCAAGCUCAAGGGCCCCUUGACCAUGAUGGCCA
GCCACUACAAGCAGCACUGCCCUCCAACCCCGGAAACUUCUGUGCAACCCAGAUUAUC
ACCUUUGAAAGUUUCAAAGAGAACCUGAAGGACUUUCUGCUUGUCAUCCCCUUUGACUG
CUGGGAGCCAGUCCAGGAGUGA

Example 13

In Vivo Biodistribution of DMP$^{CTx}$ of Luciferase Expressing mRNAs with Mop Sequences To investigate the potential of the present invention to demonstrate differential expression of a particular ORF in vivo, firefly luciferase (FLuc) mRNA was modified as in Example 4 to include two different combinations of three miRNA target sequences in the 3' UTR of the mRNA construct. The first mRNA MOP sequence contains the target sequences for Let7b, miRNA-126 and miRNA-30a (Group 2). The second mRNA MOP sequence contains the target sequences for miRNA-122, miRNA-192, miRNA-30a (Group 3). All MOP constructs contained perfect match target sequences to the corresponding miRNAs. A control FLuc mRNA sequence was also used without MOP sequences in the construct (Group1).

Formulations were made as described above and had the following characteristics.

TABLE 7

Delivery Formulations for in vivo Biodistribution

| Group | mRNA | Conc (mg/mL) | Encapsulation Efficiency (%) | $Z_{ave}$ (nm) | PDI |
|---|---|---|---|---|---|
| 1 | FLuc | 0.319 | 95.2 | 70.8 | 0.117 |
| 2 | FLuc-let7b-126-30a PM | 0.284 | 92.8 | 73.6 | 0.116 |
| 3 | FLuc-122-192-30a PM | 0.359 | 95.6 | 73.7 | 0.099 |

Animals. All experiments were performed at Crown Biosciences, Nottingham UK in accordance with all local rules and regulations. All mice were obtained from Charles River.

Non-Tumoral Biodistribution Studies. Healthy, female balb/c mice 7-9 weeks old were injected with 1 mg/kg formulation (DMP$^{CTx}$-mRNA) encoding for firefly luciferase (FLuc) either with or without MOP sequences through a bolus tail vein injection. Whole body Images were taken pre-dosing (0 h), and 3.5 h, and 24 h post dose and the amount of luciferase signal was quantified using Living Image Software (Caliper LS, US). 15 min prior to imaging, mice were injected (subcutaneous) with 150 mg/kg d-Luciferin, then anesthetized 10 min later and placed in an imaging chamber for luminescence detection (ventral and dorsal views). At the 24 h time point, the liver, kidneys, spleen, and lungs were removed and imaged ex vivo.

Tumoral Biodistribution Studies. Human liver cancer cells (Hep3B cells) (2×10$^6$ cells) were implanted subcutaneously in the left flank of 8-10 week old Fox Chase SCID mice. Mice were sorted into study groups based on caliper measurements of tumor burden, with tumor sizes of approximately 100 mm$^3$ chosen. Formulation (DMP$^{CTx}$-mRNA) encoding for firefly luciferase (FLuc) either with or without MOP sequences was then injected intratumorally at a dose of 1 mg/kg. Whole body Images were taken pre-dosing (0 h), and 3.5 h, and 24 h post dose and the amount of luciferase signal was quantified using Living Image Software (Caliper LS, US). 15 min prior to imaging, mice were injected (subcutaneous) with 150 mg/kg d-Luciferin, then anesthetized 10 min later and placed in an imaging chamber for luminescence detection (ventral and dorsal views). At the 24 h time point, the tumor, liver, kidneys, spleen, and lungs were removed and imaged ex vivo.

Results

Figure 16B:
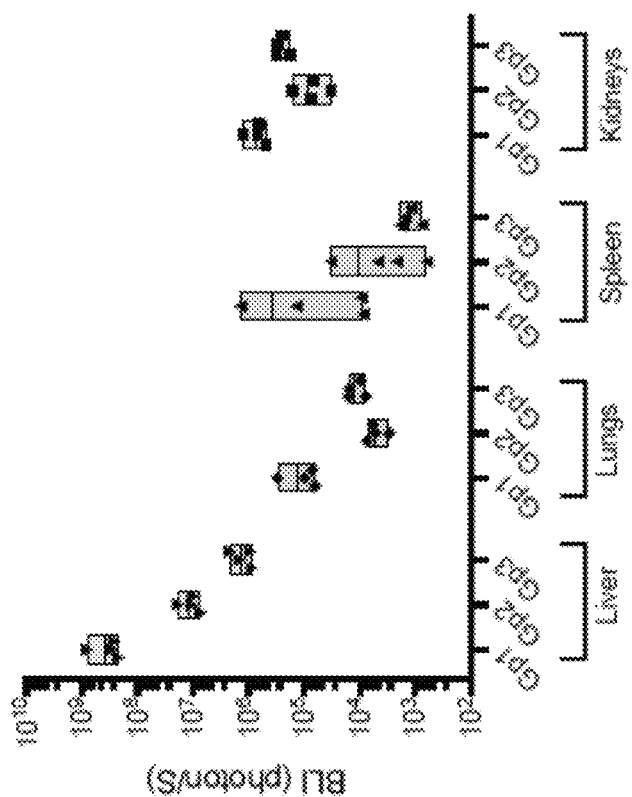
FIGS. 16A-16B show results of an in vivo biodistribution experiment in mice, demonstrating that (FIG. 16A) after 3.5 hours post-transfection (T3.5 h) with compositions of the invention, high levels of Luciferase expression can be seen in all groups through whole body imaging, including the MOP containing constructs (Group 2 and 3) and the control group with no MOP construct (Group 1); but significant down regulation of Luciferase expression is seen in MOP containing compositions after 24 hours (T24 h). In (FIG. 16B) ex vivo imaging of the organs after 24 hours show decreased Luciferase expression in the liver, lungs, spleen, and kidney for mice in Group 2 and 3 (MOP containing constructs) as compared to Group 1 (no MOP control).
Figure 16A:
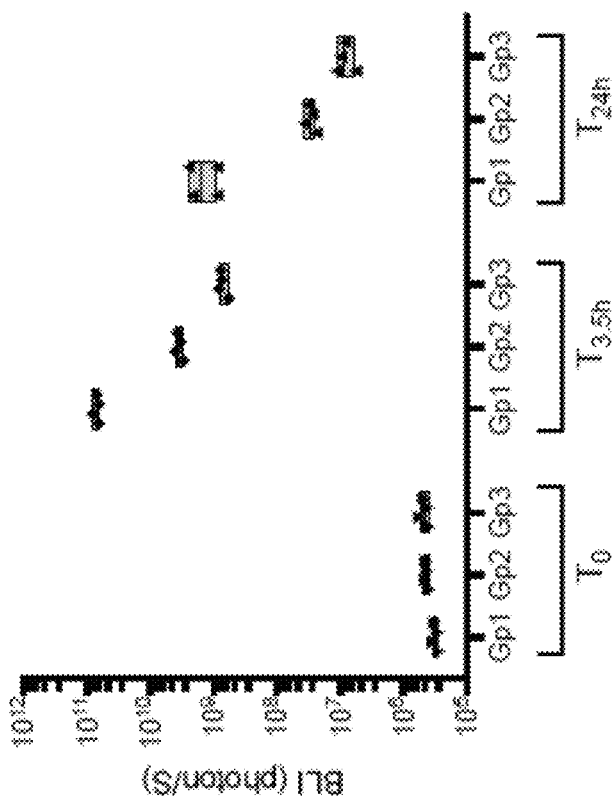

FIG. 16A shows that after 3.5 hours post-transfection, high levels of Luciferase expression can be seen in all groups through whole body imaging, including the MOP containing constructs (Group 2 and 3) and the control group with no MOP construct (Group 1). However, there are 1-2 orders of magnitude less protein expression with the two MOP containing constructs. This trend remains after 24 hours, where there is slightly less overall protein expression in all groups.

The presence of the MOP is surprisingly effective in minimizing off-target expression in vivo in tissues of the liver, lungs, spleen, and kidneys. In FIG. 16B, ex vivo imaging of the organs show decreased Luciferase expression in the liver (miR-122), lungs (let7b, miR-126, miR30a), spleen (Let7b, miR-126), and kidney (miR-192, miR-30a) for mice in Group 2 and 3 (MOP containing constructs) as compared to Group 1 (no MOP control), confirming that both MOP constructs provide valuable multi organ protection from expression of the ORF.

While it is important to minimize off target effects in healthy tissue, it is also important to ensure that protein expression still occurs in targeted tissues such as in a tumor. Table 8 shows that protein expression was maintained at the same order of magnitude for all three groups, when a Hep3B liver tumor was present. Additionally, Luciferase expression in the healthy liver decreases 2-3 orders of magnitude when either MOP is present as was seen in the non-tumor bearing in vivo study.

TABLE 8

BLI Values (photon/S) Obtained in ex vivo Imaging

| | Ex vivo imaging (photon/S) | |
|---|---|---|
| Group | Tumor | Liver |
| 1 FLuc | $4.02 \times 10^7$ | $2.09 \times 10^6$ |
| 2 FLuc-let7b-126-30a PM | $3.33 \times 10^7$ | $3.75 \times 10^4$ |
| 3 FLuc-122-192-30a PM | $1.81 \times 10^7$ | $2.13 \times 10^3$ |

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims. Any non-human nucleic acid and/or polypeptide sequences that have been included in constructs and vectors according to embodiments of the invention have been obtained from sources within the UK, USA and European Union. To the inventor's knowledge, no genetic resources that would be subject to access and benefit sharing agreements, or associated traditional knowledge, has been utilised in the creation of the present invention.

What is claimed is:

1. A composition comprising:
    at least a first mRNA construct comprising at least a first open reading frame (ORF), wherein the ORF is operatively linked to at least one untranslated region (UTR), wherein the UTR comprises at least a first, second, and a third micro-RNA (miRNA) target sequence, and wherein each of the at least first, second, and third miRNA target sequences are optimised to each hybridise with a different corresponding miRNA sequence; further comprising at least a second mRNA construct comprising at least a second open reading frame (ORF), wherein the second ORF encodes a proinflammatory cytokine selected from the group consisting of: IL-1; IL-2; IL-3; IL-4; IL-5; IL-6; IL-7; IL-8; IL-9; IL-10; IL-11; IL-12; IL-15; IL-17; IL-21; TGF-beta; IFNγ; IFNα; IFNβ; TNFα; M-CSF; G-CSF; and GM-CSF,
    wherein the first ORF encodes an antigen selected from: a bacterial protein and/or a viral protein; and
    an in vivo delivery composition;
    wherein the first and second mRNA constructs are comprised within or adsorbed to the delivery composition.

2. The composition of claim 1 comprising:
    an open reading frame (ORF) encoding an antigen comprising all or part of a coronavirus protein.

3. The composition of claim 2, wherein the coronavirus protein is selected from a coronavirus spike, envelope, membrane, or nucleocapsid protein.

4. The composition of claim 3, wherein the coronavirus protein is a SARS-CoV-2 spike protein.

5. The composition of claim 4, wherein the ORF encodes the Receptor Binding Domain of a SARS-CoV-2 spike protein.

6. The composition of claim 1, wherein the delivery composition is selected from the group consisting of a particle, a polymeric particle; a liposome; a lipidoid particle; and a viral vector.

7. The composition of claim 1, wherein the delivery composition comprises a lipid, phospholipid, cholesterol and a polyethylene glycol (PEG).

8. The composition of claim 1, wherein the second ORF codes for a cytokine selected from the group consisting of: IL-7; IL-15; IL-17; and IL-21.

9. The composition of claim 1, wherein the at least a first and second miRNA target sequences include one or more sequences that bind with an miRNA selected from the group consisting of miRNA-122; miRNA-125; miRNA-199; miRNA-124a; miRNA-126; Let7 miRNA family; miRNA-375; miRNA-141; miRNA-142; miRNA-148a/b; miRNA-143; miRNA-145; miRNA-194; miRNA-200c; miRNA-203a; miRNA-205; miRNA-1; miRNA-133a; miRNA-206; miRNA-34a; miRNA-192; miRNA-194; miRNA-204;

miRNA-215; miRNA-30 a,b,c; miRNA-877; miRNA-4300; miRNA-4720; and miRNA-6761.

10. The composition of claim 1, wherein the at least a first and second miRNA target sequences are selected from one or more of the sequences of SEQ ID NOs: 44-57.

11. A method of stimulating an immune response in a subject comprising administering to the subject in need thereof an effective amount of a composition according to claim 1.

12. The method of claim 11, wherein the composition is administered orally, intravenously, topically, intratumorally, intralesionally, subcutaneously, intra-muscularly, intranasally, intrathecally, intra-arterially and/or through inhalation.

13. The composition of claim 1, wherein the second ORF codes for an IL-12 protein, or a derivative, agonist or homologue thereof.

14. The composition of claim 1, wherein the first mRNA further comprises at least a second open reading frame (ORF), wherein the second ORF encodes a proinflammatory cytokine selected from the group consisting of: IL-1; IL-2; IL-3; IL-4; IL-5; IL-6; IL-7; IL-8; IL-9; IL-10; IL-11; IL-12; IL-15; IL-17; IL-21; TGF-beta; IFNγ; IFNα; IFNβ; TNFα; M-CSF; G-CSF; and GM-CSF.

15. The composition of claim 14, wherein the second ORF codes for a cytokine selected from the group consisting of: IL-7; IL-15; IL-17; or IL-21.

16. The composition of claim 1, wherein the second ORF is operatively linked to at least one untranslated region (UTR), wherein the UTR comprises at least a fourth, a fifth and a sixth miRNA target sequence, and wherein each of the at least a fourth, fifth and sixth miRNA target sequences are optimised to each hybridise with a different corresponding miRNA sequence.

17. The composition of claim 16, wherein the at least a fourth, fifth and sixth miRNA target sequences include one or more sequences that bind with an miRNA selected from the group consisting of miRNA-122; miRNA-125; miRNA-199; miRNA-124a; miRNA-126; Let7 miRNA family; miRNA-375; miRNA-141; miRNA-142; miRNA-148a/b; miRNA-143; miRNA-145; miRNA-194; miRNA-200c; miRNA-203a; miRNA-205; miRNA-1; miRNA-133a; miRNA-206; miRNA-34a; miRNA-192; miRNA-194; miRNA-204; miRNA-215; miRNA-30 a,b,c; miRNA-877; miRNA-4300; miRNA-4720; and miRNA-6761.

18. The composition of claim 17, wherein the at least a fourth, fifth and sixth miRNA target sequences are selected from one or more of the sequences of SEQ ID NOs: 44-57.

* * * * *